US011266720B2

(12) United States Patent
Dumont et al.

(10) Patent No.: US 11,266,720 B2
(45) Date of Patent: *Mar. 8, 2022

(54) FACTOR VIII-FC CHIMERIC AND HYBRID POLYPEPTIDES, AND METHODS OF USE THEREOF

(71) Applicant: BIOVERATIV THERAPEUTICS INC., Waltham, MA (US)

(72) Inventors: Jennifer A. Dumont, Groton, MA (US); Susan Low, Pepperill, MA (US); Alan J. Bitonti, Acton, MA (US); Glenn Pierce, Rancho Santa Fe, CA (US); Alvin Luk, Boston, MA (US); Haiyan Jiang, Belmont, MA (US); Byron McKinney, San Diego, CA (US); Matt Ottmer, Newton, MA (US); Jurg Sommer, Wayland, MA (US); Karen Nugent, Princes Risborough (GB); Lian Li, Lexington, MA (US); Robert Peters, Needham, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 164 days.

This patent is subject to a terminal disclaimer.

(21) Appl. No.: 16/270,302

(22) Filed: Feb. 7, 2019

(65) Prior Publication Data

US 2019/0262429 A1 Aug. 29, 2019

Related U.S. Application Data

(60) Continuation of application No. 14/964,289, filed on Dec. 9, 2015, now abandoned, which is a division of application No. 13/793,783, filed on Mar. 11, 2013, now Pat. No. 9,241,978, which is a division of application No. 13/513,424, filed as application No. PCT/US2010/059136 on Dec. 6, 2010, now Pat. No. 9,050,318.

(60) Provisional application No. 61/419,676, filed on Dec. 3, 2010, provisional application No. 61/410,929, filed on Nov. 7, 2010, provisional application No. 61/373,113, filed on Aug. 12, 2010, provisional application No. 61/363,065, filed on Jul. 9, 2010, provisional application No. 61/301,592, filed on Feb. 4, 2010, provisional application No. 61/285,054, filed on Dec. 9, 2009, provisional application No. 61/267,070, filed on Dec. 6, 2009.

(51) Int. Cl.
| | |
|---|---|
| C07K 14/755 | (2006.01) |
| A61K 38/37 | (2006.01) |
| A61K 47/64 | (2017.01) |
| A61K 47/68 | (2017.01) |
| C07K 16/46 | (2006.01) |

(52) U.S. Cl.
CPC ............ *A61K 38/37* (2013.01); *A61K 47/643* (2017.08); *A61K 47/6811* (2017.08); *C07K 14/755* (2013.01); *C07K 16/46* (2013.01); *C07K 2319/30* (2013.01); *Y02A 90/10* (2018.01)

(58) Field of Classification Search
None
See application file for complete search history.

(56) References Cited

U.S. PATENT DOCUMENTS

| | | | |
|---|---|---|---|
| 4,235,881 | A | 11/1980 | Cort |
| 4,757,006 | A | 7/1988 | Toole, Jr. et al. |
| 4,868,112 | A | 9/1989 | Toole, Jr. et al. |
| 4,965,199 | A | 10/1990 | Capon et al. |
| 4,994,371 | A | 2/1991 | Davie et al. |
| 5,004,803 | A | 4/1991 | Kaufman et al. |
| 5,112,950 | A | 5/1992 | Meulien et al. |
| 5,171,844 | A | 12/1992 | van Ooyen et al. |
| 5,364,771 | A | 11/1994 | Lollar et al. |
| 5,543,502 | A | 8/1996 | Nordfang et al. |
| 5,595,886 | A | 1/1997 | Chapman et al. |
| 5,610,278 | A | 3/1997 | Nordfang et al. |
| 5,693,499 | A | 12/1997 | Yonemura et al. |
| 5,789,203 | A | 8/1998 | Chapman et al. |
| 5,859,204 | A | 1/1999 | Lollar |
| 5,972,885 | A | 10/1999 | Spira et al. |
| 6,048,720 | A | 4/2000 | Dalborg et al. |
| 6,060,447 | A | 5/2000 | Chapman et al. |
| 6,228,620 | B1 | 5/2001 | Chapman et al. |
| 6,251,632 | B1 | 6/2001 | Lillicrap et al. |

(Continued)

FOREIGN PATENT DOCUMENTS

| | | |
|---|---|---|
| AU | 2016213822 B2 | 8/2017 |
| CN | 1863556 A | 11/2006 |

(Continued)

OTHER PUBLICATIONS

Armour, K. L., et al., "Recombinant human IgG molecules lacking Fcγ receptor I binding and monocyte triggering activities," Eur. J. Immunol. 29:2613-2624, Wiley-VCH Verlag GmbH, Germany (1999).

(Continued)

*Primary Examiner* — Michael Szperka
(74) *Attorney, Agent, or Firm* — Lathrop GPM LLP; James H. Velema, Esq.; James V. DeGiulio

(57) ABSTRACT

The present invention provides methods of administering Factor VIII; methods of administering chimeric and hybrid polypeptides comprising Factor VIII; chimeric and hybrid polypeptides comprising Factor VIII; polynucleotides encoding such chimeric and hybrid polypeptides; cells comprising such polynucleotides; and methods of producing such chimeric and hybrid polypeptides using such cells.

64 Claims, 19 Drawing Sheets

Figure 1:
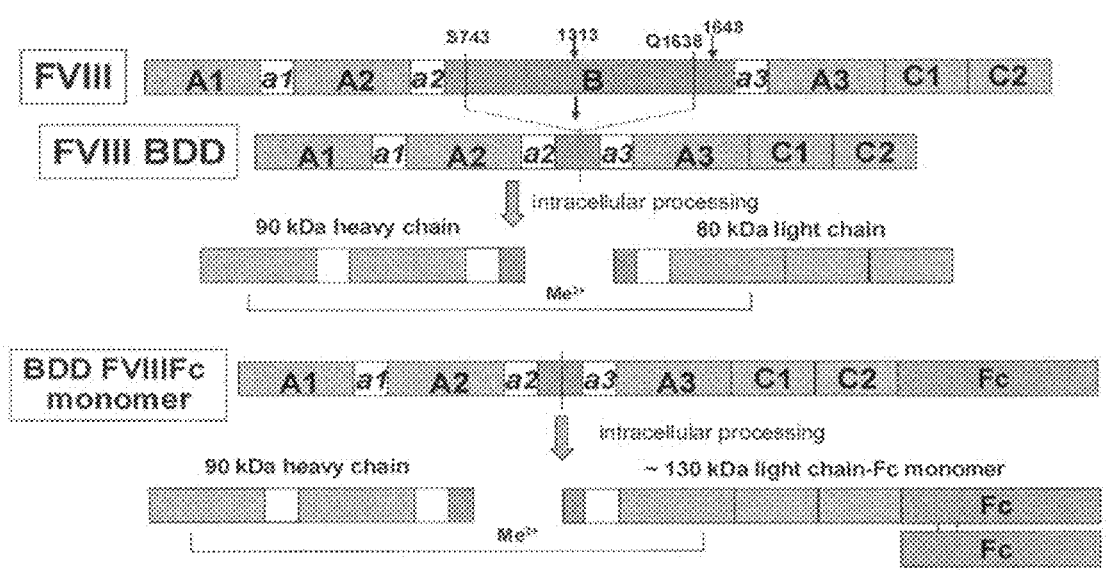

Specification includes a Sequence Listing.

(56) References Cited

U.S. PATENT DOCUMENTS

| | | |
|---|---|---|
| 6,316,226 B1 | 11/2001 | Van Ooyen et al. |
| 6,346,513 B1 | 2/2002 | Van Ooyen et al. |
| 6,376,463 B1 | 4/2002 | Lollar |
| 6,458,563 B1 | 10/2002 | Lollar |
| 6,686,179 B2 | 2/2004 | Fleer et al. |
| 6,818,439 B1 | 11/2004 | Jolly et al. |
| 7,041,635 B2 | 5/2006 | Kim et al. |
| 7,211,559 B2 | 5/2007 | Saenko et al. |
| 7,348,004 B2 | 3/2008 | Peters et al. |
| 7,381,408 B2 | 6/2008 | Mezo et al. |
| 7,404,956 B2 | 7/2008 | Peters et al. |
| 7,592,010 B2 | 9/2009 | Rosen et al. |
| 7,632,921 B2 | 12/2009 | Pan et al. |
| 7,683,158 B2 | 3/2010 | Siekmann et al. |
| 7,790,415 B2 | 9/2010 | Gillies et al. |
| 7,820,162 B2 | 10/2010 | Mezo et al. |
| 8,329,182 B2 | 12/2012 | Peters et al. |
| 8,367,805 B2 | 2/2013 | Chamberlain et al. |
| 9,050,318 B2 * | 6/2015 | Dumont .................... A61P 7/04 |
| 9,241,978 B2 | 1/2016 | Dumont et al. |
| 10,786,554 B2 * | 9/2020 | Maloney ................ A61K 38/37 |
| 2003/0199444 A1 | 10/2003 | Knudsen et al. |
| 2005/0147618 A1 | 7/2005 | Rivera et al. |
| 2005/0260194 A1 | 11/2005 | Peters et al. |
| 2005/0266533 A1 | 12/2005 | Ballance et al. |
| 2006/0159675 A1 | 7/2006 | Jiao et al. |
| 2008/0261877 A1 | 10/2008 | Ballance et al. |
| 2009/0092582 A1 | 4/2009 | Bogin et al. |
| 2010/0189682 A1 | 7/2010 | Schellenberger et al. |
| 2013/0108629 A1 | 5/2013 | Dumont et al. |
| 2013/0171138 A1 | 7/2013 | Peters et al. |
| 2013/0274194 A1 | 10/2013 | Dumont et al. |
| 2014/0294821 A1 | 10/2014 | Dumont et al. |
| 2016/0199455 A1 | 7/2016 | Dumont et al. |

FOREIGN PATENT DOCUMENTS

| | | | |
|---|---|---|---|
| EA | 200501756 A1 | 8/2006 | |
| EP | 0 295 597 A2 | 12/1988 | |
| EP | 1 444 986 A1 | 8/2004 | |
| EP | 2506868 A2 | 10/2012 | |
| EP | 3326643 A1 | 5/2018 | |
| JP | 2007500744 A | 1/2007 | |
| JP | 6062459 B2 | 12/2016 | |
| JP | 2016209535 A | 12/2016 | |
| WO | WO 8704187 A1 | 7/1987 | |
| WO | WO 8800831 A1 | 2/1988 | |
| WO | WO 8803558 A1 | 5/1988 | |
| WO | WO 8808035 A1 | 10/1988 | |
| WO | WO 9109122 A1 | 6/1991 | |
| WO | WO 9320093 A1 | 10/1993 | |
| WO | WO 9411503 A2 | 5/1994 | |
| WO | WO 2004101739 A2 | 11/2004 | |
| WO | WO 2004101740 A2 | 11/2004 | |
| WO | WO 2005001025 A2 | 1/2005 | |
| WO | WO-2005001025 A2 * | 1/2005 | ................ A61P 7/00 |
| WO | WO 2006074199 A1 | 7/2006 | |
| WO | WO 2007103515 A2 | 9/2007 | |
| WO | WO 2008077616 A1 | 7/2008 | |
| WO | WO 2009023270 A2 | 2/2009 | |
| WO | WO 2010/091122 A1 | 8/2010 | |
| WO | WO 2010111414 A1 | 9/2010 | |
| WO | WO-2010111414 A1 * | 9/2010 | ........... C07K 14/755 |
| WO | WO 2010133834 A2 | 11/2010 | |
| WO | WO 2013009627 A2 | 1/2013 | |

OTHER PUBLICATIONS

Ashkanazi, A., et al., "Immunoadhesions," International Reviews of Immunology 10(2-3):219-227, Harwood Academic Publishers GmbH, United States (1993).

Berkner, K. L., "Expression of Recombinant Vitamin K-Dependent Proteins in Mammalian Cells: Factors IX and VII," Methods in Enzymology 222:450-477, Academic Press, United States (1993).

Bi, L., et al., "Targeted disruption of the mouse factor VIII gene produces a model of haemophilia A," Nature Genetics 10(1):119-121, Nature Publishing Company, United States (1995).

Bitonti, A. J. and Dumont, J.A., "Pulmonary administration of therapeutic proteins using an immunoglobulin transport pathway," Advanced Drug Delivery Reviews 58:1106-1118, Elsevier B.V., Netherlands (2006).

Blanchette, P., et al., "A survey of factor prophylaxis in the Canadian haemophilia A population," Haemophilia 10(6):679-683, Blackwell Publishing, England (2004).

Blanchette, V.S., et al., "Plasma and albumin-free recombinant factor VIII: pharmacokinetics, efficacy and safety in previously treated pediatric patients," Journal of Thrombosis and Haemostasis 6:1319-1326, International Society on Thrombosis and Haemostasis, Blackwell Publishing, England (2008).

Brinkhous, K., et al., "Preclinical Pharmacology of Albumin-Free B-domain Deleted Recombinant Factor VIII," Seminars in Thrombosis and Hemostasis 28(3):269-272, Thieme Medical Publishers, Inc., United States (2002).

Brutlag, D.L., et al., "Improved sensitivity of biological sequence database searches," CABIOS 6(3):237-245, Oxford University Press, England (1990).

Burmeister, W.P., et al., "Crystal structure of the complex of rat neonatal Fc receptor with Fc," Nature 372:379-383, Nature Publishing Group, England (1994).

Cameron, C., et al., "The Canine Factor VIII cDNA and 5' Flanking Sequence," Thrombosis and Haemostasis 79(2):317-322, Schattauer Verlag, Stuttgart, Germany (1998).

Chamow, S.M. and Ashkenazi, A., "Immunoadhesins: Principles and Applications," Trends in Biotechnology 14:52-60, Elsevier Science Ltd., England (1996).

Chang, J-Y., et al., "Replacing the First Epidermal Growth Factor-like Domain of Factor IX with That of Factor VII Enhances Activity In Vitro and in Canine Hemophilia B," J. Clin. Invest. 100(4):886-892, The American Society for Clinical Investigation, Inc., United States (1997).

Cutler, J.A., et al., "The Identification and Classification of 41 Novel Mutations in the Factor VIII Gene (F8C)," Human Mutation 19(3):274-278, Wiley-Liss, Inc., United States (2002).

Dobeli, H., et al., "Role of the carboxy-terminal sequence on the biological activity of human interferon (IFN-γ)," Journal of Biotechnology 7: 199-216, Elsevier Science Publishers B.V., Netherlands (1988).

Dumont, J.A., et al., "Delivery of an Erythropoietin-Fc Fusion Protein by Inhalation in Humans through an Immunoglobulin Transport Pathway," Journal of Aerosol Medicine 18(3):294-303, Mary Ann Liebert, Inc., United States (2005).

Dumont, J.A., et al., "Monomeric Fc Fusions: Impact on Pharmacokinetic and Biological Activity of Protein Therapeutics," BioDrugs 20(3): 151-160, Adis Data Information B.V., United States (2006).

Dumont, J.A., et al., "Factor VIII-Fc Fusion Protein Shows Extended Half-Life and Hemostatic Activity in Hemophilia A Dogs," Blood: Journal of the American Society of Hematology 144(22):228, 51st Annual Meeting Abstracts, Abstract 545, The American Society of Hematology, United States (2009).

Dumont, J.A., et al., "Prolonged activity of a recombinant factor VIII-Fc Fusion protein in hemophilia A mice and dogs," Blood 119(13):3024-3030, The American Society of Hematology, United States (2012).

Eaton, D. L., et al., "Construction and Characterization of an Active Factor VIII Variant Lacking the Central One-Third of the Molecule," Biochemistry 25(26):8343-8347, American Chemical Society, United States (1986).

Ellis, C.N. and Krueger, G.G., "Treatment of Chronic Plaque Psoriasis by Selective Targeting of Memory Effector T Lymphocytes," The New England Journal of Medicine 345(4):248-255, Massachusetts Medical Society, United States (2001).

Fay, P.J., "Factor VIII Structure and Function," International Journal of Hematology 83(2):103-108, The Japanese Society of Hematology, Japan (2006).

(56) References Cited

OTHER PUBLICATIONS

Fisher, C.J., et al., "Treatment of Septic Shock with the Tumor Necrosis Factor Receptor: Fc Fusion Protein," The New England Journal of Medicine 334(26):1697-1702, Massachusetts Medical Society, United States (1996).
Friend, P.J., et al., "Phase I Study of an Engineered Aglycosylated Humanized CD3 Antibody in Renal Transplant Rejection," Transplantation 68(11):1632-1637, Lipponcott Williams & Wilkins, Inc., United States (1999).
Gayle, R.B., et al., "Identification of Regions in lnterleukin-1α Important for Activity," The Journal of Biological Chemistry 268(29):22105-22111, The American Society for Biochemistry and Molecular Biology, Inc., United States (1993).
Ghetie, V. and Ward, E.S., "Multiple Roles for the Major Histocompatibility Complex Class I-Related Receptor FcRn," Annu. Rev. Immunol. 18:739-766, Annual Reviews, United States (2000).
Gitschier, J., et al., "Characterization of the human factor VIII gene," Nature 312(5992):326-330, Nature Publishing Group, England (1984).
Graham, J.B., et al., "Canine Hemophilia: Observations on the Course, the Clotting Anomaly, and the Effect of Blood Transfusions," The Journal of Experimental Medicine 90(2):97-111, Rockefeller University Press, United States (1949).
Healey, J.F., et al., "The cDNA and Derived Amino Acid Sequence of Porcine Factor VIII," Blood 88(11):4209-4214, The American Society of Hematology, United States (1996).
Hoeben, R.C., et al., "Expression of Functional Factor VIII in Primary Human Skin Fibroblasts after Retrovirus-mediated Gene Transfer," Journal of Biological Chemistry 265(13):7318-7323, The American Society for Biochemistry and Molecular Biology, Inc., United States (1990).
International Search Report and Written Opinion for International Application No. PCT/US10/059136, ISA/US, Commissioner for Patents, United States, dated Jun. 2, 2011.
Lagner, K.D., et al., "Synthesis of Biologically Active Deletion Mutants of Human Factor VIII:C," Behring Institute Mitteilungen 82:16-25, Behringwerke AG, Germany (1988).
Lollar, P. and Parker, E.T., "Structural Basis forthe Decreased Procoagulant Activity of Human Factor VIII Compared to the Porcine Homolog," The Journal of Biological Chemistry 266(19):12481-12486, The American Society of Biochemistry and Molecular Biology, Inc., United States (1991).
Lollar, P., et al., "Coagulant Properties of Hybrid Human/Porcine Factor VIII Molecules," The Journal of Biological Chemistry 267(33):23652-23657, The American Society of Biochemistry and Molecular Biology, Inc., United States (1992).
Low, S.C., et al., "Oral and pulmonary delivery of FSH-Fc fusion proteins via neonatal Fc Receptor-mediated transcytosis," Human Reproduction 20(7):1805-1813, Oxford University Press, England (2005).
Lozier, J.N., et al., "The Chapel Hill hemophilia A dog colony exhibits a factor VIII gene inversion," PNAS 99(20):12991-12996, National Academy of Sciences, United States (2002).
Manco-Johnson, M., "Comparing prophylaxis with episodic treatment in haemophilia A: implications for clinical practice," Haemophilia 13(Suppl. 2):4-9, Blackwell Publishing Ltd., England (2007).
Manco-Johnson, M.J., et al., "Prophylaxis versus Episodic Treatment to Prevent Joint Disease in Boys with Severe Hemophilia," The New England Journal of Medicine 357(6):535-544, Massachusetts Medical Society, United States (2007).
Mannucci, P.M., et al., "The Hemophilias—from Royal Genes to Gene Therapy," The New England Journal of Medicine 344(23):1773-1779, Massachusetts Medical Society, United States (2001).
Mccue, J.T., et al., "Application of a Novel Affinity Adsorbent for the Capture and Purification of Recombinant Factor VIII Compounds," Journal of Chromatography A 1216(45):7824-7830, Elsevier B.V., Netherlands (2009).
Mei, B., et al., "Rational design of a fully active, long-acting PEGylated factor VIII for hemophilia A treatment," Blood 116(2):270-279, American Society of Hematology, United States (2010).
Meulien, P., et al., "A new recombinant procoagulant protein derived from the cDNA encoding human factor VIII," Protein Engineering 2(4):301-306, IRL Press Ltd., United States (1988).
Morfini, M., "Pharmacokinetics of factor VIII and factor IX," Haemophilia 9(Suppl. 1):94-100, Blackwell Publishing Ltd., England (2003).
Oganesyan, V., et al., "Structural characterization of a human Fc fragment engineered for extended serum half-life," Molecular Immunology 46(8-9):1750-1755, Elsevier Ltd., Netherlands (2009).
Pan, J., et al., "Enhanced efficacy of recombinant FVIII in noncovalent complex with PEGylated liposome in hemophilia A mice," Blood 114(13):2802-2811, The American Society of Hematology, United States (2009).
Peyvandi, F., et al., "Genetic diagnosis of haemophilia and other inherited bleeding disorders," Haemophilia 12(Suppl. 3):82-89, Blackwell Publishing Ltd., England (2006).
Raut, S., et al., "Phospholipid binding of factor VIII in different therapeutic concentrates," British Journal of Haematology 107:323-329, Blackwell Science Ltd., England (1999).
Rodriguez-Merchan, E.C., "Management of Musculoskeletal Complications of Hemophilia," Seminars in Thrombosis and Hemostasis 29(1):87-96, Thieme Medical Publishers, Inc., United States (2003).
Ron, D., et al., "Expression of Biologically Active Recombinant Keratinocyte Growth Factor: Structure/Function Analysis of Amino-Terminal Truncation Mutants," The Journal of Biological Chemistry 268(4):2984-2988, American Society for Biochemistry and Molecular Biology, United States (1993).
Roopenian, D.C. and Akilesh, S., "FcRn: the neonatal Fc receptor comes of age," Nature Reviews: Immunology 7:715-725, Nature Publishing Group, England (2007).
Rostin J., et al., "B-Domain Deleted Recombinant Coagulation Factor VIII modified with Monomethoxy Polyethylene Glycol," Bioconjugate Chemistry 11 (3):387-396, American Chemical Society, United States (2000).
Routledge, E.G., et al., "The Effect of Aglycosylation on the Immunogenicity of a Humanized Therapeutic CD3 Monoclonal Antibody," Transplantation 60(8):847-853, Williams & Wilkins, United States (1995).
Sarver, N., et al., "Stable Expression of Recombinant Factor VIII Molecules Using a Bovine Papillomavirus Vector," DNA 6(6):553-564, Mary Ann Liebert Inc., United States (1987).
Schellenberger, V., et al., "A recombinant polypeptide extends the in vivo half-life of peptides and proteins in a tunable manner," Nature Biotechnology 27(12): 1186-1190, Nature America, Inc., United States (2009).
Schulte S., "Use of albumin fusion technology to prolong the half-life of recombinant factor VIIa," Thrombosis Research 122(Suppl. 4J:S14-S19, Elsevier Ltd., Netherlands (2008).
Schulte, S., "Half-life extension through albumin fusion technologies," Thrombosis Research 124(Suppl. 2J:S6-S8, Elsevier Ltd., Netherlands (2009).
Shields, R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604, The American Society of Biochemistry and Molecular Biology, Inc., United States (2001).
Spira, J., et al., "Prolonged bleeding-free period following prophylactic infusion of recombinant factor VIII reconstituted with pegylated liposomes," Blood 108(12):3668-3673, The American Society of Hematology, United States (2006).
Spira, J., et al., "Evaluation of liposomal dose in recombinant factor VIII reconstituted with pegylated liposomes for the treatment of patients with severe haemophilia A," Thrombosis and Haemostasis 100(3):429-434, SchattauerGmbH, Stuttgart, Germany (2008).
Srour, M.A., et al., "Modified expression of coagulation factor VIII by addition of a glycosylation site at the N terminus of the protein," Annals of Hematology 87(2):107-112, Springer-Verlag, Germany (2008).
Stennicke, H.R., et al., "Generation and biochemical characterization of glycoPEGylated factor VIIa derivatives," Thrombosis and Haemostasis 100(5):920-928, SchattauerGmbH, Stuttgart, Germany (2008).

(56) References Cited

OTHER PUBLICATIONS

Story, C.M., et al., "A Major Histocompatibility Complex Class I-like Fc Receptor Cloned from Human Placenta: Possible Role in Transfer of Immunoglobulin G from Mother to Fetus," Journal of Experimental Medicine 180:2377-2381, The Rockefeller University Press, United States (1994).
Supplementary European Search Report for EP Application No. EP10835255, Munich, Germany, dated Jun. 20, 2013.
Toole, J.J., et al., "Molecular cloning of a cDNA encoding human antihaemophilic factor," Nature 312(5992):342-347, Nature Publishing Group, England (1984).
Toole, J.J., et al., "A Large Region (approximately equal to 95 kDa) of Human Factor VIII is Dispensable for in vitro Procoagulant Activity," Proceedings of the National Academy of Sciences 83(16):5939-5942, National Academy of Sciences, United States (1986).
Vaccaro, C., et al., "Engineering the Fc region of immunoglobulin G to modulate in vivo antibody levels," Nature Biotechnology 23(10):1283-1288, Nature America Publishing, United States (2005).
Vehar, G.A., et al., "Structure of human factor VIII," Nature 312(5992):337-342, Nature Publishing Group, England (1984).
Ward, E.S. and Ghetie, V.,"The effector functions of immunoglobulins: implications for therapy," Therapeutic Immunology 2(2):77-94, Blackwell Science Ltd., England (1995).
White, G.C., et al., "A Multicenter Study of Recombinant Factor VIII (Recombinate™) in Previously Treated Patients with Hemophilia A," Thrombosis and Haemostasis 77(4):660-667, Stuttgart, Germany (1997).
Wood, W.I., et al., "Expression of active human factor VIII from recombinant DNA clones," Nature 312(5992):330-337, Nature Publishing Group, England (1984).

English language abstract of European Patent Application No. EP 0 295 597 A2, European Patent Office, Espacenet database—Worldwide (Jul. 3, 2014).
Stieltjes, N., et al., "Continuous infusion of B-domain deleted recombinant factor VIII (ReFacto) in patients with haemophilia A undergoing surgery: clinical experience," Haemophilia 10(5):452-458, Blackwell Science, England (2004).
U.S. National Institutes of Health, "Study of recombinant Factor VIII Fc Fusion Protein (rFVIIIFc) in Subjects With Severe Hemophilia A, ClinicalTrials.gov Identifier NCT01027377," clinicaltrials.gov, accessed at https://clinicaltrials.gov/ct2/show/NCT01027377, 3 pages.
Pittman, D.D., et al., "Biochemical, immunological, and in vivo functional characterization of B-domain-deleted factor VIII," Blood 81 (11) :2925-2935, American Society of Hematology, United States (1993).
U.S. Appl. No. 16/270,302 2019/0262429, filed Feb. 7, 2019, Aug. 29, 2019, Jennifer A. Dumont.
U.S. Appl. No. 14/964,289 2016/0199455, filed Dec. 9, 2015 Jul. 14, 2016, Jennifer A. Dumont.
U.S. Appl. No. 13/793,783 2013/0274194 U.S. Pat. No. 9,241,978, filed Mar. 11, 2013 Oct. 17, 2013 Jan. 26, 2016, Jennifer A. Dumont.
U.S. Appl. No. 13/513,424 2013/0108629 U.S. Pat. No. 9,050,318, filed Dec. 28, 2012 May 2, 2013 Jun. 9, 2015, Jennifer A. Dumont.
Chaudhury et al., "Albumin Binding to FcRn: Distinct from the FcRn-IgG Interaction", Biochemistry, Apr. 18, 2006, vol. 45, No. 15, pp. 4983-4990.
Recht et al., "Clinical evaluation of moroctocog alfa (AF—CC), a new generation of B-domain deleted recombinant factor VIII (BDDrFVIII) for treatment of haemophilia A: demonstration of safety, efficacy, and pharmacokinetic equivalence to full-length recombinant factor VIII", Haemophilia, Jul. 2009, 15(4): 859-880.

\* cited by examiner

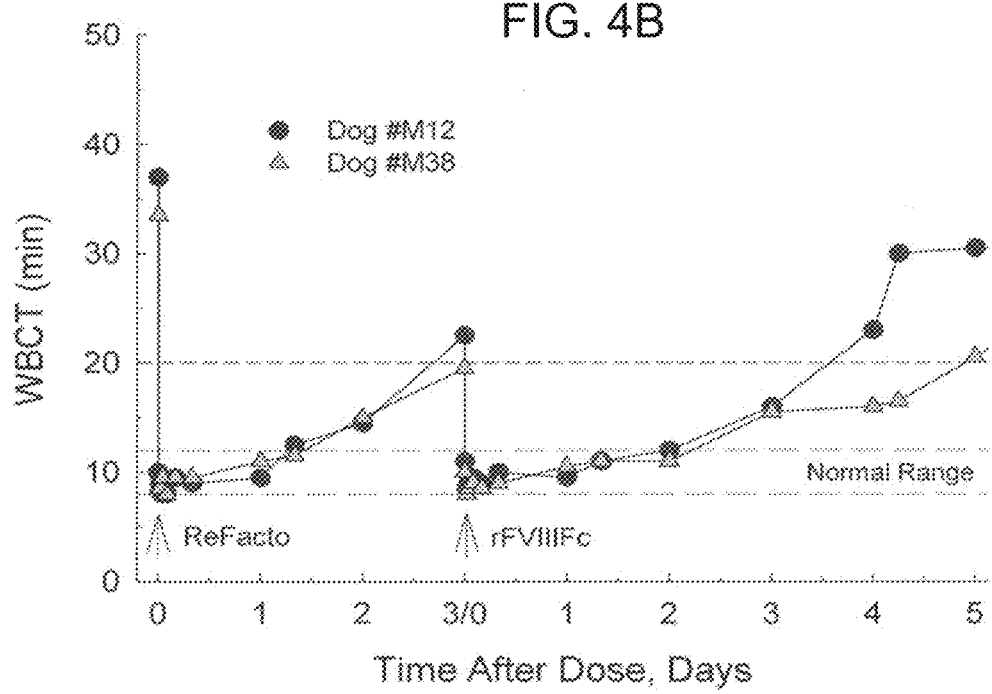

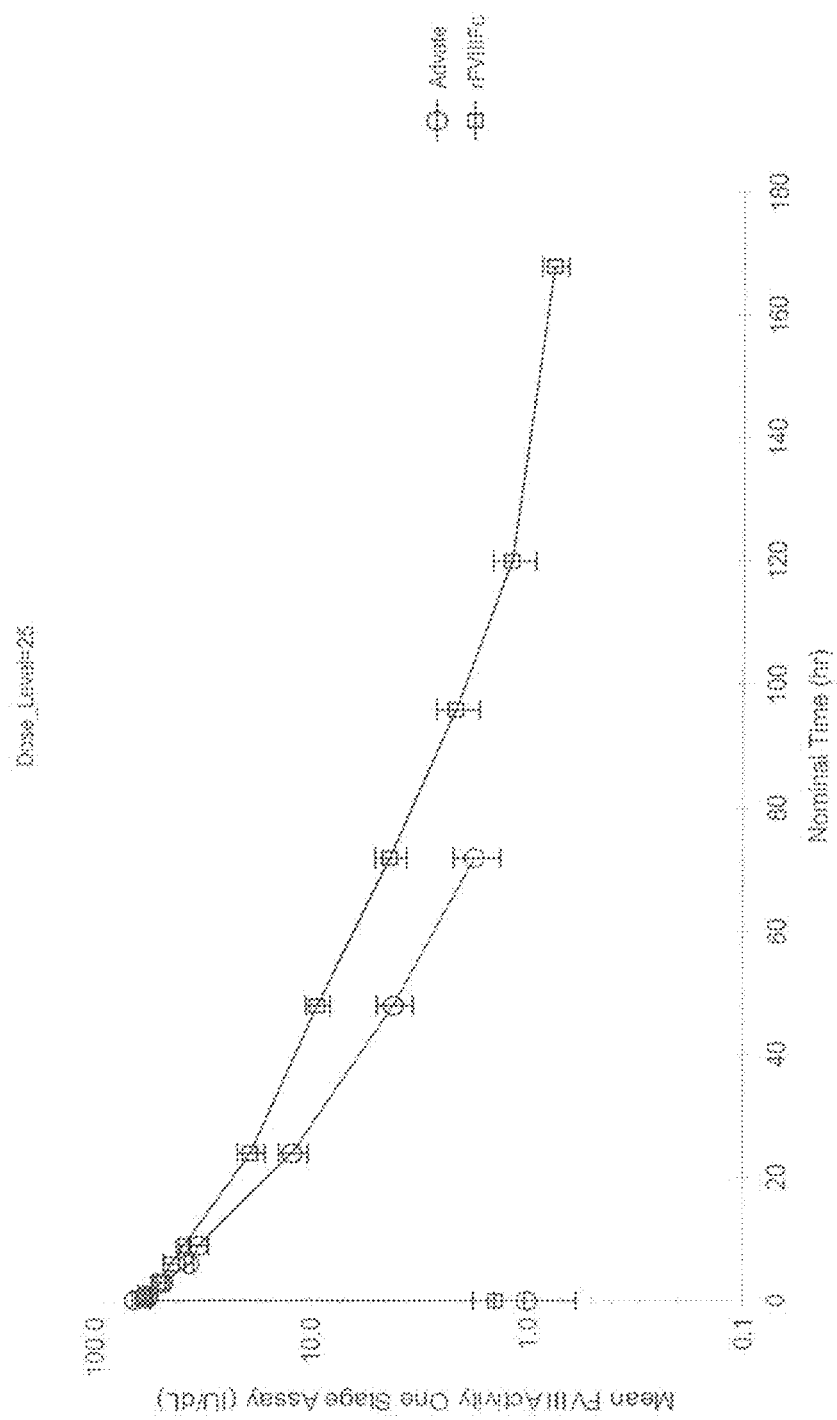

SEQUENCE LISTING

<160> NUMBER OF SEQ ID NOS: 12

<210> SEQ ID NO 1
<211> LENGTH: 5052
<212> TYPE: DNA
<213> ORGANISM: Artificial Sequence
<220> FEATURE:
<223> OTHER INFORMATION: B-Domain Deleted FVIIIFc Chain

```
<220> FEATURE:
<221> NAME/KEY: misc_signal
<222> LOCATION: (1)..(57)
<223> OTHER INFORMATION: FVIII signal
<220> FEATURE:
<221> NAME/KEY: misc_feature
<222> LOCATION: (4372)..(5052)
<223> OTHER INFORMATION: Fc region

<400> SEQUENCE: 1
atgcaaatag agctctccac ctgcttcttt ctgtgccttt tgcgattctg ctttagtgcc      60
accagaagat actacctggg tgcagtggaa ctgtcatggg actatatgca agtgatctc     120 ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaagacttt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca aagttataa agtcaatat ttgaacaatg gccctcagcg gattggtagg    1320
aagtacaaaa agtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataacct caaacacaaa   2040
```

```
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc atcaacggg  aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga cacaagtgac agtacaggaa    3000
tttgctctgt ttttcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactcccctg ggaatggctt ctggacacat tagagatttt    3480
cagattacag cttcaggaca atatggacag tgggcccca  agctggccag acttcattat    3540
tccggatcaa tcaatgcctg gagcaccaag gagccctttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctcttttt    4200 cagaatggca aagtaaaggt ttttcaggga aatcaagact ccttcacacc tgtggtgaac    4260
tctctagacc caccgttact gactcgctac cttcgaattc accccagag ttgggtgcac    4320 cagattgcct gaggatgga  ggttctgggc tgcgaggcac aggacctcta cgacaaaact    4380
cacacatgcc caccgtgccc agctccagaa ctcctgggcg gaccgtcagt cttcctcttc    4440
```

```
cccccaaaac caaggacac cctcatgatc tcccggaccc ctgaggtcac atgcgtggtg    4500
gtggacgtga gccacgaaga ccctgaggtc aagttcaact ggtacgtgga cggcgtggag    4560
gtgcataatg ccaagacaaa gccgcgggag gagcagtaca acagcacgta ccgtgtggtc    4620
agcgtcctca ccgtcctgca ccaggactgg ctgaatggca aggagtacaa gtgcaaggtc    4680
tccaacaaag ccctcccagc ccccatcgag aaaaccatct ccaaagccaa agggcagccc    4740
cgagaaccac aggtgtacac cctgccccca tcccgggatg agctgaccaa gaaccaggtc    4800
agcctgacct gcctggtcaa aggcttctat cccagcgaca tcgccgtgga gtgggagagc    4860
aatgggcagc cggagaacaa ctacaagacc acgcctcccg tgttggactc cgacggctcc    4920
ttcttcctct acagcaagct caccgtggac aagagcaggt ggcagcaggg gaacgtcttc    4980
tcatgctccg tgatgcatga ggctctgcac aaccactaca cgcagaagag cctctccctg    5040
tctccgggta aa                                                         5052
```

<210> SEQ ID NO 2
<211> LENGTH: 1684
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: SIGNAL
<222> LOCATION: (1)..(19)
<220> FEATURE:
<221> NAME/KEY: mat_peptide
<222> LOCATION: (20)..(1684)
<220> FEATURE:
<221> NAME/KEY: MISC_FEATURE
<222> LOCATION: (20)..(753)
<223> OTHER INFORMATION: Heavy chain (HC)
<220> FEATURE:
<221> NAME/KEY: MISC_FEATURE
<222> LOCATION: (760)..(773)
<223> OTHER INFORMATION: B domain
<220> FEATURE:
<221> NAME/KEY: MISC_FEATURE
<222> LOCATION: (1457)..(1684)
<223> OTHER INFORMATION: Fc region

<400> SEQUENCE: 2

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
```

```
            145                 150                 155                 160
Lys Glu Asn Gly Pro Met Ala Ser Asp Pro Leu Cys Leu Thr Tyr Ser
                    165                 170                 175
Tyr Leu Ser His Val Asp Leu Val Lys Asp Leu Asn Ser Gly Leu Ile
                    180                 185                 190
Gly Ala Leu Leu Val Cys Arg Glu Gly Ser Leu Ala Lys Glu Lys Thr
                    195                 200                 205
Gln Thr Leu His Lys Phe Ile Leu Leu Phe Ala Val Phe Asp Glu Gly
            210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                    245                 250                 255
Val Asn Arg Ser Leu Pro Gly Leu Ile Gly Cys His Arg Ser Ser Val
                    260                 265                 270
Tyr Trp His Val Ile Gly Met Gly Thr Thr Pro Glu Val His Ser Ile
                    275                 280                 285
Phe Leu Glu Gly His Thr Phe Leu Val Arg Asn His Arg Gln Ala Ser
            290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                    325                 330                 335
Asp Gly Met Glu Ala Tyr Val Lys Val Asp Ser Cys Pro Glu Glu Pro
                    340                 345                 350
Gln Leu Arg Met Lys Asn Asn Glu Glu Ala Glu Asp Tyr Asp Asp Asp
                    355                 360                 365
Leu Thr Asp Ser Glu Met Asp Val Val Arg Phe Asp Asp Asp Asn Ser
            370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                    405                 410                 415
Leu Val Leu Ala Pro Asp Asp Arg Ser Tyr Lys Ser Gln Tyr Leu Asn
                    420                 425                 430
Asn Gly Pro Gln Arg Ile Gly Arg Ser Tyr Lys Lys Val Arg Phe Met
                    435                 440                 445
Ala Tyr Thr Asp Glu Thr Phe Lys Thr Arg Glu Ala Ile Gln His Glu
            450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                    485                 490                 495
His Gly Ile Thr Asp Val Arg Pro Leu Tyr Ser Arg Arg Leu Pro Lys
                    500                 505                 510
Gly Val Lys His Leu Lys Asp Phe Pro Ile Leu Pro Gly Glu Ile Phe
                    515                 520                 525
Lys Tyr Lys Trp Thr Val Thr Val Glu Asp Gly Pro Thr Lys Ser Asp
                    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                    565                 570                 575
```

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
    675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
    755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
    835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
    915                 920                 925

Ser Asn Phe Val Lys Pro Asn Glu Thr Lys Thr Tyr Phe Trp Lys Val
930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

```
Gly Arg Gln Val Thr Val Gln Glu  Phe Ala Leu Phe Phe  Thr Ile Phe
        995                1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Ser Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320

Met Phe  Ala Thr Trp Ser Pro  Ser Lys Ala Arg Leu  His Leu Gln
    1325                1330                1335

Gly Arg  Ser Asn Ala Trp Arg  Pro Gln Val Asn Asn  Pro Lys Glu
    1340                1345                1350

Trp Leu  Gln Val Asp Phe Gln  Lys Thr Met Lys Val  Thr Gly Val
    1355                1360                1365

Thr Thr  Gln Gly Val Lys Ser  Leu Leu Thr Ser Met  Tyr Val Lys
    1370                1375                1380

Glu Phe  Leu Ile Ser Ser Ser  Gln Asp Gly His Gln  Trp Thr Leu
```

Phe Phe Gln Asn Gly Lys Val Lys Val Phe Gln Gly Asn Gln Asp
        1400                1405                1410
Ser Phe Thr Pro Val Val Asn Ser Leu Asp Pro Leu Leu Thr
    1415                1420                1425
Arg Tyr Leu Arg Ile His Pro Gln Ser Trp Val His Gln Ile Ala
    1430                1435                1440
Leu Arg Met Glu Val Leu Gly Cys Glu Ala Gln Asp Leu Tyr Asp
    1445                1450                1455
Lys Thr His Thr Cys Pro Pro Cys Pro Ala Pro Glu Leu Leu Gly
    1460                1465                1470
Gly Pro Ser Val Phe Leu Phe Pro Pro Lys Pro Lys Asp Thr Leu
    1475                1480                1485
Met Ile Ser Arg Thr Pro Glu Val Thr Cys Val Val Val Asp Val
    1490                1495                1500
Ser His Glu Asp Pro Glu Val Lys Phe Asn Trp Tyr Val Asp Gly
    1505                1510                1515
Val Glu Val His Asn Ala Lys Thr Lys Pro Arg Glu Glu Gln Tyr
    1520                1525                1530
Asn Ser Thr Tyr Arg Val Val Ser Val Leu Thr Val Leu His Gln
    1535                1540                1545
Asp Trp Leu Asn Gly Lys Glu Tyr Lys Cys Lys Val Ser Asn Lys
    1550                1555                1560
Ala Leu Pro Ala Pro Ile Glu Lys Thr Ile Ser Lys Ala Lys Gly
    1565                1570                1575
Gln Pro Arg Glu Pro Gln Val Tyr Thr Leu Pro Pro Ser Arg Asp
    1580                1585                1590
Glu Leu Thr Lys Asn Gln Val Ser Leu Thr Cys Leu Val Lys Gly
    1595                1600                1605
Phe Tyr Pro Ser Asp Ile Ala Val Glu Trp Glu Ser Asn Gly Gln
    1610                1615                1620
Pro Glu Asn Asn Tyr Lys Thr Thr Pro Pro Val Leu Asp Ser Asp
    1625                1630                1635
Gly Ser Phe Phe Leu Tyr Ser Lys Leu Thr Val Asp Lys Ser Arg
    1640                1645                1650
Trp Gln Gln Gly Asn Val Phe Ser Cys Ser Val Met His Glu Ala
    1655                1660                1665
Leu His Asn His Tyr Thr Gln Lys Ser Leu Ser Leu Ser Pro Gly
    1670                1675                1680
Lys

<210> SEQ ID NO 3
<211> LENGTH: 741
<212> TYPE: DNA
<213> ORGANISM: Artificial Sequence
<220> FEATURE:
<223> OTHER INFORMATION: Fc region
<220> FEATURE:
<221> NAME/KEY: misc_signal
<222> LOCATION: (1)..(60)
<223> OTHER INFORMATION: Mouse Ig kappa signal

<400> SEQUENCE: 3
atggagacag acacactcct gctatgggta ctgctgctct gggttccagg ttccactggt        60
gacaaaactc acacatgccc accgtgccca gcacctgaac tcctgggagg accgtcagtc       120

```
ttcctcttcc ccccaaaacc caaggacacc ctcatgatct cccggacccc tgaggtcaca      180
tgcgtggtgg tggacgtgag ccacgaagac cctgaggtca agttcaactg gtacgtggac      240
ggcgtggagg tgcataatgc caagacaaag ccgcgggagg agcagtacaa cagcacgtac      300
cgtgtggtca gcgtcctcac cgtcctgcac caggactggc tgaatggcaa ggagtacaag      360
tgcaaggtct ccaacaaagc cctcccagcc cccatcgaga aaaccatctc caaagccaaa      420
gggcagcccc gagaaccaca ggtgtacacc ctgcccccat cccgcgatga gctgaccaag      480
aaccaggtca gcctgacctg cctggtcaaa ggcttctatc ccagcgacat cgccgtggag      540
tgggagagca atgggcagcc ggagaacaac tacaagacca cgcctcccgt gttggactcc      600
gacggctcct tcttcctcta cagcaagctc accgtggaca agagcaggtg gcagcagggg      660
aacgtcttct catgctccgt gatgcatgag gctctgcaca accactacac gcagaagagc      720
ctctccctgt ctccgggtaa a                                                741
```

```
<210> SEQ ID NO 4
<211> LENGTH: 247
<212> TYPE: PRT
<213> ORGANISM: Artificial Sequence
<220> FEATURE:
<223> OTHER INFORMATION: Fc chain
<220> FEATURE:
<221> NAME/KEY: SIGNAL
<222> LOCATION: (1)..(20)
<223> OTHER INFORMATION: Heterologous signal from Mouse Ig kappa chain
<220> FEATURE:
<221> NAME/KEY: mat_peptide
<222> LOCATION: (21)..(247)

<400> SEQUENCE: 4
```

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
                20                  25                  30

Glu Leu Leu Gly Gly Pro Ser Val Phe Leu Phe Pro Pro Lys Pro Lys
            35                  40                  45

Asp Thr Leu Met Ile Ser Arg Thr Pro Glu Val Thr Cys Val Val Val
    50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser

```
              210               215               220
Cys Ser Val Met His Glu Ala Leu His Asn His Tyr Thr Gln Lys Ser
225               230               235               240

Leu Ser Leu Ser Pro Gly Lys
            245

<210> SEQ ID NO 5
<211> LENGTH: 7734
<212> TYPE: DNA
<213> ORGANISM: Artificial Sequence
<220> FEATURE:
<223> OTHER INFORMATION: Full length FVIIIFc
<220> FEATURE:
<221> NAME/KEY: misc_signal
<222> LOCATION: (1)..(57)
<223> OTHER INFORMATION: FVIII signal
<220> FEATURE:
<221> NAME/KEY: misc_feature
<222> LOCATION: (7054)..(7734)
<223> OTHER INFORMATION: Fc region

<400> SEQUENCE: 5
atgcaaatag agctctccac ctgcttcttt ctgtgccttt tgcgattctg ctttagtgcc    60
accagaagat actacctggg tgcagtggaa ctgtcatggg actatatgca agtgatctc   120 ggtgagctgc ctgtggacgc aagatttcct cctagagtgc aaaatctttt ccattcaac   180 acctcagtcg tgtacaaaaa gactctgttt gtagaattca cggatcacct tttcaacatc   240
gctaagccaa ggccaccctg gatgggtctg ctaggtccta ccatccaggc tgaggtttat   300
gatacagtgg tcattacact taagaacatg gcttcccatc ctgtcagtct tcatgctgtt   360
ggtgtatcct actggaaagc ttctgaggga gctgaatatg atgatcagac cagtcaaagg   420
gagaaagaag atgataaagt cttccctggt ggaagccata catatgtctg gcaggtcctg   480
aaagagaatg gtccaatggc ctctgaccca ctgtgcctta cctactcata tctttctcat   540
gtggacctgg taaagacttt gaattcaggc ctcattggag ccctactagt atgtagagaa   600
gggagtctgg ccaaggaaaa gacacagacc ttgcacaaat ttatactact ttttgctgta   660
tttgatgaag ggaaaagttg gcactcagaa acaaagaact ccttgatgca ggatagggat   720
gctgcatctg ctcgggcctg gcctaaaatg cacacagtca atggttatgt aaacaggtct   780
ctgccaggtc tgattggatg ccacaggaaa tcagtctatt ggcatgtgat tggaatgggc   840
accactcctg aagtgcactc aatattcctc gaaggtcaca catttcttgt gaggaaccat   900
cgccaggcgt ccttggaaat ctcgccaata actttcctta ctgctcaaac actcttgatg   960
gaccttggac agtttctact gttttgtcat atctcttccc accaacatga tggcatggaa  1020
gcttatgtca agtagacag ctgtccagag aaccccaac tacgaatgaa aaataatgaa  1080
gaagcggaag actatgatga tgatcttact gattctgaaa tggatgtggt caggtttgat  1140
gatgacaact ctccttcctt tatccaaatt cgctcagttg ccaagaagca tcctaaaact  1200
tgggtacatt acattgctgc tgaagaggag gactgggact atgctccctt agtcctcgcc  1260
cccgatgaca aagttataa aagtcaatat ttgaacaatg cccctcagcg gattggtagg  1320
aagtacaaaa aagtccgatt tatggcatac acagatgaaa cctttaagac tcgtgaagct  1380
attcagcatg aatcaggaat cttgggacct ttactttatg ggaagttgg agacacactg  1440 ttgattatat ttaagaatca agcaagcaga ccatataaca tctaccctca cggaatcact  1500
gatgtccgtc ctttgtattc aaggagatta ccaaaaggtg taaacattt gaaggatttt  1560 ccaattctgc caggagaaat attcaaatat aaatggacag tgactgtaga agatgggcca  1620
```

```
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag agaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca tgccattga accaagaagc    2280
ttctcccaga attcaagaca ccctagcact aggcaaaagc aatttaatgc caccacaatt    2340
ccagaaaatg acatagagaa gactgacct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca    2520
cctggagcaa tagacagtaa taacagcctg tctgaaatga cacacttcag gcccacagctc    2580
catcacagtg gggacatggt attaccccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag acccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caagtggta gtaggaaagg gtgaatttac aaaggacgta    3540
ggactcaaag agatggtttt tccaagcagc agaaacctat ttcttactaa cttggataat    3600
ttacatgaaa ataatacaca caatcaagaa aaaaaaattc aggaagaaat agaaaagaag    3660
gaaacattaa tccaagagaa tgtagttttg cctcagatac atacagtgac tggcactaag    3720
aatttcatga agaacctttt cttactgagc actaggcaaa atgtagaagg ttcatatgac    3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
```

```
agccagcaga attttgtcac gcaacgtagt aagagagctt tgaaacaatt cagactccca    4020
ctagaagaaa cagaacttga aaaaaggata attgtggatg cacctcaac ccagtggtcc     4080 aaaaacatga acatttgac cccgagcacc ctcacacaga tagactacaa tgagaaggag     4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct tacaaggagc aaaaaaaat    4380 aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga gagtgtgaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt tccaggaatt tactgatggc    5280
tcctttactc agcccttata ccgtggagaa ctaaatgaac attggggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc tgctcatgg gagacaagtg acagtacagg aatttgctct gtttttcacc    5700
atctttgatg agaccaaaag ctggtacttc actgaaaata tggaaagaaa ctgcagggct    5760
ccctgcaata tccagatgga agatcccact tttaaagaga attatcgctt ccatgcaatc    5820
aatggctaca taatggatac actacctggc ttagtaatgg ctcaggatca aaggattcga    5880
tggtatctgc tcagcatggg cagcaatgaa acatccatt ctattcattt cagtggacat    5940
gtgttcactg tacgaaaaaa agaggagtat aaaatggcac tgtacaatct ctatccaggt    6000 gttttgaga cagtggaaat gttaccatcc aaagctggaa tttggcgggt ggaatgcctt    6060
attggcgagc atctacatgc tgggatgagc acttttttc tggtgtacag caataagtgt    6120
cagactcccc tgggaatggc ttctggacac attagagatt tcagattac agcttcagga    6180 caatatggac agtgggcccc aaagctggcc agacttcatt attccggatc aatcaatgcc    6240
tggagcacca aggagccctt tcttggatc aaggtggatc tgttggcacc aatgattatt    6300
cacggcatca agacccaggg tgcccgtcag aagttctcca gcctctacat ctctcagttt    6360
```

```
atcatcatgt atagtcttga tgggaagaag tggcagactt atcgaggaaa ttccactgga    6420
accttaatgg tcttctttgg caatgtggat tcatctggga taaaacacaa tattttaac    6480
cctccaatta ttgctcgata catccgtttg cacccaactc attatagcat tcgcagcact    6540
cttcgcatgg agttgatggg ctgtgattta aatagttgca gcatgccatt gggaatggag    6600
agtaaagcaa tatcagatgc acagattact gcttcatcct actttaccaa tatgtttgcc    6660
acctggtctc cttcaaaagc tcgacttcac ctccaaggga ggagtaatgc ctggagacct    6720
caggtgaata tccaaaaga gtggctgcaa gtggacttcc agaagacaat gaaagtcaca    6780
ggagtaacta ctcagggagt aaaatctctg cttaccagca tgtatgtgaa ggagttcctc    6840
atctccagca gtcaagatgg ccatcagtgg actctctttt ttcagaatgg caaagtaaag    6900
gttttcagg gaaatcaaga ctccttcaca cctgtggtga actctctaga cccaccgtta    6960
ctgactcgct accttcgaat tcaccccag agttgggtgc accagattgc cctgaggatg    7020
gaggttctgg gctgcgaggc acaggacctc tacgacaaaa ctcacacatg cccaccgtgc    7080
ccagctccag aactcctggg cggaccgtca gtcttcctct tccccccaaa acccaaggac    7140
accctcatga tctcccggac ccctgaggtc acatgcgtgg tggtggacgt gagccacgaa    7200
gaccctgagg tcaagttcaa ctggtacgtg gacggcgtgg aggtgcataa tgccaagaca    7260
aagccgcggg aggagcagta caacagcacg taccgtgtgg tcagcgtcct caccgtcctg    7320
caccaggact ggctgaatgg caaggagtac aagtgcaagg tctccaacaa agccctccca    7380
gcccccatcg agaaaaccat ctccaaagcc aaagggcagc cccgagaacc acaggtgtac    7440
accctgcccc catcccggga tgagctgacc aagaaccagg tcagcctgac ctgcctggtc    7500
aaaggcttct atcccagcga catcgccgtg gagtgggaga gcaatgggca gccggagaac    7560
aactacaaga ccacgcctcc cgtgttggac tccgacggct ccttcttcct ctacagcaag    7620
ctcaccgtgg acaagagcag gtggcagcag gggaacgtct tctcatgctc cgtgatgcat    7680
gaggctctgc acaaccacta cacgcagaag agcctctccc tgtctccggg taaa          7734
```

<210> SEQ ID NO 6
<211> LENGTH: 2578
<212> TYPE: PRT
<213> ORGANISM: Artificial Sequence
<220> FEATURE:
<223> OTHER INFORMATION: Full length FVIIIFc chain
<220> FEATURE:
<221> NAME/KEY: SIGNAL
<222> LOCATION: (1)..(19)
<223> OTHER INFORMATION: FVIII signal
<220> FEATURE:
<221> NAME/KEY: mat_peptide
<222> LOCATION: (20)..(2578)
<220> FEATURE:
<221> NAME/KEY: MISC_FEATURE
<222> LOCATION: (20)..(759)
<223> OTHER INFORMATION: HC
<220> FEATURE:
<221> NAME/KEY: MISC_FEATURE
<222> LOCATION: (760)..(1667)
<223> OTHER INFORMATION: B domain
<220> FEATURE:
<221> NAME/KEY: MISC_FEATURE
<222> LOCATION: (2352)..(2578)
<223> OTHER INFORMATION: Fc region

<400> SEQUENCE: 6

Met Gln Ile Glu Leu Ser Thr Cys Phe Phe Leu Cys Leu Leu Arg Phe
1               5                   10                  15

```
Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Ser Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Ser Tyr Lys Lys Val Arg Phe Met
```

```
                435                 440                 445
Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
850                 855                 860
```

-continued

```
Asp Met Val Phe Thr Pro Glu Ser Gly Leu Gln Leu Ala Arg Gln Glu
865                 870             875                 880

Lys Leu Gly Thr Thr Ala Ala Thr Glu Leu Lys Lys Leu Asp Phe Lys
                885             890                 895

Val Ser Ser Thr Ser Asn Asn Leu Ile Ser Thr Ile Pro Ser Asp Asn
            900             905                 910

Leu Ala Ala Gly Thr Asp Asn Thr Ser Ser Leu Gly Pro Pro Ser Met
        915             920             925

Pro Val His Tyr Asp Ser Gln Leu Asp Thr Leu Phe Gly Lys Lys
    930             935             940

Ser Ser Pro Leu Thr Glu Ser Gly Gly Pro Leu Ser Leu Ser Glu Glu
945             950             955                 960

Asn Asn Asp Ser Lys Leu Leu Glu Ser Gly Leu Met Asn Ser Gln Glu
            965             970                 975

Ser Ser Trp Gly Lys Asn Val Ser Ser Thr Glu Ser Gly Arg Leu Phe
            980             985             990

Lys Gly Lys Arg Ala His Gly Pro  Ala Leu Leu Thr Lys  Asp Asn Ala
        995              1000              1005

Leu Phe  Lys Val Ser Ile Ser  Leu Leu Lys Thr  Asn Lys Thr Ser
    1010              1015              1020

Asn Asn  Ser Ala Thr Asn Arg  Ser Thr His Ile Asp  Gly Pro Ser
    1025              1030              1035

Leu Leu  Ile Glu Asn Ser Pro  Ser Val Trp Gln Asn  Ile Leu Glu
    1040              1045              1050

Ser Asp  Thr Glu Phe Lys Lys  Val Thr Pro Leu Ile  His Asp Arg
    1055              1060              1065

Met Leu  Met Asp Lys Asn Ala  Thr Ala Leu Ala Arg  Gln His Met
    1070              1075              1080

Ser Asn  Lys Thr Thr Ser Ser  Lys Asn Met Glu Met  Val Gln Gln
    1085              1090              1095

Lys Lys  Glu Gly Pro Ile Pro  Pro Asp Ala Gln Asn  Pro Asp Met
    1100              1105              1110

Ser Phe  Phe Lys Met Leu Phe  Leu Pro Glu Ser Ala  Arg Trp Ile
    1115              1120              1125

Gln Arg  Thr His Gly Lys Asn  Ser Leu Asn Ser Gly  Gln Gly Pro
    1130              1135              1140

Ser Pro  Lys Gln Leu Val Ser  Leu Gly Pro Glu Lys  Ser Val Glu
    1145              1150              1155

Gly Gln  Asn Phe Leu Ser Glu  Lys Asn Lys Val Val  Val Gly Lys
    1160              1165              1170

Gly Glu  Phe Thr Lys Asp Val  Gly Leu Lys Glu Met  Val Phe Pro
    1175              1180              1185

Ser Ser  Arg Asn Leu Phe Leu  Thr Asn Leu Asp Asn  Leu His Glu
    1190              1195              1200

Asn Asn  Thr His Asn Gln Glu  Lys Lys Ile Gln Glu  Glu Ile Glu
    1205              1210              1215

Lys Lys  Glu Thr Leu Ile Gln  Glu Asn Val Val Leu  Pro Gln Ile
    1220              1225              1230

His Thr  Val Thr Gly Thr Lys  Asn Phe Met Lys Asn  Leu Phe Leu
    1235              1240              1245

Leu Ser  Thr Arg Gln Asn Val  Glu Gly Ser Tyr Asp  Gly Ala Tyr
    1250              1255              1260
```

-continued

```
Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Ser Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
```

-continued

```
        1655                1660                1665

Ile Thr Arg Thr Thr Leu Gln Ser Asp Gln Glu Ile Asp Tyr
        1670                1675                1680

Asp Asp Thr Ile Ser Val Glu Met Lys Lys Glu Asp Phe Asp Ile
        1685                1690                1695

Tyr Asp Glu Asp Glu Asn Gln Ser Pro Arg Ser Phe Gln Lys Lys
        1700                1705                1710

Thr Arg His Tyr Phe Ile Ala Ala Val Glu Arg Leu Trp Asp Tyr
        1715                1720                1725

Gly Met Ser Ser Ser Pro His Val Leu Arg Asn Arg Ala Gln Ser
        1730                1735                1740

Gly Ser Val Pro Gln Phe Lys Lys Val Val Phe Gln Glu Phe Thr
        1745                1750                1755

Asp Gly Ser Phe Thr Gln Pro Leu Tyr Arg Gly Glu Leu Asn Glu
        1760                1765                1770

His Leu Gly Leu Leu Gly Pro Tyr Ile Arg Ala Glu Val Glu Asp
        1775                1780                1785

Asn Ile Met Val Thr Phe Arg Asn Gln Ala Ser Arg Pro Tyr Ser
        1790                1795                1800

Phe Tyr Ser Ser Leu Ile Ser Tyr Glu Glu Asp Gln Arg Gln Gly
        1805                1810                1815

Ala Glu Pro Arg Ser Asn Phe Val Lys Pro Asn Glu Thr Lys Thr
        1820                1825                1830

Tyr Phe Trp Lys Val Gln His His Met Ala Pro Thr Lys Asp Glu
        1835                1840                1845

Phe Asp Cys Lys Ala Trp Ala Tyr Phe Ser Asp Val Asp Leu Glu
        1850                1855                1860

Lys Asp Val His Ser Gly Leu Ile Gly Pro Leu Leu Val Cys His
        1865                1870                1875

Thr Asn Thr Leu Asn Pro Ala His Gly Arg Gln Val Thr Val Gln
        1880                1885                1890

Glu Phe Ala Leu Phe Phe Thr Ile Phe Asp Glu Thr Lys Ser Trp
        1895                1900                1905

Tyr Phe Thr Glu Asn Met Glu Arg Asn Cys Arg Ala Pro Cys Asn
        1910                1915                1920

Ile Gln Met Glu Asp Pro Thr Phe Lys Glu Asn Tyr Arg Phe His
        1925                1930                1935

Ala Ile Asn Gly Tyr Ile Met Asp Thr Leu Pro Gly Leu Val Met
        1940                1945                1950

Ala Gln Asp Gln Arg Ile Arg Trp Tyr Leu Leu Ser Met Gly Ser
        1955                1960                1965

Asn Glu Asn Ile His Ser Ile His Phe Ser Gly His Val Phe Thr
        1970                1975                1980

Val Arg Ser Lys Glu Glu Tyr Lys Met Ala Leu Tyr Asn Leu Tyr
        1985                1990                1995

Pro Gly Val Phe Glu Thr Val Glu Met Leu Pro Ser Lys Ala Gly
        2000                2005                2010

Ile Trp Arg Val Glu Cys Leu Ile Gly Glu His Leu His Ala Gly
        2015                2020                2025

Met Ser Thr Leu Phe Leu Val Tyr Ser Asn Lys Cys Gln Thr Pro
        2030                2035                2040

Leu Gly Met Ala Ser Gly His Ile Arg Asp Phe Gln Ile Thr Ala
        2045                2050                2055
```

-continued

Ser Gly Gln Tyr Gly Gln Trp Ala Pro Lys Leu Ala Arg Leu His
2060            2065                2070

Tyr Ser Gly Ser Ile Asn Ala Trp Ser Thr Lys Glu Pro Phe Ser
2075            2080                2085

Trp Ile Lys Val Asp Leu Leu Ala Pro Met Ile Ile His Gly Ile
2090            2095                2100

Lys Thr Gln Gly Ala Arg Gln Lys Phe Ser Ser Leu Tyr Ile Ser
2105            2110                2115

Gln Phe Ile Ile Met Tyr Ser Leu Asp Gly Lys Lys Trp Gln Thr
2120            2125                2130

Tyr Arg Gly Asn Ser Thr Gly Thr Leu Met Val Phe Phe Gly Asn
2135            2140                2145

Val Asp Ser Ser Gly Ile Lys His Asn Ile Phe Asn Pro Pro Ile
2150            2155                2160

Ile Ala Arg Tyr Ile Arg Leu His Pro Thr His Tyr Ser Ile Arg
2165            2170                2175

Ser Thr Leu Arg Met Glu Leu Met Gly Cys Asp Leu Asn Ser Cys
2180            2185                2190

Ser Met Pro Leu Gly Met Glu Ser Lys Ala Ile Ser Asp Ala Gln
2195            2200                2205

Ile Thr Ala Ser Ser Tyr Phe Thr Asn Met Phe Ala Thr Trp Ser
2210            2215                2220

Pro Ser Lys Ala Arg Leu His Leu Gln Gly Arg Ser Asn Ala Trp
2225            2230                2235

Arg Pro Gln Val Asn Asn Pro Lys Glu Trp Leu Gln Val Asp Phe
2240            2245                2250

Gln Lys Thr Met Lys Val Thr Gly Val Thr Thr Gln Gly Val Lys
2255            2260                2265

Ser Leu Leu Thr Ser Met Tyr Val Lys Glu Phe Leu Ile Ser Ser
2270            2275                2280

Ser Gln Asp Gly His Gln Trp Thr Leu Phe Phe Gln Asn Gly Lys
2285            2290                2295

Val Lys Val Phe Gln Gly Asn Gln Asp Ser Phe Thr Pro Val Val
2300            2305                2310

Asn Ser Leu Asp Pro Pro Leu Leu Thr Arg Tyr Leu Arg Ile His
2315            2320                2325

Pro Gln Ser Trp Val His Gln Ile Ala Leu Arg Met Glu Val Leu
2330            2335                2340

Gly Cys Glu Ala Gln Asp Leu Tyr Asp Lys Thr His Thr Cys Pro
2345            2350                2355

Pro Cys Pro Ala Pro Glu Leu Leu Gly Gly Pro Ser Val Phe Leu
2360            2365                2370

Phe Pro Pro Lys Pro Lys Asp Thr Leu Met Ile Ser Arg Thr Pro
2375            2380                2385

Glu Val Thr Cys Val Val Val Asp Val Ser His Glu Asp Pro Glu
2390            2395                2400

Val Lys Phe Asn Trp Tyr Val Asp Gly Val Glu Val His Asn Ala
2405            2410                2415

Lys Thr Lys Pro Arg Glu Glu Gln Tyr Asn Ser Thr Tyr Arg Val
2420            2425                2430

Val Ser Val Leu Thr Val Leu His Gln Asp Trp Leu Asn Gly Lys
2435            2440                2445

```
Glu Tyr Lys Cys Lys Val Ser Asn Lys Ala Leu Pro Ala Pro Ile
     2450            2455               2460
Glu Lys Thr Ile Ser Lys Ala Lys Gly Gln Pro Arg Glu Pro Gln
 2465            2470                2475
Val Tyr Thr Leu Pro Pro Ser Arg Asp Glu Leu Thr Lys Asn Gln
     2480            2485               2490
Val Ser Leu Thr Cys Leu Val Lys Gly Phe Tyr Pro Ser Asp Ile
 2495            2500                2505
Ala Val Glu Trp Glu Ser Asn Gly Gln Pro Glu Asn Asn Tyr Lys
     2510            2515               2520
Thr Thr Pro Pro Val Leu Asp Ser Asp Gly Ser Phe Phe Leu Tyr
 2525            2530                2535
Ser Lys Leu Thr Val Asp Lys Ser Arg Trp Gln Gln Gly Asn Val
     2540            2545               2550
Phe Ser Cys Ser Val Met His Glu Ala Leu His Asn His Tyr Thr
 2555            2560                2565
Gln Lys Ser Leu Ser Leu Ser Pro Gly Lys
     2570            2575

<210> SEQ ID NO 7
<211> LENGTH: 2958
<212> TYPE: DNA
<213> ORGANISM: Artificial Sequence
<220> FEATURE:
<223> OTHER INFORMATION: Heavy Chain (HC)-Fc
<220> FEATURE:
<221> NAME/KEY: misc_signal
<222> LOCATION: (1)..(57)
<220> FEATURE:
<221> NAME/KEY: misc_feature
<222> LOCATION: (2278)..(2958)
<223> OTHER INFORMATION: Fc region

<400> SEQUENCE: 7
atgcaaatag agctctccac ctgcttcttt ctgtgccttt tgcgattctg ctttagtgcc     60
accagaagat actacctggg tgcagtggaa ctgtcatggg actatatgca agtgatctc    120
ggtgagctgc ctgtggacgc aagatttcct cctagagtgc caaaatcttt tccattcaac    180
acctcagtcg tgtacaaaaa gactctgttt gtagaattca cggatcacct tttcaacatc    240
gctaagccaa ggccacccct gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaagacttt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt cctggaaat ctcgccaata acttttccta ctgctcaaac actcttgatg    960
gaccttggac agtttctact gttttgtcat atctcttccc accaacatga tggcatggaa   1020
gcttatgtca agtagacag ctgtccagag gaaccccaac tacgaatgaa aaataatgaa   1080
```

```
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctcccctt agtcctcgcc    1260 cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttacttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat ggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagagac    2280
aaaactcaca catgcccacc gtgcccagct ccagaactcc tgggcggacc gtcagtcttc    2340
ctcttccccc caaaacccaa ggacaccctc atgatctccc ggaccctga ggtcacatgc    2400 gtggtggtgg acgtgagcca cgaagaccct gaggtcaagt tcaactggta cgtggacggc    2460
gtggaggtgc ataatgccaa gacaaagccg cgggaggagc agtacaacag cacgtaccgt    2520
gtggtcagcg tcctcaccgt cctgcaccag gactggctga atggcaagga gtacaagtgc    2580
aaggtctcca acaaagccct cccagccccc atcgagaaaa ccatctccaa agccaaaggg    2640
cagccccgag aaccacaggt gtacaccctg cccccatccc gggatgagct gaccaagaac    2700
caggtcagcc tgacctgcct ggtcaaaggc ttctatccca gcgacatcgc cgtggagtgg    2760
gagagcaatg ggcagccgga gaacaactac aagaccacgc tcccgtgtt ggactccgac    2820 ggctccttct tcctctacag caagctcacc gtggacaaga gcaggtggca gcagggggaac    2880 gtcttctcat gctccgtgat gcatgaggct ctgcacaacc actacacgca gaagagcctc    2940
tccctgtctc cgggtaaa                                                  2958
```

<210> SEQ ID NO 8
<211> LENGTH: 986
<212> TYPE: PRT
<213> ORGANISM: Artificial Sequence
<220> FEATURE:
<223> OTHER INFORMATION: HC-Fc
<220> FEATURE:
<221> NAME/KEY: SIGNAL
<222> LOCATION: (1)..(19)
<220> FEATURE:
<221> NAME/KEY: mat_peptide
<222> LOCATION: (20)..(986)
<220> FEATURE:

-continued

```
<221> NAME/KEY: MISC_FEATURE
<222> LOCATION: (760)..(986)
<223> OTHER INFORMATION: Fc region

<400> SEQUENCE: 8
```

| | | | | | | | | | | | | | | |
|---|---|---|---|---|---|---|---|---|---|---|---|---|---|---|
| Met | Gln | Ile | Glu | Leu | Ser | Thr | Cys | Phe | Phe | Leu | Cys | Leu | Leu | Arg | Phe |
| 1 | | | | 5 | | | | | 10 | | | | | 15 | |
| Cys | Phe | Ser | Ala | Thr | Arg | Arg | Tyr | Tyr | Leu | Gly | Ala | Val | Glu | Leu | Ser |
| | | | 20 | | | | | 25 | | | | | 30 | | |
| Trp | Asp | Tyr | Met | Gln | Ser | Asp | Leu | Gly | Glu | Leu | Pro | Val | Asp | Ala | Arg |
| | | | 35 | | | | | 40 | | | | | 45 | | |
| Phe | Pro | Pro | Arg | Val | Pro | Lys | Ser | Phe | Pro | Phe | Asn | Thr | Ser | Val | Val |
| 50 | | | | | 55 | | | | | 60 | | | | | |
| Tyr | Lys | Lys | Thr | Leu | Phe | Val | Glu | Phe | Thr | Asp | His | Leu | Phe | Asn | Ile |
| 65 | | | | | 70 | | | | | 75 | | | | | 80 |
| Ala | Lys | Pro | Arg | Pro | Pro | Trp | Met | Gly | Leu | Leu | Gly | Pro | Thr | Ile | Gln |
| | | | | 85 | | | | | 90 | | | | | 95 | |
| Ala | Glu | Val | Tyr | Asp | Thr | Val | Val | Ile | Thr | Leu | Lys | Asn | Met | Ala | Ser |
| | | | 100 | | | | | 105 | | | | | 110 | | |
| His | Pro | Val | Ser | Leu | His | Ala | Val | Gly | Val | Ser | Tyr | Trp | Lys | Ala | Ser |
| | | | 115 | | | | | 120 | | | | | 125 | | |
| Glu | Gly | Ala | Glu | Tyr | Asp | Asp | Gln | Thr | Ser | Gln | Arg | Glu | Lys | Glu | Asp |
| 130 | | | | | 135 | | | | | 140 | | | | | |
| Asp | Lys | Val | Phe | Pro | Gly | Gly | Ser | His | Thr | Tyr | Val | Trp | Gln | Val | Leu |
| 145 | | | | | 150 | | | | | 155 | | | | | 160 |
| Lys | Glu | Asn | Gly | Pro | Met | Ala | Ser | Asp | Pro | Leu | Cys | Leu | Thr | Tyr | Ser |
| | | | | 165 | | | | | 170 | | | | | 175 | |
| Tyr | Leu | Ser | His | Val | Asp | Leu | Val | Lys | Asp | Leu | Asn | Ser | Gly | Leu | Ile |
| | | | 180 | | | | | 185 | | | | | 190 | | |
| Gly | Ala | Leu | Leu | Val | Cys | Arg | Glu | Gly | Ser | Leu | Ala | Lys | Glu | Lys | Thr |
| | | | 195 | | | | | 200 | | | | | 205 | | |
| Gln | Thr | Leu | His | Lys | Phe | Ile | Leu | Leu | Phe | Ala | Val | Phe | Asp | Glu | Gly |
| 210 | | | | | 215 | | | | | 220 | | | | | |
| Lys | Ser | Trp | His | Ser | Glu | Thr | Lys | Asn | Ser | Leu | Met | Gln | Asp | Arg | Asp |
| 225 | | | | | 230 | | | | | 235 | | | | | 240 |
| Ala | Ala | Ser | Ala | Arg | Ala | Trp | Pro | Lys | Met | His | Thr | Val | Asn | Gly | Tyr |
| | | | | 245 | | | | | 250 | | | | | 255 | |
| Val | Asn | Arg | Ser | Leu | Pro | Gly | Leu | Ile | Gly | Cys | His | Arg | Ser | Ser | Val |
| | | | 260 | | | | | 265 | | | | | 270 | | |
| Tyr | Trp | His | Val | Ile | Gly | Met | Gly | Thr | Thr | Pro | Glu | Val | His | Ser | Ile |
| | | | 275 | | | | | 280 | | | | | 285 | | |
| Phe | Leu | Glu | Gly | His | Thr | Phe | Leu | Val | Arg | Asn | His | Arg | Gln | Ala | Ser |
| | | | 290 | | | | | 295 | | | | | 300 | | |
| Leu | Glu | Ile | Ser | Pro | Ile | Thr | Phe | Leu | Thr | Ala | Gln | Thr | Leu | Leu | Met |
| 305 | | | | | 310 | | | | | 315 | | | | | 320 |
| Asp | Leu | Gly | Gln | Phe | Leu | Leu | Phe | Cys | His | Ile | Ser | Ser | His | Gln | His |
| | | | | 325 | | | | | 330 | | | | | 335 | |
| Asp | Gly | Met | Glu | Ala | Tyr | Val | Lys | Val | Asp | Ser | Cys | Pro | Glu | Glu | Pro |
| | | | 340 | | | | | 345 | | | | | 350 | | |
| Gln | Leu | Arg | Met | Lys | Asn | Asn | Glu | Glu | Ala | Glu | Asp | Tyr | Asp | Asp | Asp |
| | | | 355 | | | | | 360 | | | | | 365 | | |
| Leu | Thr | Asp | Ser | Glu | Met | Asp | Val | Val | Arg | Phe | Asp | Asp | Asp | Asn | Ser |
| | | | 370 | | | | | 375 | | | | | 380 | | |
| Pro | Ser | Phe | Ile | Gln | Ile | Arg | Ser | Val | Ala | Lys | Lys | His | Pro | Lys | Thr |

```
            385                 390                 395                 400
Trp Val His Tyr Ile Ala Ala Glu Glu Asp Trp Asp Tyr Ala Pro
                    405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Ser Tyr Lys Lys Val Arg Phe Met
                435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Asp Lys Thr His Thr Cys Pro Pro Cys
            755                 760                 765

Pro Ala Pro Glu Leu Leu Gly Gly Pro Ser Val Phe Leu Phe Pro Pro
        770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815
```

```
Tyr Val Asp Gly Val Glu Val His Asn Ala Lys Thr Lys Pro Arg Glu
            820                 825                 830
Glu Gln Tyr Asn Ser Thr Tyr Arg Val Val Ser Val Leu Thr Val Leu
        835                 840                 845
His Gln Asp Trp Leu Asn Gly Lys Glu Tyr Lys Cys Lys Val Ser Asn
850                 855                 860
Lys Ala Leu Pro Ala Pro Ile Glu Lys Thr Ile Ser Lys Ala Lys Gly
865                 870                 875                 880
Gln Pro Arg Glu Pro Gln Val Tyr Thr Leu Pro Pro Ser Arg Asp Glu
                885                 890                 895
Leu Thr Lys Asn Gln Val Ser Leu Thr Cys Leu Val Lys Gly Phe Tyr
            900                 905                 910
Pro Ser Asp Ile Ala Val Glu Trp Glu Ser Asn Gly Gln Pro Glu Asn
        915                 920                 925
Asn Tyr Lys Thr Thr Pro Pro Val Leu Asp Ser Asp Gly Ser Phe Phe
    930                 935                 940
Leu Tyr Ser Lys Leu Thr Val Asp Lys Ser Arg Trp Gln Gln Gly Asn
945                 950                 955                 960
Val Phe Ser Cys Ser Val Met His Glu Ala Leu His Asn His Tyr Thr
                965                 970                 975
Gln Lys Ser Leu Ser Leu Ser Pro Gly Lys
            980                 985

<210> SEQ ID NO 9
<211> LENGTH: 2973
<212> TYPE: DNA
<213> ORGANISM: Artificial Sequence
<220> FEATURE:
<223> OTHER INFORMATION: Heavy Chain (HC)-Fc (5 amino acid linker
      between HC and Fc)
<220> FEATURE:
<221> NAME/KEY: misc_signal
<222> LOCATION: (1)..(57)
<220> FEATURE:
<221> NAME/KEY: misc_feature
<222> LOCATION: (2278)..(2292)
<223> OTHER INFORMATION: 5 amino acid linker
<220> FEATURE:
<221> NAME/KEY: misc_feature
<222> LOCATION: (2293)..(2973)
<223> OTHER INFORMATION: Fc region

<400> SEQUENCE: 9
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatctttt ccattcaac      180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
```

```
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aaccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcccct agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga atgacaaaac tcacacatgc ccaccgtgcc cagctccaga actcctgggc   2340
ggaccgtcag tcttcctctt ccccccaaaa cccaaggaca ccctcatgat ctcccggacc   2400
cctgaggtca catgcgtggt ggtggacgtg agccacgaag accctgaggt caagttcaac   2460
tggtacgtgg acggcgtgga ggtgcataat gccaagacaa agccgcggga ggagcagtac   2520
aacagcacgt accgtgtggt cagcgtcctc accgtcctgc accaggactg gctgaatggc   2580
aaggagtaca gtgcaaggt ctccaacaaa gccctcccag ccccatcga gaaaaccatc     2640 tccaaagcca aagggcagcc ccgagaacca caggtgtaca ccctgccccc atcccgggat   2700
gagctgacca agaaccaggt cagcctgacc tgcctggtca aaggcttcta tcccagcgac   2760
atcgccgtgg agtgggagag caatgggcag ccggagaaca actacaagac cacgcctccc   2820
gtgttggact ccgacggctc cttcttcctc tacagcaagc tcaccgtgga caagagcagg   2880
tggcagcagg ggaacgtctt ctcatgctcc gtgatgcatg aggctctgca caaccactac   2940
acgcagaaga gcctctccct gtctccgggt aaa                                 2973
```

<210> SEQ ID NO 10

```
<211> LENGTH: 991
<212> TYPE: PRT
<213> ORGANISM: Artificial Sequence
<220> FEATURE:
<223> OTHER INFORMATION: HC+5-Fc
<220> FEATURE:
<221> NAME/KEY: SIGNAL
<222> LOCATION: (1)..(19)
<220> FEATURE:
<221> NAME/KEY: mat_peptide
<222> LOCATION: (20)..(991)
<220> FEATURE:
<221> NAME/KEY: MISC_FEATURE
<222> LOCATION: (760)..(764)
<223> OTHER INFORMATION: B domain
<220> FEATURE:
<221> NAME/KEY: MISC_FEATURE
<222> LOCATION: (765)..(991)
<223> OTHER INFORMATION: Fc region

<400> SEQUENCE: 10
```

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Ser Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

```
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Ser Tyr Lys Lys Val Arg Phe Met
            435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
        690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
```

```
                    725                 730                 735
Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Asp Lys Thr His
            755                 760                 765

Thr Cys Pro Pro Cys Pro Ala Pro Glu Leu Leu Gly Gly Pro Ser Val
770                 775                 780

Phe Leu Phe Pro Pro Lys Pro Lys Asp Thr Leu Met Ile Ser Arg Thr
785                 790                 795                 800

Pro Glu Val Thr Cys Val Val Val Asp Val Ser His Glu Asp Pro Glu
                805                 810                 815

Val Lys Phe Asn Trp Tyr Val Asp Gly Val Glu Val His Asn Ala Lys
                820                 825                 830

Thr Lys Pro Arg Glu Glu Gln Tyr Asn Ser Thr Tyr Arg Val Val Ser
                835                 840                 845

Val Leu Thr Val Leu His Gln Asp Trp Leu Asn Gly Lys Glu Tyr Lys
            850                 855                 860

Cys Lys Val Ser Asn Lys Ala Leu Pro Ala Pro Ile Glu Lys Thr Ile
865                 870                 875                 880

Ser Lys Ala Lys Gly Gln Pro Arg Glu Pro Gln Val Tyr Thr Leu Pro
                885                 890                 895

Pro Ser Arg Asp Glu Leu Thr Lys Asn Gln Val Ser Leu Thr Cys Leu
                900                 905                 910

Val Lys Gly Phe Tyr Pro Ser Asp Ile Ala Val Glu Trp Glu Ser Asn
            915                 920                 925

Gly Gln Pro Glu Asn Asn Tyr Lys Thr Thr Pro Pro Val Leu Asp Ser
        930                 935                 940

Asp Gly Ser Phe Phe Leu Tyr Ser Lys Leu Thr Val Asp Lys Ser Arg
945                 950                 955                 960

Trp Gln Gln Gly Asn Val Phe Ser Cys Ser Val Met His Glu Ala Leu
                965                 970                 975

His Asn His Tyr Thr Gln Lys Ser Leu Ser Leu Ser Pro Gly Lys
            980                 985                 990

<210> SEQ ID NO 11
<211> LENGTH: 2793
<212> TYPE: DNA
<213> ORGANISM: Artificial Sequence
<220> FEATURE:
<223> OTHER INFORMATION: Light Chain (LC)-Fc
<220> FEATURE:
<221> NAME/KEY: misc_signal
<222> LOCATION: (1)..(60)
<220> FEATURE:
<221> NAME/KEY: misc_feature
<222> LOCATION: (2113)..(2793)
<223> OTHER INFORMATION: Fc region

<400> SEQUENCE: 11
atggagacag acacactcct gctatgggta ctgctgctct gggttccagg ttccactggt    60
gaaataactc gtactactct tcagtcagat caagaggaaa ttgactatga tgataccata   120
tcagttgaaa tgaagaagga agattttgac atttatgatg aggatgaaaa tcagagcccc   180
cgcagctttc aaaagaaaac acgacactat tttattgctg cagtggagag gctctgggat   240
tatgggatga gtagctcccc acatgttcta agaaacaggg ctcagagtgg cagtgtccct   300
cagttcaaga agttgttttt ccaggaattt actgatggct cctttactca gcccttatac   360
```

```
cgtggagaac taaatgaaca tttgggactc ctggggccat atataagagc agaagttgaa    420
gataatatca tggtaacttt cagaaatcag gcctctcgtc cctattcctt ctattctagc    480
cttatttctt atgaggaaga tcagaggcaa ggagcagaac ctagaaaaaa ctttgtcaag    540
cctaatgaaa ccaaaactta cttttggaaa gtgcaacatc atatggcacc cactaaagat    600
gagtttgact gcaaagcctg gcttatttc tctgatgttg acctggaaaa agatgtgcac     660
tcaggcctga ttggacccct tctggtctgc cacactaaca cactgaaccc tgctcatggg    720
agacaagtga cagtacagga atttgctctg ttttcacca tctttgatga gaccaaaagc     780
tggtacttca ctgaaaatat ggaaagaaac tgcagggctc cctgcaatat ccagatggaa    840
gatcccactt ttaaagagaa ttatcgcttc catgcaatca atggctacat aatggataca    900
ctacctggct tagtaatggc tcaggatcaa aggattcgat ggtatctgct cagcatgggc    960
agcaatgaaa acatccattc tattcatttc agtggacatg tgttcactgt acgaaaaaaa   1020
gaggagtata aaatggcact gtacaatctc tatccaggtg tttttgagac agtggaaatg   1080
ttaccatcca aagctggaat ttggcgggtg gaatgcctta ttggcgagca tctacatgct   1140
gggatgagca cactttttct ggtgtacagc aataagtgtc agactcccct gggaatggct   1200
tctggacaca ttagagattt tcagattaca gcttcaggac aatatggaca gtgggcccca   1260
aagctggcca gacttcatta ttccggatca atcaatgcct ggagcaccaa ggagcccttt   1320
tcttggatca aggtggatct gttggcacca atgattattc acggcatcaa gacccagggt   1380
gcccgtcaga agttctccag cctctacatc tctcagttta tcatcatgta tagtcttgat   1440
gggaagaagt ggcagactta cgaggaaat tccactggaa ccttaatggt cttctttggc    1500
aatgtggatt catctgggat aaaacacaat attttaacc ctccaattat tgctcgatac     1560
atccgtttgc acccaactca ttatagcatt cgcagcactc ttcgcatgga gttgatgggc   1620
tgtgatttaa atagttgcag catgccattg gaatggagaa gtaaagcaat atcagatgca   1680
cagattactg cttcatccta ctttaccaat atgtttgcca cctggtctcc ttcaaaagct   1740
cgacttcacc tccaagggag gagtaatgcc tggagacctc aggtgaataa tccaaaagag   1800
tggctgcaag tggacttcca gaagacaatg aaagtcacag gagtaactac tcagggagta   1860
aaatctctgc ttaccagcat gtatgtgaag gagttcctca tctccagcag tcaagatggc   1920
catcagtgga ctctcttttt tcagaatggc aaagtaaagg tttttcaggg aaatcaagac   1980
tccttcacac ctgtggtgaa ctctctagac ccaccgttac tgactcgcta ccttcgaatt   2040 caccccccaga gttgggtgca ccagattgcc ctgaggatgg aggttctggg ctgcgaggca   2100
caggacctct acgacaaaac tcacacatgc ccaccgtgcc cagctccaga actcctgggc   2160
ggaccgtcag tcttcctctt ccccccaaaa cccaaggaca ccctcatgat ctcccggacc   2220
cctgaggtca catgcgtggt ggtggacgtg agccacgaag accctgaggt caagttcaac   2280
tggtacgtgg acggcgtgga ggtgcataat gccaagacaa agccgcggga ggagcagtac   2340
aacagcacgt accgtgtggt cagcgtcctc accgtcctgc accaggactg gctgaatggc   2400
aaggagtaca agtgcaaggt ctccaacaaa gccctcccag cccccatcga gaaaaccatc   2460
tccaaagcca aagggcagcc ccgagaacca caggtgtaca ccctgccccc atcccgggat   2520
gagctgacca agaaccaggt cagcctgacc tgcctggtca aaggcttcta tcccagcgac   2580
atcgccgtgg agtgggagag caatgggcag ccggagaaca actacaagac cacgcctccc   2640
gtgttggact ccgacggctc cttcttcctc tacagcaagc tcaccgtgga caagagcagg   2700
tggcagcagg ggaacgtctt ctcatgctcc gtgatgcatg aggctctgca caaccactac   2760
```
acgcagaaga gcctctccct gtctccgggt aaa                                          2793

<210> SEQ ID NO 12
<211> LENGTH: 931
<212> TYPE: PRT
<213> ORGANISM: Artificial Sequence
<220> FEATURE:
<223> OTHER INFORMATION: LC-Fc6His
<220> FEATURE:
<221> NAME/KEY: SIGNAL
<222> LOCATION: (1)..(20)
<220> FEATURE:
<221> NAME/KEY: mat_peptide
<222> LOCATION: (21)..(931)
<220> FEATURE:
<221> NAME/KEY: MISC_FEATURE
<222> LOCATION: (705)..(931)
<223> OTHER INFORMATION: Fc region

<400> SEQUENCE: 12

```
Met Glu Thr Asp Thr Leu Leu Leu Trp Val Leu Leu Trp Val Pro
1               5                   10                  15

Gly Ser Thr Gly Glu Ile Thr Arg Thr Thr Leu Gln Ser Asp Gln Glu
            20                  25                  30

Glu Ile Asp Tyr Asp Asp Thr Ile Ser Val Glu Met Lys Lys Glu Asp
            35                  40                  45

Phe Asp Ile Tyr Asp Glu Asp Glu Asn Gln Ser Pro Arg Ser Phe Gln
    50                  55                  60

Lys Lys Thr Arg His Tyr Phe Ile Ala Ala Val Glu Arg Leu Trp Asp
65                  70                  75                  80

Tyr Gly Met Ser Ser Ser Pro His Val Leu Arg Asn Arg Ala Gln Ser
                85                  90                  95

Gly Ser Val Pro Gln Phe Lys Lys Val Val Phe Gln Glu Phe Thr Asp
            100                 105                 110

Gly Ser Phe Thr Gln Pro Leu Tyr Arg Gly Glu Leu Asn Glu His Leu
        115                 120                 125

Gly Leu Leu Gly Pro Tyr Ile Arg Ala Glu Val Glu Asp Asn Ile Met
    130                 135                 140

Val Thr Phe Arg Asn Gln Ala Ser Arg Pro Tyr Ser Phe Tyr Ser Ser
145                 150                 155                 160

Leu Ile Ser Tyr Glu Glu Asp Gln Arg Gln Gly Ala Glu Pro Arg Ser
                165                 170                 175

Asn Phe Val Lys Pro Asn Glu Thr Lys Thr Tyr Phe Trp Lys Val Gln
            180                 185                 190

His His Met Ala Pro Thr Lys Asp Glu Phe Asp Cys Lys Ala Trp Ala
        195                 200                 205

Tyr Phe Ser Asp Val Asp Leu Glu Lys Asp Val His Ser Gly Leu Ile
    210                 215                 220

Gly Pro Leu Leu Val Cys His Thr Asn Thr Leu Asn Pro Ala His Gly
225                 230                 235                 240

Arg Gln Val Thr Val Gln Glu Phe Ala Leu Phe Phe Thr Ile Phe Asp
                245                 250                 255

Glu Thr Lys Ser Trp Tyr Phe Thr Glu Asn Met Glu Arg Asn Cys Arg
            260                 265                 270

Ala Pro Cys Asn Ile Gln Met Glu Asp Pro Thr Phe Lys Glu Asn Tyr
        275                 280                 285

Arg Phe His Ala Ile Asn Gly Tyr Ile Met Asp Thr Leu Pro Gly Leu
    290                 295                 300
```

```
Val Met Ala Gln Asp Gln Arg Ile Arg Trp Tyr Leu Leu Ser Met Gly
305                 310                 315                 320

Ser Asn Glu Asn Ile His Ser Ile His Phe Ser Gly His Val Phe Thr
                325                 330                 335

Val Arg Ser Lys Glu Glu Tyr Lys Met Ala Leu Tyr Asn Leu Tyr Pro
                340                 345                 350

Gly Val Phe Glu Thr Val Glu Met Leu Pro Ser Lys Ala Gly Ile Trp
                355                 360                 365

Arg Val Glu Cys Leu Ile Gly Glu His Leu His Ala Gly Met Ser Thr
370                 375                 380

Leu Phe Leu Val Tyr Ser Asn Lys Cys Gln Thr Pro Leu Gly Met Ala
385                 390                 395                 400

Ser Gly His Ile Arg Asp Phe Gln Ile Thr Ala Ser Gly Gln Tyr Gly
                405                 410                 415

Gln Trp Ala Pro Lys Leu Ala Arg Leu His Tyr Ser Gly Ser Ile Asn
                420                 425                 430

Ala Trp Ser Thr Lys Glu Pro Phe Ser Trp Ile Lys Val Asp Leu Leu
                435                 440                 445

Ala Pro Met Ile Ile His Gly Ile Lys Thr Gln Gly Ala Arg Gln Lys
450                 455                 460

Phe Ser Ser Leu Tyr Ile Ser Gln Phe Ile Ile Met Tyr Ser Leu Asp
465                 470                 475                 480

Gly Lys Lys Trp Gln Thr Tyr Arg Gly Asn Ser Thr Gly Thr Leu Met
                485                 490                 495

Val Phe Phe Gly Asn Val Asp Ser Ser Gly Ile Lys His Asn Ile Phe
                500                 505                 510

Asn Pro Pro Ile Ile Ala Arg Tyr Ile Arg Leu His Pro Thr His Tyr
                515                 520                 525

Ser Ile Arg Ser Thr Leu Arg Met Glu Leu Met Gly Cys Asp Leu Asn
530                 535                 540

Ser Cys Ser Met Pro Leu Gly Met Glu Ser Lys Ala Ile Ser Asp Ala
545                 550                 555                 560

Gln Ile Thr Ala Ser Ser Tyr Phe Thr Asn Met Phe Ala Thr Trp Ser
                565                 570                 575

Pro Ser Lys Ala Arg Leu His Leu Gln Gly Arg Ser Asn Ala Trp Arg
                580                 585                 590

Pro Gln Val Asn Asn Pro Lys Glu Trp Leu Gln Val Asp Phe Gln Lys
                595                 600                 605

Thr Met Lys Val Thr Gly Val Thr Thr Gln Gly Val Lys Ser Leu Leu
                610                 615                 620

Thr Ser Met Tyr Val Lys Glu Phe Leu Ile Ser Ser Ser Gln Asp Gly
625                 630                 635                 640

His Gln Trp Thr Leu Phe Phe Gln Asn Gly Lys Val Lys Val Phe Gln
                645                 650                 655

Gly Asn Gln Asp Ser Phe Thr Pro Val Val Asn Ser Leu Asp Pro Pro
                660                 665                 670

Leu Leu Thr Arg Tyr Leu Arg Ile His Pro Gln Ser Trp Val His Gln
                675                 680                 685

Ile Ala Leu Arg Met Glu Val Leu Gly Cys Glu Ala Gln Asp Leu Tyr
                690                 695                 700

Asp Lys Thr His Thr Cys Pro Pro Cys Pro Ala Pro Glu Leu Leu Gly
705                 710                 715                 720
```

-continued

```
Gly Pro Ser Val Phe Leu Phe Pro Pro Lys Pro Lys Asp Thr Leu Met
                725                 730                 735

Ile Ser Arg Thr Pro Glu Val Thr Cys Val Val Val Asp Val Ser His
            740                 745                 750

Glu Asp Pro Glu Val Lys Phe Asn Trp Tyr Val Asp Gly Val Glu Val
        755                 760                 765

His Asn Ala Lys Thr Lys Pro Arg Glu Glu Gln Tyr Asn Ser Thr Tyr
    770                 775                 780

Arg Val Val Ser Val Leu Thr Val Leu His Gln Asp Trp Leu Asn Gly
785                 790                 795                 800

Lys Glu Tyr Lys Cys Lys Val Ser Asn Lys Ala Leu Pro Ala Pro Ile
                805                 810                 815

Glu Lys Thr Ile Ser Lys Ala Lys Gly Gln Pro Arg Glu Pro Gln Val
            820                 825                 830

Tyr Thr Leu Pro Pro Ser Arg Asp Glu Leu Thr Lys Asn Gln Val Ser
        835                 840                 845

Leu Thr Cys Leu Val Lys Gly Phe Tyr Pro Ser Asp Ile Ala Val Glu
    850                 855                 860

Trp Glu Ser Asn Gly Gln Pro Glu Asn Asn Tyr Lys Thr Thr Pro Pro
865                 870                 875                 880

Val Leu Asp Ser Asp Gly Ser Phe Phe Leu Tyr Ser Lys Leu Thr Val
                885                 890                 895

Asp Lys Ser Arg Trp Gln Gln Gly Asn Val Phe Ser Cys Ser Val Met
            900                 905                 910

His Glu Ala Leu His Asn His Tyr Thr Gln Lys Ser Leu Ser Leu Ser
        915                 920                 925

Pro Gly Lys
    930
```

FACTOR VIII-FC CHIMERIC AND HYBRID POLYPEPTIDES, AND METHODS OF USE THEREOF

REFERENCE TO EARLIER FILED APPLICATIONS

This application is a continuation of U.S. patent application Ser. No. 14/964,289, filed Dec. 9, 2015, which is a division of U.S. patent application Ser. No. 13/793,783, filed Mar. 11, 2013, now U.S. Pat. No. 9,241,978, which is a division of U.S. patent application Ser. No. 13/513,424, filed Dec. 28, 2012, now U.S. Pat. No. 9,050,318, which is a 35 U.S.C. § 371 filing of International Patent Application No. PCT/US2010/059136, filed Dec. 6, 2010, which claims the benefit of U.S. Provisional Application No. 61/267,070, filed Dec. 6, 2009, U.S. Provisional Application No. 61/285,054, filed Dec. 9, 2009, U.S. Provisional Application No. 61/301,592, filed Feb. 4, 2010, U.S. Provisional Application No. 61/363,065, filed Jul. 9, 2010, U.S. Provisional Application No. 61/373,113, filed Aug. 12, 2010, U.S. Provisional Application No. 61/410,929, filed Nov. 7, 2010, and U.S. Provisional Application No. 61/419,676, filed Dec. 3, 2010, all of which are incorporated herein by reference in their entireties.

REFERENCE TO SEQUENCE LISTING SUBMITTED ELECTRONICALLY VIA EFS-WEB

The content of the electronically submitted sequence listing (Name: 610439_SA9-408USDV2CON_Sequence_Listing.txt, Size: 97,677 bytes; and Date of Creation: Feb. 7, 2019) submitted in this application is incorporated herein by reference in its entirety.

BACKGROUND OF THE INVENTION

Field of the Invention

The present invention relates generally to the field of therapeutics for hemostatic disorders.

Background Art

Hemophilia A is an X-linked bleeding disorder caused by mutations and/or deletions in the factor VIII (FVIII) gene resulting in a deficiency of FVIII activity (Peyvandi et al. 2006). The disease is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., Semin. Thromb. Hemost. 29:87-96 (2003), which is herein incorporated by reference in its entirety).

The A2 domain is necessary for the procoagulant activity of the factor VIII molecule. Studies show that porcine factor VIII has six-fold greater procoagulant activity than human factor VIII (Lollar, P., and E. T. Parker, J. Biol. Chem. 266:12481-12486 (1991)), and that the difference in coagulant activity between human and porcine factor VIII appears to be based on a difference in amino acid sequence between one or more residues in the human and porcine A2 domains (Lollar, P., et al., J. Biol. Chem. 267:23652-23657 (1992)), incorporated herein by reference in its entirety.

Treatment of hemophilia A is by replacement therapy targeting restoration of FVIII activity to 1 to 5% of normal levels to prevent spontaneous bleeding (Mannucci, P. M., et al., N. Engl. J. Med. 344:1773-1779 (2001), which is herein incorporated by reference in its entirety). There are plasma-derived and recombinant FVIII products available to treat bleeding episodes on-demand or to prevent bleeding episodes from occurring by treating prophylactically. Based on the half-life of these products treatment regimens require frequent intravenous administration. Such frequent administration is painful and inconvenient.

Reduced mortality, prevention of joint damage and improved quality of life have been important achievements due to the development of plasma-derived and recombinant FVIII. Prolonged protection from bleeding would represent another key advancement in the treatment of hemophilia A patients. However, to date, no products that allow for prolonged protection have been developed. Therefore, there remains a need for improved methods of treating hemophilia due to factor VIII deficiency that are more tolerable and more effective than current therapies.

BRIEF SUMMARY OF THE INVENTION

The present invention provides methods of administering Factor VIII; methods of administering chimeric polypeptides comprising Factor VIII and hybrids of such chimeric polypeptides; chimeric polypeptides comprising Factor VIII and hybrids of such chimeric polypeptides; polynucleotides encoding such chimeric and hybrid polypeptides; cells comprising such polynucleotides: and methods of producing such chimeric and hybrid polypeptides using such cells.

The present invention provides a method of administering Factor VIII to a subject in need thereof, comprising administering to the subject a therapeutic dose of a chimeric Factor VIII polypeptide, e.g., a chimeric Factor VIII-Fc polypeptide, at a dosing interval at least about one and one-half times longer than the dosing interval required for an equivalent amount of said Factor VIII without the non-Factor VIII portion (a polypeptide consisting of said Factor VIII portion), e.g., without the Fc portion.

The dosing interval may be at least about one and one-half to six times longer, one and one-half to five times longer, one and one-half to four times longer, one and one-half to three times longer, or one and one-half to two times longer, than the dosing interval required for an equivalent amount of said Factor VIII without the non-Factor VIII portion (a polypeptide consisting of said Factor VIII portion), e.g., the Fc portion. The dosing interval may be at least about one and one-half, two, two and one-half, three, three and one-half, four, four and one-half, five, five and one-half or six times longer than the dosing interval required for an equivalent amount of said Factor VIII without the non-Factor VIII portion (a polypeptide consisting of said Factor VIII portion), e.g., the Fc portion. The dosing interval may be about every five, six, seven, eight, nine, ten, eleven, twelve, thirteen, or fourteen days or longer.

The dosing interval may be at least about one and one-half to 5, one and one-half, 2, 3, 4, or 5 days or longer.

The present invention also provides a method of administering Factor VIII to a subject in need thereof, comprising administering to the subject a therapeutic dose of a chimeric Factor VIII polypeptide, e.g., a chimeric Factor VIII-Fc polypeptide, to obtain an area under the plasma concentration versus time curve (AUC) at least about one and one-quarter times greater than the AUC obtained by an equivalent amount of said Factor VIII without the non-Factor VIII portion (a polypeptide consisting of said Factor VIII portion), e.g., without the Fc portion.

The present invention also provides a method of administering Factor VIII to a subject in need thereof, comprising administering to the subject a therapeutic dose of a polypeptide comprising a Factor VIII and an Fc at a dosing interval of about every five, six, seven, eight, nine, ten, eleven, twelve, thirteen, or fourteen days or longer.

The methods of the invention may be practiced on a subject in need of prophylactic treatment or on-demand treatment.

On-demand treatment includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal hemiotomy, synovectomy, total knee replacement, craniotomy, osteosynthesis, trauma surgery, intracranial surgery, intra-abdominal surgery., intrathoracic surgery, or joint replacement surgery.

For on-demand treatment, the dosing interval of said chimeric polypeptide is about once every 24-36, 24-48, 24-72, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

The therapeutic doses that may be used in the methods of the invention are about 10 to about 100 IU/kg, more specifically, about 10-20, 20-30, 30-40, 40-50, 50-60, 60-70, 70-80, 80-90, or 90-100 IU/kg, and more specifically, about 10, 15, 20, 25, 30, 35, 40, 45, 50, 55, 60, 65, 70, 75, 80, 85, 90, 95, or 100 IU/kg.

The therapeutic doses that may be used in the methods of the invention are about 10 to about 150 IU/kg, more specifically, about 100-110, 110-120, 120-130, 130-140, 140-150 IU/kg, and more specifically, about 110, 115, 120, 125, 130, 135, 140, 145, or 150 IU/kg.

The subject in the methods of the invention may be a human subject or may be a non-human mammal. Non-human mammals include, e.g., mice, dogs, primates, monkeys, cats, horses, cows, pigs, and other domestic animals and small animals. The determination of dosing interval and AUC may be carried out in a single subject or in a population of subjects.

The Factor VIII (or Factor VIII portion of a chimeric polypeptide) may be a human Factor VIII, or a non-human Factor VIII, such as porcine, mouse or canine factor VIII. The Factor VIII (or Factor VIII portion of a chimeric polypeptide) may have a full or partial deletion of the B domain.

The Factor VIII (or Factor VIII portion of a chimeric polypeptide) may be at least 90% or 95% identical to a Factor VIII amino acid sequence shown in Table 2 without a signal sequence (amino acids 1 to 1438 of SEQ ID NO:2: amino acids 1 to 2332 of SEQ ID NO:6: amino acids 1 to 740 of SEQ ID NO:8; amino acids 1 to 745 of SEQ ID NO:10; or amino acids 1 to 684 of SEQ ID NO:12). The Factor VIII (or Factor VIII portion of a chimeric polypeptide) may be identical to a Factor VIII amino acid sequence shown in Table 2 without a signal sequence (amino acids 1 to 1438 of SEQ ID NO:2: amino acids 1 to 2332 of SEQ ID NO:6: amino acids 1 to 740 of SEQ ID NO:8: amino acids 1 to 745 of SEQ ID NO: 10; or amino acids 1 to 684 of SEQ ID NO: 12).

The Factor VIII (or Factor VIII portion of a chimeric polypeptide) may be at least 90% or 95% identical to a Factor VIII amino acid sequence shown in Table 2 with a signal sequence (amino acids −19 to 1438 of SEQ ID NO:2; amino acids −19 to 2332 of SEQ ID NO:6: amino acids −19 to 740 of SEQ ID NO:8: amino acids −19 to 745 of SEQ ID NO: 10; or amino acids −20 to 684 of SEQ ID NO: 12). The Factor VIII (or Factor VIII portion of a chimeric polypeptide) may be identical to a Factor VIII amino acid sequence shown in Table 2 with a signal sequence (amino acids −19 to 1438 of SEQ ID NO:2; amino acids −19 to 2332 of SEQ ID NO:6: amino acids −19 to 740 of SEQ ID NO:8: amino acids −19 to 745 of SEQ ID NO:10; or amino acids −20 to 684 of SEQ ID NO: 12).

The Fc portion (or Fc portion of a chimeric polypeptide) may be at least 90% or 95% identical to the Fc amino acid sequence shown in Table 2 (amino acids 1439 to 1665 of SEQ ID NO:2; amino acids 2333 to 2559 of SEQ ID NO:6: amino acids 741 to 967 of SEQ ID NO:8; amino acids 746 to 972 of SEQ ID NO: 10; amino acids 685 to 924 of SEQ ID NO: 12). The Fc portion (or Fc portion of a chimeric polypeptide) may be identical to the Fc amino acid sequence shown in Table 2 (amino acids 1439 to 1665 of SEQ ID NO:2; amino acids 2333 to 2559 of SEQ ID NO:6; amino acids 741 to 967 of SEQ ID NO:8; amino acids 746 to 972 of SEQ ID NO:10; amino acids 685 to 924 of SEQ ID NO:12).

The chimeric polypeptide may comprise a sequence at least 90% or 95% identical to the Factor VIII and Fc amino acid sequence shown in Table 2A(i) without a signal sequence (amino acids 1 to 1665 of SEQ ID NO:2) or at least 90% or 95% identical to the Factor VIII and Fc amino acid sequence shown in Table 2A(i) with a signal sequence (amino acids −19 to 1665 of SEQ ID NO:2). The chimeric polypeptide may comprise a sequence identical to the Factor VIII and Fc amino acid sequence shown in Table 2A(i) without a signal sequence (amino acids 1 to 1665 of SEQ ID NO:2) or identical to the Factor VIII and Fc amino acid sequence shown in Table 2A(i) with a signal sequence (amino acids −19 to 1665 of SEQ ID NO:2).

The chimeric polypeptide may be in the form of a hybrid comprising a second polypeptide in association with said chimeric polypeptide, wherein said second polypeptide comprises or consists essentially of an Fc.

The second polypeptide may comprise or consist essentially of a sequence at least 90% or 95% identical to the amino acid sequence shown in Table 2A(ii) without a signal sequence (amino acids 1 to 227 of SEQ ID NO:4) or at least 90% or 95% identical to the amino acid sequence shown in Table 2A(ii) with a signal sequence (amino acids −20 to 227 of SEQ ID NO:4). The second polypeptide may comprise or consist essentially of a sequence identical to the amino acid sequence shown in Table 2A(ii) without a signal sequence (amino acids 1 to 227 of SEQ ID NO:4) or identical to the amino acid sequence shown in Table 2A(ii) with a signal sequence (amino acids −20 to 227 of SEQ ID NO:4).

The chimeric polypeptide or hybrid may be administered as part of a pharmaceutical composition comprising at least one excipient.

The invention also provides the above-described chimeric and hybrid polypeptides themselves, polynucleotides encoding them, a cultured human embryonic cells comprising the polynucleotides, and methods of producing such chimeric and hybrid polypeptides, and the polypeptides produced by such methods.

BRIEF DESCRIPTION OF THE DRAWINGS/FIGURES

FIG. 1. Schematic Representation of rFVIIIFc monomer.

Figure 2:
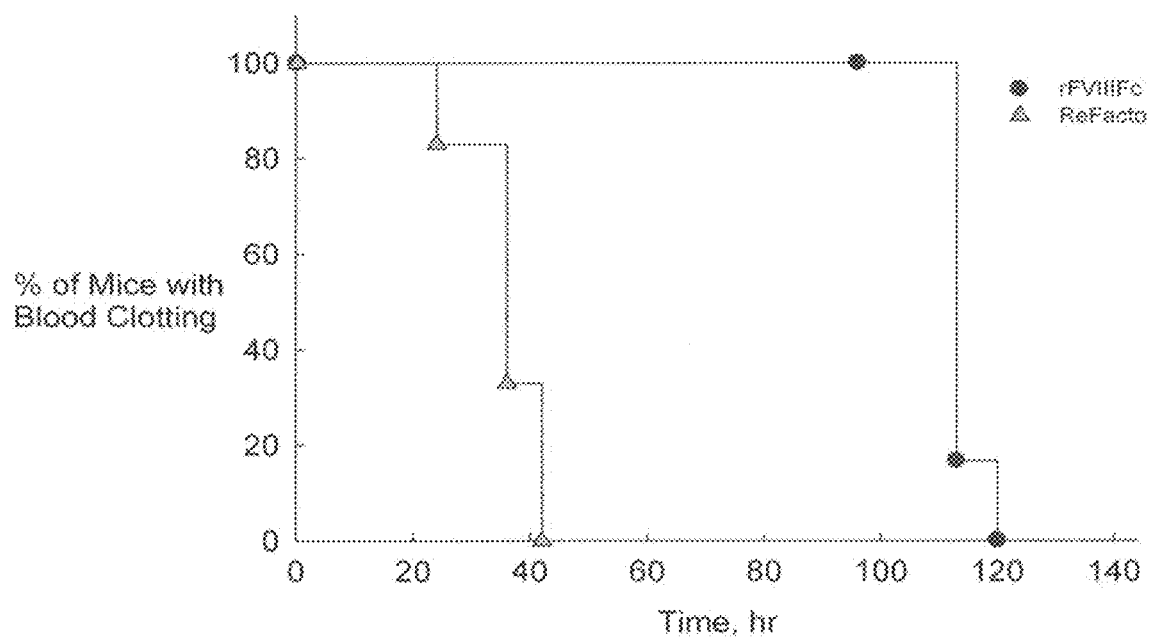

FIG. 2. WBCT of rFVIIIFc compared to REFACTO® in hemophilia A mice after a 50 IU/kg intravenous dose (n=6 mice per group).

Figure 3:
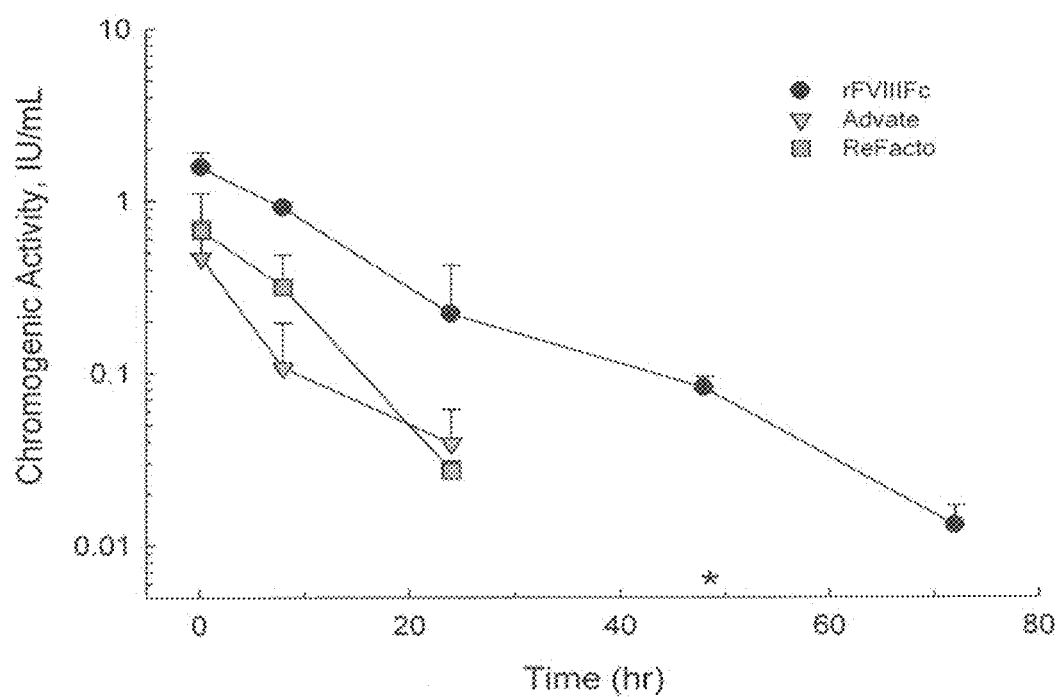

FIG. 3. Chromogenic Activity in Plasma from hemophilia A mice after a single IV dose of 50 IU/kg rFVIIIFc, REFACTO® and ADVATE®.

Figure 4A:
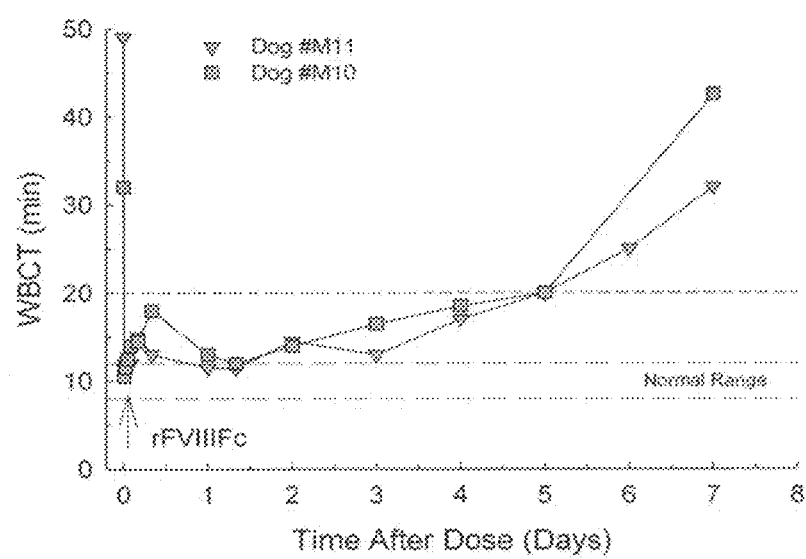

FIG. 4A. WBCT of rFVIIIFc in hemophilia A dogs.

FIG. 4B. WBCT of REFACTO® in hemophilia A dogs followed by rFVIIIFc in a Crossover Study.

Figure 5:
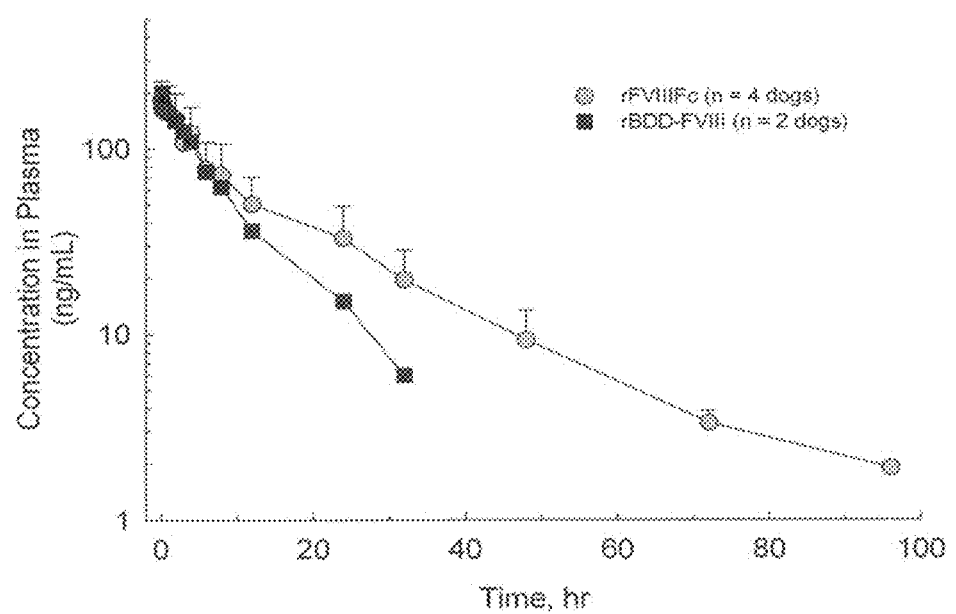

FIG. 5. Pharmacokinetics of intravenous rFVIIIFc and REFACTO® in Hemophilia A Dogs (measured by ELISA).

Figure 6:
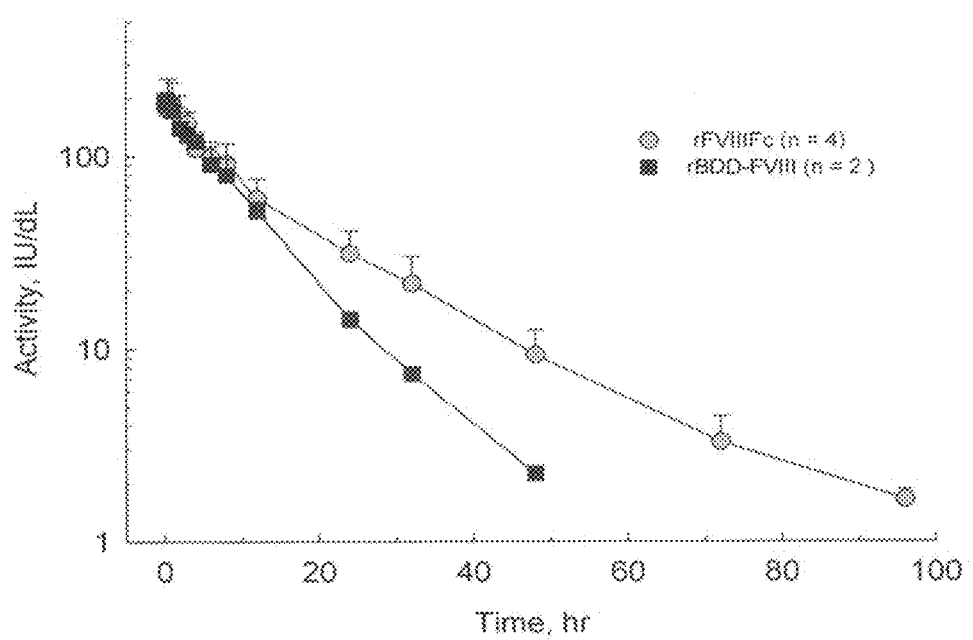

FIG. 6. Activity of rFVIII and REFACTO® after a single intravenous dose in hemophilia A dogs (measured by FVIII-specific chromogenic activity assay).

Figure 7:
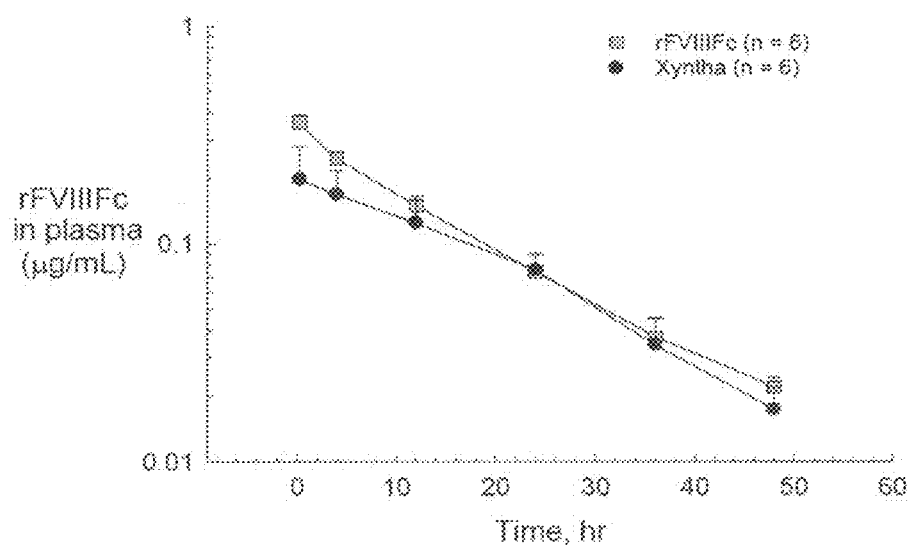

FIG. 7. Group mean plasma concentration over time of rFVIIIFc and XYNTHA® after a single intravenous dose (125 IU/kg) in cynomolgus monkeys (n=6, mean±SD). Plasma concentrations were measured by ELISA.

Figure 8A:
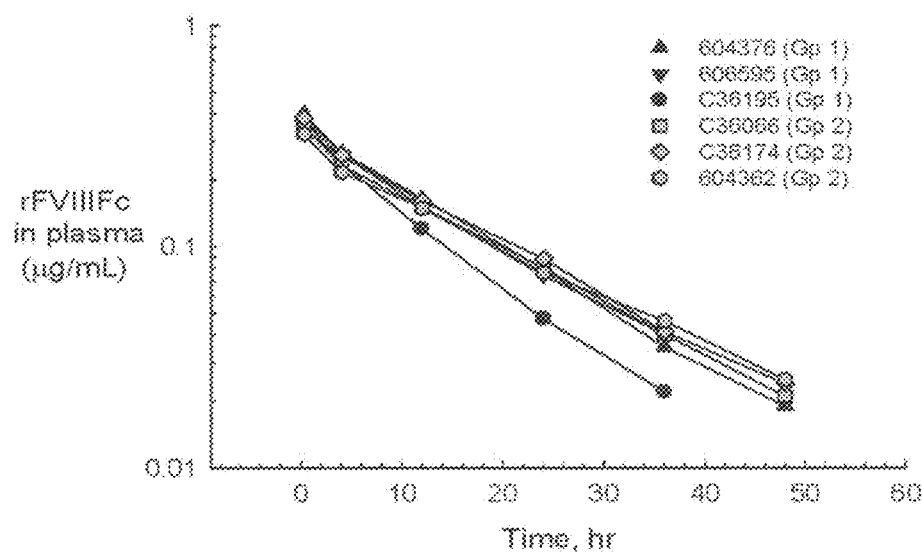
Figure 8B:
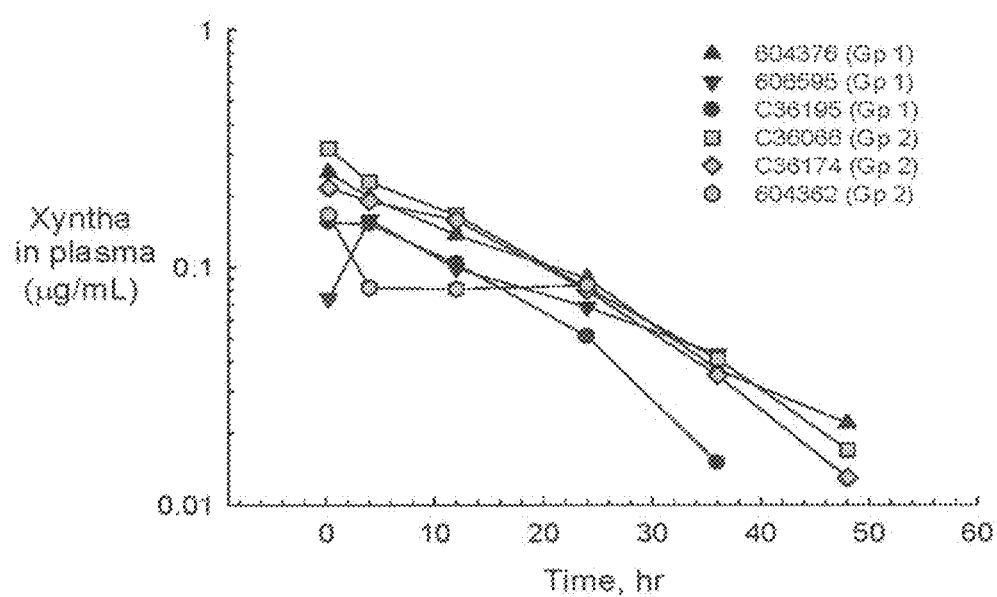

FIGS. 8A-8B. Individual plasma concentration versus time curves of rFVIIIFc and XYNTHA® after a single intravenous dose (125 IU/kg) in cynomolgus monkeys (n=6, mean±SD). Plasma concentrations were measured by ELISA. (FIG. 8A) rFVIIIFc by ELISA. (FIG. 8B) XYNTHA® by ELISA.

Figure 9:
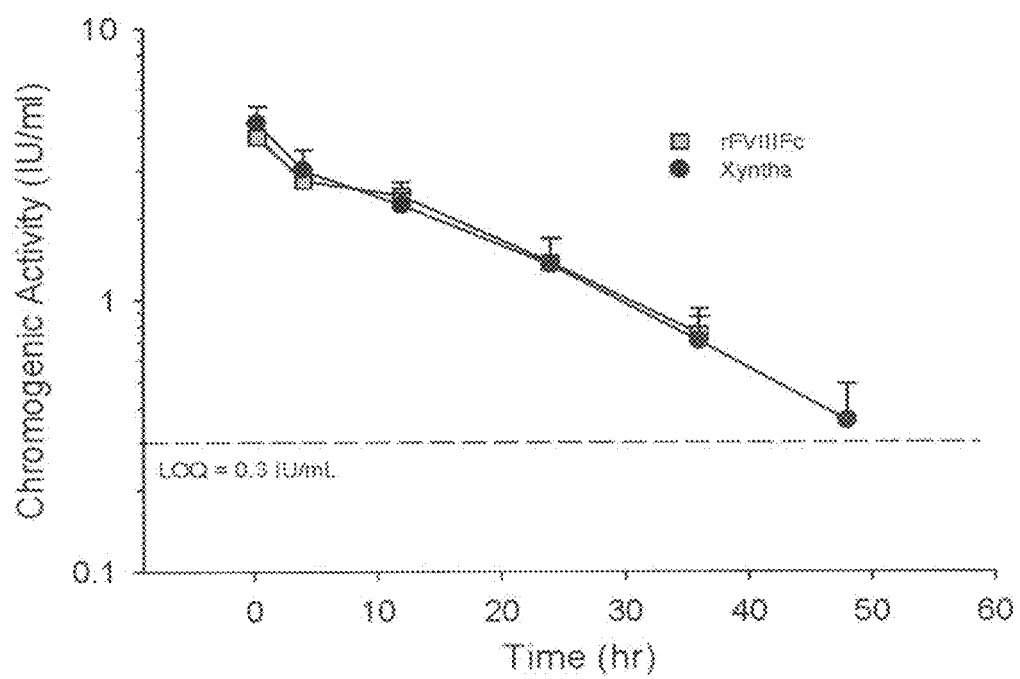

FIG. 9. Group mean plasma chromogenic activity after a single intravenous dose (125 IU/kg) of rFVIIIFc and XYNTHA® in cynomolgus monkeys (n=6, mean±SD). FVIII activity was measured using a FVIII-specific chromogenic activity assay.

Figure 10A:
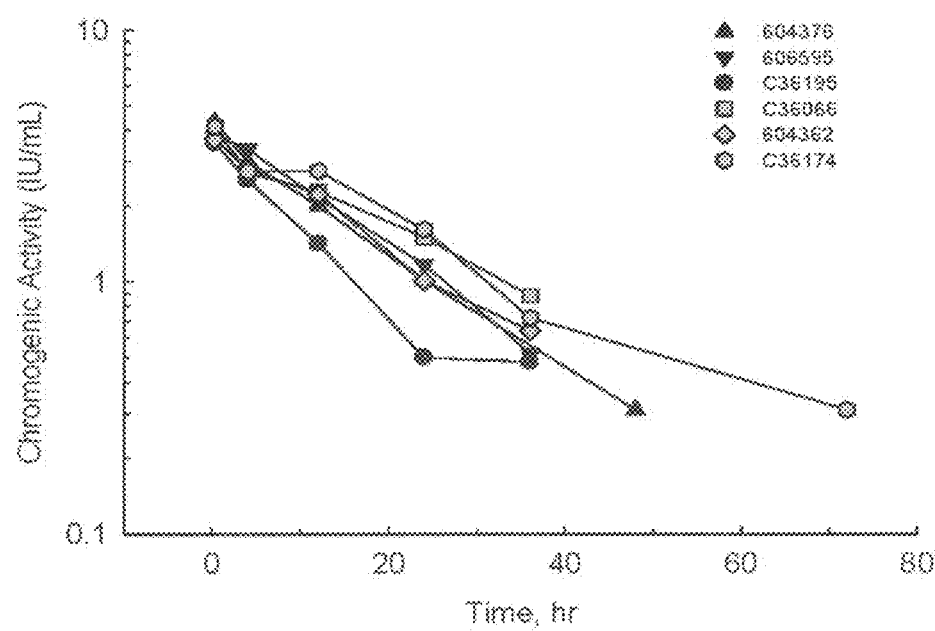
Figure 10B:
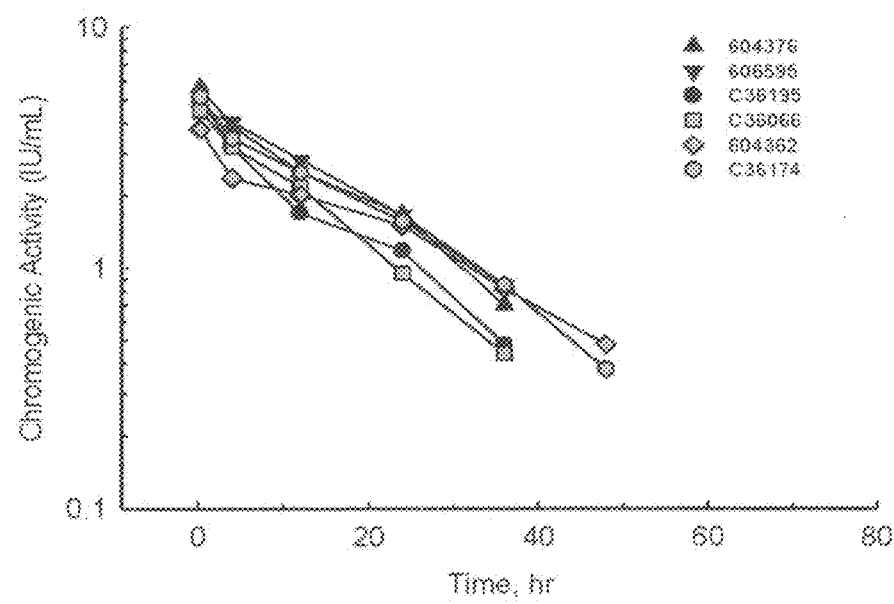

FIGS. 10A-10B. Individual plasma chromogenic activity versus time curves after a single intravenous dose (125 UI/kg) of rFVIIIFc and XYNTHA® in cynomolgus monkeys (n=6, mean±SD). FVIII activity was measured using a FVIII-specific chromogenic activity assay. (FIG. 10A) rFVIIIFc Chromogenic Activity. (FIG. 10B) XYNTHA® Chromogenic Activity.

Figure 11:
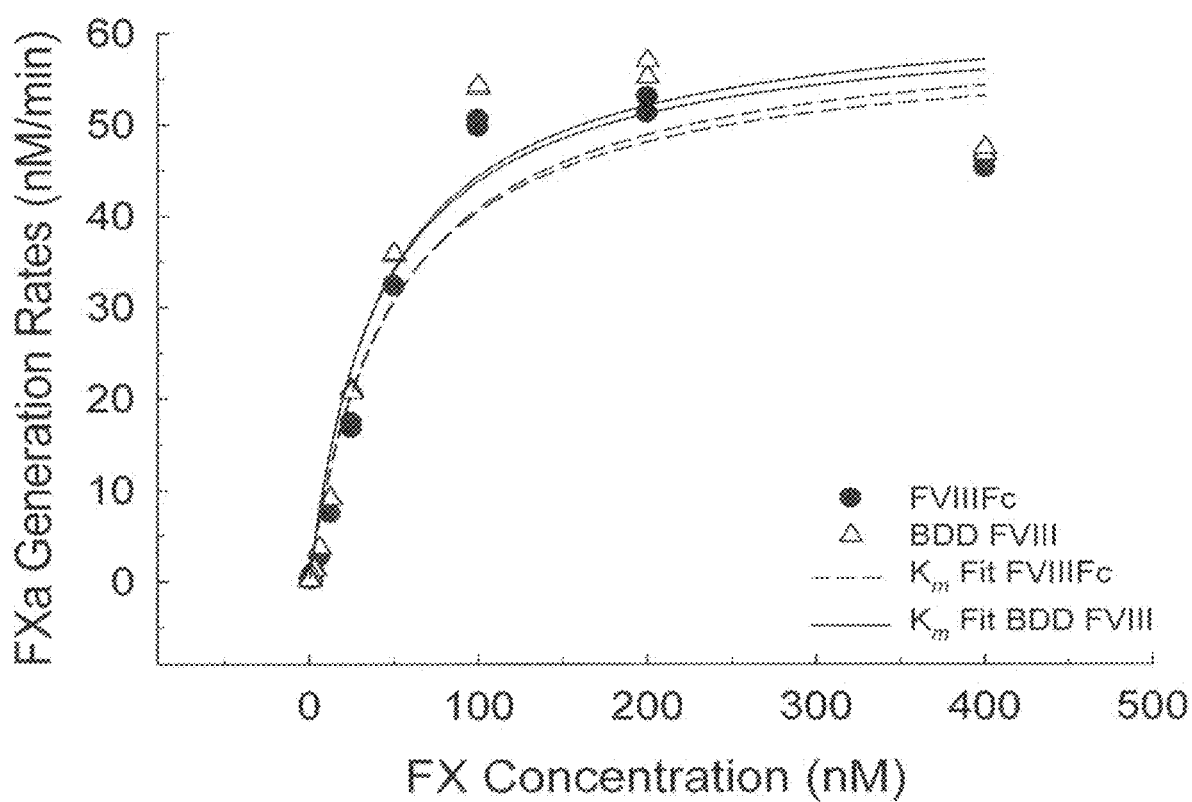

FIG. 11. Biochemical characterization of rFVIII-Fc: Activation of Factor X as a function of Factor X concentration.

Figure 12:
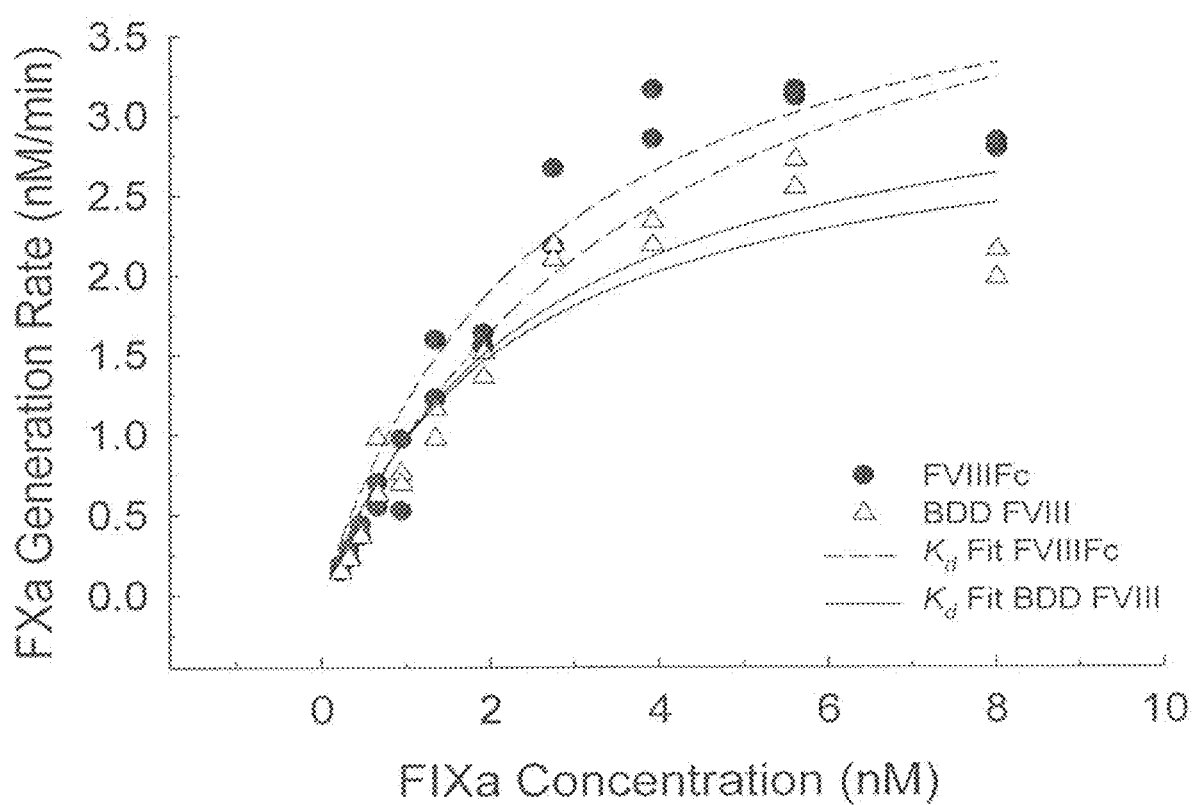

FIG. 12. Biochemical characterization of rFVIII-Fc: Activation of Factor X as a function of Factor IXa concentration.

FIG. 13A. Observed group mean FVIII activity (±SE) (one stage assay, 25 IU/kg) versus time.

Figure 13B:
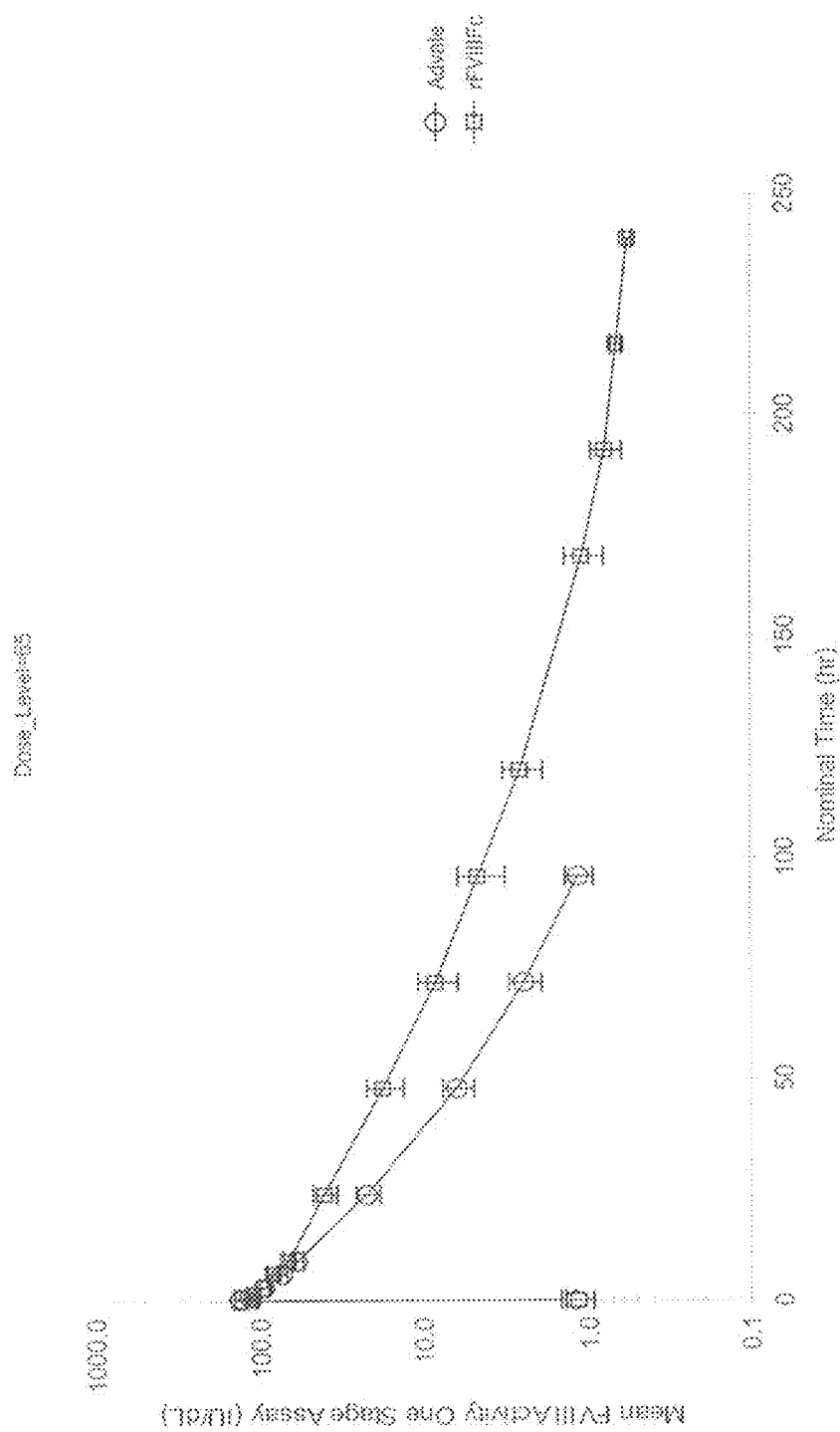

FIG. 13B. Observed group mean FVIII activity (+SE) (one stage assay, 65 IU/kg) versus time.

Figure 13C:
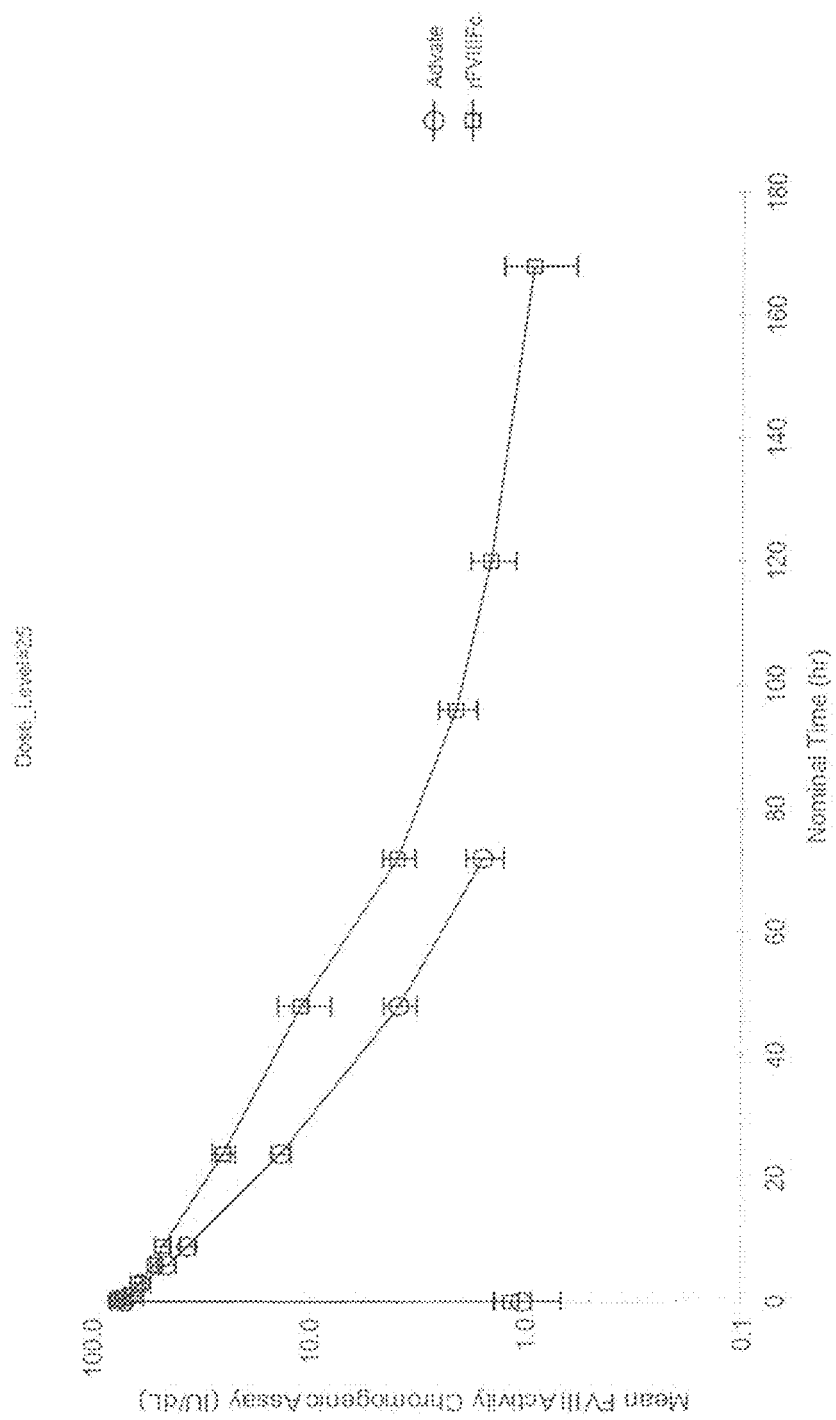

FIG. 13C. Observed group mean FVIII activity (±SE) (chromogenic assay, 25 IU/kg) versus time.

Figure 13D:
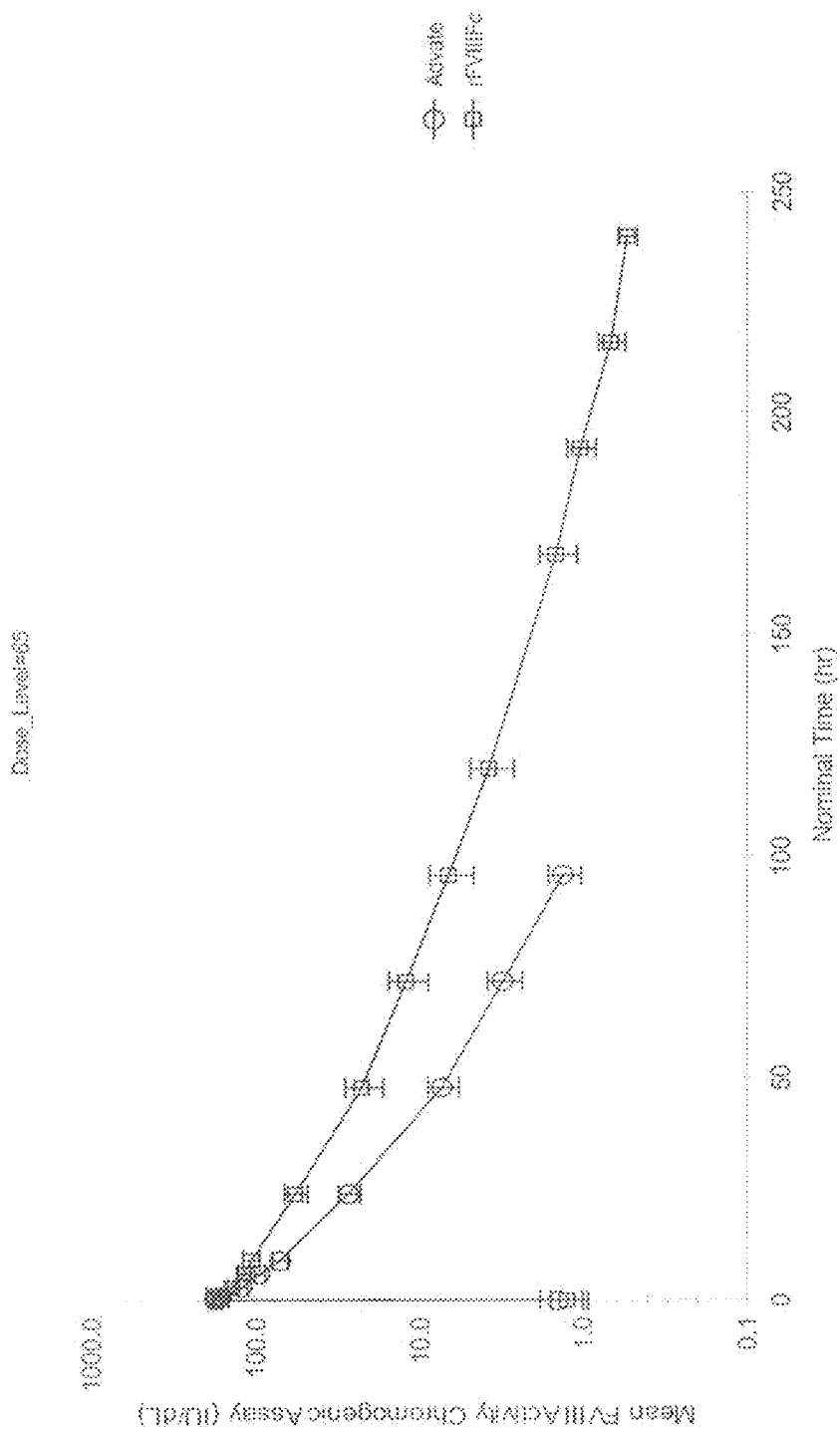

FIG. 13D. Observed group mean FVIII activity (+SE) (chromogenic assay, 65 IU/kg) versus time.

Figure 14A:
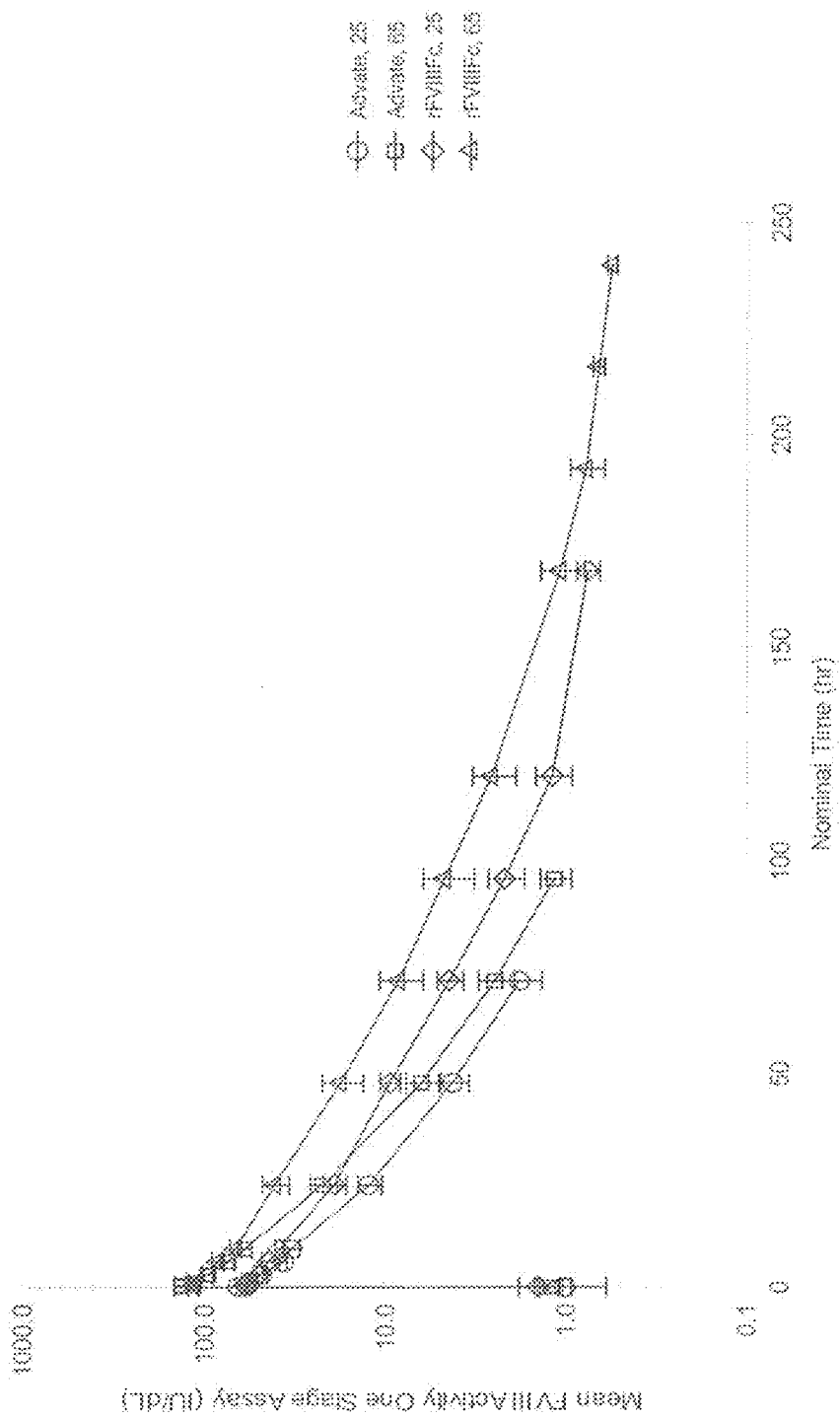

FIG. 14A. Observed group mean FVIII activity (+SE) (one stage assay) versus time.

Figure 14B:
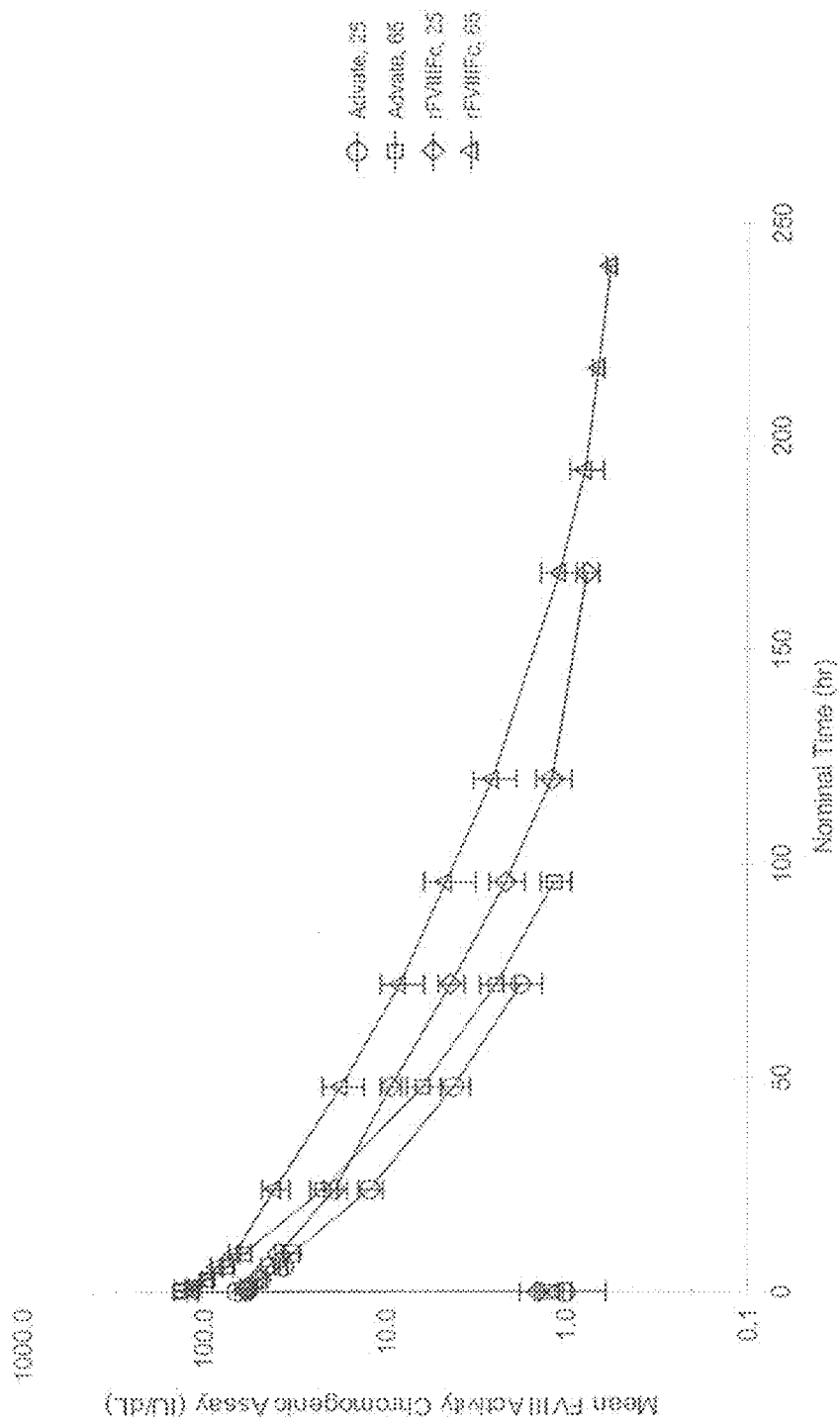

FIG. 14B. Observed group mean FVIII activity (±SE) (chromogenic assay) versus time.

DETAILED DESCRIPTION OF THE INVENTION

The present invention provides a method of treating Hemophilia A with Factor VIII using a longer dosing interval and/or greater AUC than is possible with currently known Factor VIII products. The present invention also provides improved Factor VIII chimeric polypeptides, Factor VIII chimeric polynucleotides, and methods of production.

Treatment of hemophilia A is by replacement therapy targeting restoration of FVIII activity to 1 to 5% of normal levels to prevent spontaneous bleeding (Mannucci, P. M., et al., N. Engl. J. Med. 344:1773-9 (2001), herein incorporated by reference in its entirety). There are plasma-derived and recombinant FVIII products available to treat bleeding episodes on-demand or to prevent bleeding episodes from occurring by treating prophylactically. Based on the half-life of these products (10-12 hr) (White G. C., et al., Thromb. Haemost. 77:660-7 (1997): Morfini, M., Haemophilia 9 (suppl 1):94-99: discussion 100 (2003)), treatment regimens require frequent intravenous administration, commonly two to three times weekly for prophylaxis and one to three times daily for on-demand treatment (Manco-Johnson. M. J., et al., N. Engl. J. Med. 357:535-544 (2007)), each of which is incorporated herein by reference in its entirety. Such frequent administration is painful and inconvenient.

The present invention provides a method of administering Factor VIII to a subject in need thereof, comprising administering to the subject a therapeutic dose of a chimeric Factor VIII polypeptide, e.g., a chimeric Factor VIII-Fc polypeptide, or a hybrid of such a polypeptide at a dosing interval at least about one and one-half times longer than the dosing interval required for an equivalent amount of said Factor VIII without the non-Factor VIII portion (a polypeptide consisting of said Factor VIII portion), e.g., without the Fc portion.

The dosing interval may be at least about one and one-half to six times longer, one and one-half to five times longer, one and one-half to four times longer, one and one-half to three times longer, or one and one-half to two times longer, than the dosing interval required for an equivalent amount of said Factor VII without the non-Factor VIII portion (a polypeptide consisting of said Factor VIII portion), e.g., without the Fc portion. The dosing interval may be at least about one and one-half, two, two and one-half, three, three and one-half, four, four and one-half, five, five and one-half or six times longer than the dosing interval required for an equivalent amount of said Factor VIII without the non-Factor VIII portion (a polypeptide consisting of said Factor VIII portion), e.g., without the Fc portion. The dosing interval may be about every five, six, seven, eight, nine, ten, eleven, twelve, thirteen, or fourteen days or longer.

The dosing interval may be at least about one and one-half to 5, one and one-half, 2, 3, 4, or 5 days or longer.

The present invention also provides a method of administering Factor VIII to a subject in need thereof, comprising administering to the subject a therapeutic dose of a chimeric Factor VIII polypeptide, e.g., a chimeric Factor VIII-Fc polypeptide, or a hybrid of such a polypeptide to obtain an area under the plasma concentration versus time curve (AUC) at least about one and one-quarter times greater than the AUC obtained by an equivalent amount of said Factor VIII without non-Factor VIII portion (a polypeptide consisting of said Factor VIII portion), e.g., without the Fc portion.

The present invention also provides a method of administering Factor VIII to a subject in need thereof, comprising administering to the subject a therapeutic dose of a polypeptide comprising a Factor VIII and an Fc or a hybrid of such a polypeptide at a dosing interval of about every five, six, seven, eight, nine, ten, eleven, twelve, thirteen, or fourteen days or longer.

The methods of the invention may be practiced on a subject in need of prophylactic treatment or on-demand treatment.

"Administering," as used herein, means to give a pharmaceutically acceptable Factor VIII polypeptide of the invention to a subject via a pharmaceutically acceptable route. Preferred routes of administration are intravenous, e.g., intravenous injection and intravenous infusion. Additional routes of administration include, e.g., subcutaneous, intramuscular, oral, nasal, and pulmonary administration. Chimeric polypeptides and hybrid proteins may be administered as part of a pharmaceutical composition comprising at least one excipient.

"Area under the plasma concentration versus time curve (AUC)," as used herein, is the same as the term of art in pharmacology, and is based upon the rate and extent of absorption if factor VIII following administration. AUC is determined over a specified time period, such as 12, 18, 24, 36, 48, or 72 hours, or for infinity using extrapolation based on the slope of the curve. Unless otherwise specified herein, AUC is determined for infinity. The determination of AUC may be carried out in a single subject, or in a population of subjects for which the average is calculated.

"B domain" of Factor VIII, as used herein, is the same as the B domain known in the art that is defined by internal amino acid sequence identity and sites of proteolytic cleavage by thrombin, e.g., residues Ser741-Arg1648 of full length human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172: C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. Preferably, the B domain of Factor VIII is deleted ("B domain deleted factor VIII" or "BDD FVIII"). An example of a BDD FVIII is REFACTO® (recombinant BDD FVIII), which has the same sequence as the Factor VIII portion of the sequence in Table 2A(i) (amino acids −19 to 1438 or 1 to 1438 of SEQ ID NO:2).

A "B domain deleted factor VIII" may have the full or partial deletions disclosed in U.S. Pat. Nos. 6,316,226, 6,346,513, 7,041,635, 5,789,203, 6,060,447, 5,595,886, 6,228.620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. Nos. 6,060,447, 5,595,886, and 6,228,620). In some embodiments, a B domain deleted factor VIII has a deletion described in col. 1, lines 25 to col. 2, line 40 of U.S. Pat. No. 5,972,885: col. 6, lines 1-22 and example 1 of U.S. Pat. No. 6,048,720; col. 2, lines 17-46 of U.S. Pat. No. 5,543,502: col. 4, line 22 to col. 5, line 36 of U.S. Pat. No. 5,171,844, col. 2, lines 55-68, FIG. 2, and example 1 of U.S. Pat. No. 5,112,950: col. 2, line 2 to col. 19, line 21 and table 2 of U.S. Pat. No. 4,868,112: col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some embodiments, a B domain deleted factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B domain deleted factor VIII may also contain a deletion of amino acids 771-1666 or amino acids 868-1562 of factor VIII. Meulien P., et al. *Protein Eng.* 2(4): 301-6 (1988), incorporated herein by reference in its entirety. Additional B domain deletions that are part of the invention include, e.g.: deletion of amino acids 982 through 1562 or 760 through 1639 (Toole et al., *Proc. Natl. Acad. Sci. U.S.A.* (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al. DNA (1987) 6:553-564)), 741 though 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions may be made in any Factor VIII sequence.

"Chimeric polypeptide," as used herein, means a polypeptide that includes within it at least two polypeptides (or subsequences or peptides) from different sources. Chimeric polypeptides may include, e.g., two, three, four, five, six, seven, or more polypeptides from different sources, such as different genes, different cDNAs, or different animal or other species. Chimeric polypeptides may include, e.g., one or more linkers joining the different subsequences. Thus, the subsequences may be joined directly or they may be joined indirectly, via linkers, or both, within a single chimeric polypeptide. Chimeric polypeptides may include, e.g., additional peptides such as signal sequences and sequences such as 6His and FLAG that aid in protein purification or detection. In addition, chimeric polypeptides may have amino acid or peptide additions to the N- and/or C-termini.

In some embodiments, the chimeric polypeptide comprises a Factor VIII portion and a non-Factor VIII portion. Exemplary non-Factor VIII portions include, e.g., Fc, XTEN, and albumin. Exemplary chimeric polypeptides of the invention include, e.g., chimeric Factor VIII-Fc polypeptides, chimeric Factor VIII-XTEN polypeptides, and chimeric Factor VIII-albumin polypeptides.

Exemplary chimeric Factor VIII-Fc polypeptides include, e.g., SEQ ID NOs:2, 6, 8, 10, and 12 (Table 2), with or without their signal sequences and the chimeric Fc polypeptide of SEQ ID NO:4 (Table 2).

The chimeric polypeptide may comprise a sequence at least 90% or 95% identical to the Factor VIII and Fc amino acid sequence shown in Table 2A(i) without a signal sequence (amino acids 1 to 1665 of SEQ ID NO:2) or at least 90% or 95% identical to the Factor VIII and Fc amino acid sequence shown in Table 2A(i) with a signal sequence (amino acids −19 to 1665 of SEQ ID NO:2). The chimeric polypeptide may comprise a sequence identical to the Factor VIII and Fc amino acid sequence shown in Table 2A(i) without a signal sequence (amino acids 1 to 1665 of SEQ ID NO:2) or identical to the Factor VIII and Fc amino acid sequence shown in Table 2A(i) with a signal sequence (amino acids −19 to 1665 of SEQ ID NO:2).

As discussed above, exemplary chimeric polypeptides include Factor VIII fused to one or more XTEN polypeptides. Schellenburger et al., Nat. Biotech. 27:1186-90 (2009), which is incorporated herein by reference in its entirety. Factor VIII can be fused to either the N-terminal end of the XTEN polypeptide or to the C-terminal end of the XTEN polypeptide, provided the Factor VIII component of the Factor VIII-XTEN fusion protein can be processed by an protease to yield a processed Factor VIII containing polypeptide. A protease site may be included between the XTEN portion and the Factor VIII portion to allow such processing. XTEN polypeptides include, e.g., those disclosed in WO 2009/023270, WO 2010/091122, WO 2007/103515, US 2010/0189682, and US 2009/0092582, each of which is incorporated herein by reference in its entirety.

As discussed above, exemplary chimeric polypeptides also include Factor VIII fused to one or more albumin polypeptides. Preferably the albumin is human albumin. Factor VIII can be fused to either the N-terminal end of the albumin or to the C-terminal end of the albumin, provided the Factor VIII component of the Factor VIII-albumin fusion protein can be processed by an enzymatically-active proprotein convertase to yield a processed Factor VIII-containing polypeptide. Examples of albumin, e.g., fragments thereof, that may be used in the present invention are known, e.g., U.S. Pat. Nos. 7,592,010; 6,686,179; and Schulte, Thrombosis Res. 124 Suppl. 2:S6-S8 (2009), each of which is incorporated herein by reference in its entirety.

In some embodiments, a chimeric polypeptide comprising a Factor VIII portion has an increased half-life (t1/2) over a polypeptide consisting of the same Factor VIII portion without the non Factor VIII portion. A chimeric Factor VIII polypeptide with an increased t1/2 may be referred to herein as a long-acting Factor VIII. Long-acting chimeric Factor VIII polypeptides include, e.g., Factor VIII fused to Fc (including, e.g., chimeric Factor VIII polypeptides in the form of a hybrid such as a FVIIIFc monomer dimer hybrid; see Example 1, FIG. 1, and Table 2A; and U.S. Pat. Nos. 7,404,956 and 7,348,004). Factor VIII fused to XTEN, and Factor VIII fused to albumin.

"Culture," "to culture" and "culturing," as used herein, means to incubate cells under in vitro conditions that allow for cell growth or division or to maintain cells in a living state. "Cultured cells," as used herein, means cells that are propagated in vitro.

"Factor VIII," as used herein, means functional factor VIII polypeptide in its normal role in coagulation, unless otherwise specified. Thus, the term Factor VIII includes variant polypeptides that are functional. Preferred factor VIII proteins are the human, porcine, canine, and murine factor VIII proteins. As described in the Background Art section, the full length polypeptide and polynucleotide sequences are known, as are many functional fragments, mutants and modified versions. Examples of human factor VIII sequences are shown as subsequences in SEQ ID NOs:2, 6, 8, 10, and 12 (Table 2). Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Preferred Factor VIII variants include B domain deletions, whether partial or full deletions.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., Hum. Mutat. 19:274-8 (2002)), incorporated herein by reference in its entirety. In addition, comparisons between factor VIII from humans and other species has identified conserved residues that are likely to be required for function (Cameron et al., Thromb. Haemost. 79:317-22 (1998): U.S. Pat. No. 6,251,632), incorporated herein by reference in its entirety.

The human factor VIII gene was isolated and expressed in mammalian cells (Toole, J. J., et al., Nature 312:342-347 (1984): Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558: U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, disclose a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following patents U.S. Pat. Nos. 6,316,226 and 6,346,513, both assigned to Baxter; U.S. Pat. No. 7,041,635 assigned to In2Gen: U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk: U.S. Pat. No. 5,171,844 assigned to Immuno Ag; U.S. Pat. No. 5,112,950 assigned to Transgene S. A.; U.S. Pat. No. 4,868,112 assigned to Genetics Institute, each of which is incorporated herein by reference in its entirety.

The porcine factor VIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of factor VIII sequences from a pig spleen cDNA library has been reported (Healey, J. F., et al., Blood 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. 6,458, 563, incorporated herein by reference in its entirety assigned to Emory discloses a B-domain deleted porcine Factor VIII.

The Factor VIII (or Factor VIII portion of a chimeric polypeptide) may be at least 90% or 95% identical to a Factor VIII amino acid sequence shown in Table 2 without a signal sequence (amino acids 1 to 1438 of SEQ ID NO:2: amino acids 1 to 2332 of SEQ ID NO:6; amino acids 1 to 740 of SEQ ID NO:8: amino acids 1 to 745 of SEQ ID NO:10; or amino acids 1 to 684 of SEQ ID NO: 12). The Factor VIII (or Factor VIII portion of a chimeric polypeptide) may be identical to a Factor VIII amino acid sequence shown in Table 2 without a signal sequence (amino acids 1 to 1438 of SEQ ID NO:2; amino acids 1 to 2332 of SEQ ID NO:6; amino acids 1 to 740 of SEQ ID NO:8; amino acids 1 to 745 of SEQ ID NO: 10; or amino acids 1 to 684 of SEQ ID NO: 12).

The Factor VIII (or Factor VIII portion of a chimeric polypeptide) may be at least 90% or 95% identical to a Factor VIII amino acid sequence shown in Table 2 with a signal sequence (amino acids −19 to 1438 of SEQ ID NO:2: amino acids −19 to 2332 of SEQ ID NO:6: amino acids −19 to 740 of SEQ ID NO:8; amino acids −19 to 745 of SEQ ID NO: 10; or amino acids −20 to 684 of SEQ ID NO: 12). The Factor VIII (or Factor VIII portion of a chimeric polypeptide) may be identical to a Factor VIII amino acid sequence shown in Table 2 with a signal sequence (amino acids −19 to 1438 of SEQ ID NO:2; amino acids −19 to 2332 of SEQ ID NO:6; amino acids −19 to 740 of SEQ ID NO:8; amino acids −19 to 745 of SEQ ID NO: 10; or amino acids −20 to 684 of SEQ ID NO: 12).

"Equivalent amount," as used herein, means the same amount of Factor VIII activity as expressed in International Units, which is independent of molecular weight of the polypeptide in question. One International Unit (IU) of factor VIII activity corresponds approximately to the quantity of factor VIII in one milliliter of normal human plasma. Several assays are available for measuring Factor VIII activity, including the European Pharmacopoeia chromogenic substrate assay and a one stage clotting assay.

"Fc," as used herein, means functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. The FcRn binding partners include, e.g., whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; Md., incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An Fc may comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

Fc (or Fc portion of a chimeric polypeptide) may contain one or more mutations, and combinations of mutations.

Fc (or Fc portion of a chimeric polypeptide) may contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of US 2009/0264627 A1, which is incorporated herein by reference in its entirety; and the mutants disclosed at page 2, paragraphs [0014] to [0021] of US 20090163699 A1, which is incorporated herein by reference in its entirety.

Fc (or Fc portion of a chimeric polypeptide) may also include, e.g., the following mutations: The Fc region of IgG can be modified according to well recognized procedures such as site directed mutagenesis and the like to yield modified IgG or Fc fragments or portions thereof that will be bound by FcRn. Such modifications include, e.g., modifications remote from the FcRn contact sites as well as modifications within the contact sites that preserve or even enhance binding to the FcRn. For example the following single amino acid residues in human IgG1 Fc (Fyl 1) can be substituted without significant loss of Fc binding affinity for FcRn: P238A, S239A, K246A, K248A, D249A. M252A, T256A. E258A. T260A, D265A, S267A. H268A, E269A, D270A, E272A, L274A. N276A, Y278A, D280A, V282A. E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A. S383A, N384A. Q386A. E388A. N389A. N390A, Y391F, K392A. L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Certain of these mutations may confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie 1995, Therapeutic Immunology 2:77, which is incorporated herein by reference in its entirety; and Armour et al. 1999, Eur. J. Immunol. 29:2613, which is incorporated herein by reference in its entirety). As a further example of new functionality arising from mutations described above affinmity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include, e.g., T256A, T307A, E380A, and N434A (Shields et al. 2001, J. Biol. Chem. 276:6591, which is incorporated herein by reference in its entirety).

The Fc (or Fc portion of a chimeric polypeptide) may be at least 90% or 95% identical to the Fc amino acid sequence shown in Table 2 (amino acids 1439 to 1665 of SEQ ID NO:2; amino acids 2333 to 2559 of SEQ ID NO:6; amino acids 741 to 967 of SEQ ID NO:8; amino acids 746 to 972 of SEQ ID NO: 10; amino acids 685 to 924 of SEQ ID NO: 12). The Fc (or Fc portion of a chimeric polypeptide) may be identical to the Fc amino acid sequence shown in Table 2 (amino acids 1439 to 1665 of SEQ ID NO:2; amino acids 2333 to 2559 of SEQ ID NO:6; amino acids 741 to 967 of SEQ ID NO:8; amino acids 746 to 972 of SEQ ID NO: 10; amino acids 685 to 924 of SEQ ID NO: 12).

"Hybrid" polypeptides and proteins, as used herein, means a combination of a chimeric polypeptide with a second polypeptide. The chimeric polypeptide and the second polypeptide in a hybrid may be associated with each other via protein-protein interactions, such as charge-charge or hydrophobic interactions. The chimeric polypeptide and the second polypeptide in a hybrid may be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide may be a second copy of the same chimeric polypeptide or it may be a non-identical chimeric polypeptide. See, e.g., FIG. 1, Example 1, and Table 2. In preferred embodiments, the second polypeptide is a polypeptide comprising an Fc. In preferred embodiments, the chimeric polypeptide is a chimeric Factor VIII-Fc polypeptide and the second polypeptide consists essentially of Fc, e.g, the hybrid polypeptide of Example 1, which is a rFVIIIFc recombinant fusion protein consisting of a single molecule of recombinant B-domain deleted human FVIII (BDD-rFVIII) fused to the dimeric Fc domain of the human IgG1, with no intervening linker sequence. This hybrid polypeptide is referred to herein as FVIIIFc monomeric Fc fusion protein, FVIIIFc monomer hybrid, monomeric FVIIIIFc hybrid, and FVIIIFc monomer-dimer. See Example 1, FIG. 1, and Table 2A. The Examples provide preclinical and clinical data for this hybrid polypeptide.

The second polypeptide in a hybrid may comprise or consist essentially of a sequence at least 90% or 95% identical to the amino acid sequence shown in Table 2A(ii) without a signal sequence (amino acids 1 to 227 of SEQ ID NO:4) or at least 90% or 95% identical to the amino acid sequence shown in Table 2A(ii) with a signal sequence (amino acids −20 to 227 of SEQ ID NO:4). The second polypeptide may comprise or consist essentially of a sequence identical to the amino acid sequence shown in Table 2A(ii) without a signal sequence (amino acids 1 to 227 of SEQ ID NO:4) or identical to the amino acid sequence shown in Table 2A(ii) with a signal sequence (amino acids −20 to 227 of SEQ ID NO:4).

FIG. 1 is a schematic showing the structure of a B domain deleted factor VIII-Fc chimeric polypeptide, and its association with a second polypeptide that is an Fc polypeptide. To obtain this hybrid, the coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion was from serine 743 (S743; 2287 bp) to glutamine 1638 (Q1638; 4969 bp) for a total deletion of 2682 bp. Then, the coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter. A second identical Fc sequence including the mouse Igk signal sequence was obtained by RT-PCR and cloned downstream of the second promoter, EF1α in the expression vector pBUDCE4.1.

The rFVIIIFc expression vector was transfected into human embryonic kidney 293 cells (HEK293H; Invitrogen) using Lipofectamine 2000 transfection reagent (Invitrogen). Stable clonal cell lines were generated by selection with Zeocin (Invitrogen). One clonal cell line, 3C4-22 was used to generate FVIIIFc for characterization in vivo. Recombinant FVIIIFc was produced and purified (McCue et al. 2009) at Biogen Idec (Cambridge, Mass.). The transfection strategy described above was expected to yield three products, i.e., monomeric rFVIIIFc hybrids, dimeric rFVIIIFc hybrids and dimeric Fc. However, there was essentially no dimeric rFVIIIFc detected in the conditioned medium from these cells. Rather, the conditioned medium contained Fc and monomeric rFVIIIFc. It is possible that the size of dimeric rFVIIIFc was too great and prevented efficient secretion from the cell. This result was beneficial since it rendered the purification of the monomer less complicated than if all three proteins had been present. The material used in these studies had a specific activity of approximately 9000 IU/mg.

"Dosing interval," as used herein, means the amount of time that elapses between multiple doses being administered to a subject. The comparison of dosing interval may be carried out in a single subject or in a population of subjects and then the average obtained in the population may be calculated.

The dosing interval when administering a chimeric Factor VIII polypeptide, e.g., a chimeric Factor VIII-Fc polypeptide (a polypeptide comprising a Factor VIII or a hybrid) of the invention may be at least about one and one-half times longer than the dosing interval required for an equivalent amount of said Factor VIII without the non-Factor VIII portion, e.g., without the Fc portion (a polypeptide consisting of said Factor VIII). The dosing interval may be at least about one and one-half to six times longer, one and one-half to five times longer, one and one-half to four times longer, one and one-half to three times longer, or one and one-half to two times longer, than the dosing interval required for an equivalent amount of said Factor VIII without the non-Factor VIII portion, e.g., without the Fc portion (a polypeptide consisting of said Factor VIII). The dosing interval may be at least about one and one-half, two, two and one-half, three, three and one-half, four, four and one-half, five, five and one-half or six times longer than the dosing interval required for an equivalent amount of said Factor VIII without the non-Factor VIII portion, e.g., without the Fc portion (a polypeptide consisting of said Factor VIII). The dosing interval may be about every five, six, seven, eight, nine, ten, eleven, twelve, thirteen, or fourteen days or longer. The dosing interval may be at least about one and one-half to 5, one and one-half, 2, 3, 4, or 5 days or longer. For on-demand treatment, the dosing interval of said chimeric polypeptide or hybrid is about once every 24-36, 24-48, 24-72, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

Preferably, the effective dose is 25-65 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, or 65 IU/kg) and the dosing interval is once every 3-5, 3-6, 3-7, 3, 4, 5, 6, 7, or 8 or more days, or three times per week, or no more than three times per week. Preferably, the effective dose is 65 IU/kg and the dosing interval is once weekly, or once every 6-7 days.

"Long-acting Factor VIII" is a Factor VIII having an increased half-life (also referred to herein as t1/2, t1/2 beta, elimination half-life and HL) over a reference Factor VIII. The increased half-life of a long-acting Factor VIII may be due to fusion to one or more non-Factor VIII polypeptides such as, e.g., Fc, XTEN or albumin. The increased half-life may be due to one or more modification, such as, e.g., pegylation. Exemplary long-acting Factor VIII polypeptides include, e.g., chimeric Factor VIII polypeptides comprising Fc, chimeric Factor VIII polypeptides comprising XTEN and chimeric Factor VIII polypeptides comprising albumin. Additional exemplary long-acting Factor VIII polypeptides include, e.g., pegylated Factor VIII.

The "reference" polypeptide, in the case of a long-acting chimeric Factor VIII polypeptide, is a polypeptide consisting essentially of the Factor VIII portion of the chimeric polypeptide, e.g., the same Factor VIII portion without the Fc portion, without the XTEN portion, or without the albumin portion. Likewise, the reference polypeptide in the case of a modified Factor VIII is the same Factor VIII without the modification, e.g., a Factor VIII without the pegylation.

In some embodiments, the long-acting Factor VIII has one or more of the following properties when administered to a subject:

a mean residence time (MRT) (activity) in said subject of about 14-41.3 hours;
a clearance (CL) (activity) in said subject of about 1.22-5.19 mL/hour/kg or less;
a t1/2beta (activity) in said subject of about 11-26.4 hours;
an incremental recovery (K value) (activity; observed) in said subject of about 1.38-2.88 IU/dL per IU/kg;
a Vss (activity) in said subject of about 37.7-79.4 mL/kg; and
an AUC/dose in said subject of about 19.2-81.7 IU*h dL per IU/kg.

In some embodiments, the long-acting Factor VIII has one or more of the following properties when administered to a patient population:

a mean incremental recovery (K-Value) (activity; observed) greater that 1.38 IU/dL per IU/kg;
a mean incremental recovery (K-Value) (activity; observed) of at least about 1.5, at least about 1.85, or at least about 2.46 IU/dL per IU/kg,
a mean clearance (CL) (activity) in said patient population of about 2.33±1.08 mL/hour/kg or less;
a mean clearance (CL) (activity) in said patient population of about 1.8-2.69 mL/hour/kg;
a mean clearance (CL) (activity) in said patient population that is about 65% of the clearance of a polypeptide comprising said Factor VIII without modification:
a mean mean residence time (MRT) (activity) in said patient population of at least about 26.3±8.33 hours;
a mean MRT (activity) in said patient population of about 25.9-26.5 hours;
a mean MRT (activity) in said patent population that is about 1.5 fold longer than the mean MRT of a polypeptide comprising said Factor VIII without modification;
a mean t1/2beta (activity) in said patient population of about 18.3±5.79 hours;
a mean t1/2beta (activity) in said patient population that is about 18-18.4 hours;
a mean t1/2beta (activity) in said patient population that is about 1.5 fold longer than the mean t1/2beta of a polypeptide comprising said Factor VIII without modification;
a mean incremental recovery (K value) (activity; observed) in said patient population of about 2.01±0.44 IU/dL per IU/kg;
a mean incremental recovery (K value) (activity: observed) in said patient population of about 1.85-2.46 IU/dL per IU/kg;
a mean incremental recovery (K value) (activity, observed) in said patient population that is about 90% of the mean incremental recovery of a polypeptide comprising said Factor VIII without modification;
a mean Vss (activity) in said patient population of about 55.1±12.3 mL/kg;
a mean Vss (activity) in said patient population of about 45.3-56.1 mL/kg;
a mean AUC/dose (activity) in said patient population of about 49.9±18.2 IU*h/dL per IU/kg;
a mean AUC/dose (activity) in said patient population of about 44.8-57.6 IU*h/dL per IU/kg.

"On-demand treatment," as used herein, means treatment that is intended to take place over a short course of time and is in response to an existing condition, such as a bleeding episode, or a perceived need such as planned surgery. Conditions that may require on-demand treatment include, e.g., a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal hemiotomy, synovec- tomy, total knee replacement, craniotomy, osteosynthesis, trauma surgery, intracranial surgery, intra-abdominal sur- gery, intrathoracic surgery, or joint replacement surgery.

Preferably, on-demand treatment resolves greater than 80% (greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99%, or 100%) or 80-100%, 80-90%, 85-90%, 90-100%, 90-95%, or 95-100% of bleeds (e.g., spontaneous bleeds) in a single dose. Preferably, greater than 80% (greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or 100%) or 80-100%, 80-90%, 85-90%, 90-100%, 90-95%, or 95-100% of bleeding episodes are rated excellent or good by physicians after on-demand treatment. Preferably, greater than 5%, (greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%), or 5-20%, 5-15%, 5-10%, 10-20% or 10-15% of bleeding episodes are rated as fair by physicians after on-demand treatment.

"Polypeptide," "peptide" and "protein" are used inter- changeably and refer to a polymeric compound comprised of covalently linked amino acid residues.

"Polynucleotide" and "nucleic acid" are used inter- changeably and refer to a polymeric compound comprised of covalently linked nucleotide residues. Polynucleotides may be DNA, cDNA, RNA, single stranded, or double stranded, vectors, plasmids, phage, or viruses. Polynucleotides include, e.g., those in Table 1, which encode the polypep- tides of Table 2 (see Table 1). Polynucleotides also include, e.g., fragments of the polynucleotides of Table 1, e.g., those that encode fragments of the polypeptides of Table 2, such as the Factor VIII, Fc, signal sequence, 6His and other fragments of the polypeptides of Table 2.

"Prophylactic treatment," as used herein, means admin- istering a Factor VIII polypeptide in multiple doses to a subject over a course of time to increase the level of Factor VIII activity in a subject's plasma. Preferably, the increased level is sufficient to decrease the incidence of spontaneous bleeding or to prevent bleeding, e.g., in the event of an unforeseen injury. Preferably, during prophylactic treatment, the plasma protein level in the subject does not fall below the baseline level for that subject, or below the level of Factor VIII that characterizes severe hemophilia (<1 IU/dl [1%]).

Preferably, the prophylaxis regimen is "tailored" to the individual patient, preferably by determining PK data for each patient and administering Factor VIII of the invention at a dosing interval that maintains a trough level of 1-3% FVIII activity. Adjustments may be made when a subject experiences unacceptable bleeding episodes defined as ≥2 spontaneous bleeding episodes over a rolling two-month period. In this case, adjustment will target trough levels of 3-5%. Preferably, prophylactic treatment results in preven- tion and control of bleeding, sustained control of bleeding, sustained protection from bleeding, and/or sustained benefit. Prophylaxis, e.g., sustained protection can be demonstrated by an increased AUC to last measured time point (AUC- LAST) and reduced clearance, resulting in increased termi- nal t1/2 compared to short acting FVIII. Preferably, prophy- laxis is demonstrated by better Cmax, better Tmax, and/or greater mean residence time versus short-acting FVIII. Pref- erably, prophylaxis results in no spontaneous bleeding epi- sodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, 90, 91, 92, 93, 94, 95, or 96 hours, preferably within 72 hours), after injection (e.g., the last injection). Preferably, prophy- laxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, or 90%, preferably greater than 50%), mean reduction in annualized bleeding episodes with once weekly dosing (e.g., at 65 IU/kg).

"Subject," as used herein means a human or a non-human mammal. Non-human mammals include, e.g., mice, dogs, primates, monkeys, cats, horses, cows, pigs, and other domestic animals and small animals.

"Therapeutic dose," as used herein, means a dose that achieves a therapeutic goal, as described herein. The calcu- lation of the required dosage of factor VIII is based upon the empirical finding that, on average, 1 IU of factor VIII per kg body weight raises the plasma factor VIII activity by approximately 2 IU/dL. The required dosage is determined using the following formula:

Required units=body weight(kg)×desired factor VIII rise(IU/dL or % of normal)×0.5 (IU/kg per IU/dL)

The therapeutic doses that may be used in the methods of the invention are about 10-100 IU/kg, more specifically, 10-20, 20-30, 30-40, 40-50, 50-60, 60-70, 70-80, 80-90, or 90-100 IU/kg, and more specifically, 10, 15, 20, 25, 30, 35, 40, 45, 50, 55, 60, 65, 70, 75, 80, 85, 90, 95, or 100 IU/kg.

Additional therapeutic doses that may be used in the methods of the invention are about 10 to about 150 IU/kg, more specifically, about 100-110, 110-120, 120-130, 130- 140, 140-150 IU/kg, and more specifically, about 110, 115, 120, 125, 130, 135, 140, 145, or 150 IU/kg.

"Variant," as used herein, refers to a polynucleotide or polypeptide differing from the original polynucleotide or polypeptide, but retaining essential properties thereof, e.g., factor VIII coagulant activity or Fc (FcRn binding) activity. Generally, variants are overall closely similar, and, in many regions, identical to the original polynucleotide or polypep- tide. Variants include, e.g., polypeptide and polynucleotide fragments, deletions, insertions, and modified versions of original polypeptides.

Variant polynucleotides may comprise, or alternatively consist of, a nucleotide sequence which is at least 85%, 90%, 95%, 96%, 97%, 98% or 99% identical to, for example, the nucleotide coding sequence in SEQ ID NO: 1, 3, 5, 7, 9, or 11 (the factor VIII portion, the Fc portion, individually or together) or the complementary strand thereto, the nucleo- tide coding sequence of known mutant and recombinant factor VIII or Fc such as those disclosed in the publications and patents cited herein or the complementary strand thereto, a nucleotide sequence encoding the polypeptide of SEQ ID NO:2, 4, 6, 8, 10, or 12 (the factor VIII portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant polypeptides may comprise, or alternatively consist of, an amino acid sequence which is at least 85%, 90%, 95%, 96%, 97%, 98%, 99% identical to, for example, the polypeptide sequence shown in SEQ ID NO:2, 4, 6, 8, 10, or 12 (the factor VIII portion, the Fc portion, individually or together), and/or polypeptide fragments of any of these polypeptides (e.g., those fragments described herein).

By a nucleic acid having a nucleotide sequence at least, for example, 95% "identical" to a reference nucleotide sequence, it is intended that the nucleotide sequence of the nucleic acid is identical to the reference sequence except that the nucleotide sequence may include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be, for example, the entire sequence shown in SEQ ID NO: 1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al. (Comp. App. Biosci. (1990) 6:237-245), which is herein incorporated by reference in its entirety In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2 (the factor VIII portion, the Fc portion, individually or together) or 4, or a known factor VIII or Fc polypeptide sequence, can be determined conventionally using known computer programs. A preferred method for determining the best overall match between a query sequence (reference or original sequence) and a subject sequence, also referred to as a global sequence alignment, can be determined using the FASTDB computer program based on the algorithm of Brutlag et al., Comp. App. Biosci. 6:237-245(1990), incorporated herein by reference in its entirety. In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=), Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching-alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polynucleotide variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., J. Biotechnology 7:199-216 (1988), incorporated herein by reference in its entirety.)

Moreover, ample evidence demonstrates that variants often retain a biological activity similar to that of the naturally occurring protein. For example, Gayle and coworkers (J. Biol. Chem 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., Blood 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, Factor VIII is modified, e.g., pegylated, at any convenient location. In some embodiments, Factor VIII is pegylated at a surface exposed amino acid of Factor VIII, preferably a surface exposed cysteine, which may be an engineered cysteine. Mei et al. (2010). In some embodiments, modified Factor VIII, e.g., pegylated Factor VIII, is a long-acting Factor VIII.

"Volume of distribution at steady state (Vss)," as used herein, has the same meaning as the term used in pharmacology, which is the apparent space (volume) into which a drug distributes. Vss=the amount of drug in the body divided by the plasma concentration at steady state.

"About," as used herein for a range, modifies both ends of the range. Thus, "about 10-20" means "about 10 to about 20."

Having now described the present invention in detail, the same will be more clearly understood by reference to the following examples, which are included herewith for purposes of illustration only and are not intended to be limiting of the invention. All patents and publications referred to herein are expressly incorporated by reference.

Example 1

Abstract

A recombinant B-domain-deleted factor VIII-Fc (rFVIIIFc) fusion protein was created to extend the half-life of FVIII, rFVIIIFc was studied in mouse and dog models of severe hemophilia A and compared to rFVIII (REFACTO®). Whole blood clotting time (WBCT) in hemophilia A mice was corrected for approximately two to three times longer and the elimination half-life in plasma was nearly twice as long for rFVIIIFc compared to REFACTO®. In hemophilia A dogs, an intravenous dose of rFVIIIFc (125 IU/kg) corrected the WBCT to normal. The WBCT remained below 20 min, the time consistent with FVIII:C>1%, through approximately 96 hr, compared to 48 hr for dogs treated with REFACTO®. The elimination half-life of rFVIIIFc in dog plasma, when measured using ELISA or chromogenic activity assays, was 15.7±1.7 hr and 15.4±0.3 hr, respectively. REFACTO® corrected WBCT for approximately one half as long as rFVIIIFc and the plasma half-life was 7.0 hr. Thus, fusion of FVIII to Fc produced a molecule with an increased plasma half-life and the ability to provide prolonged protection from bleeding.

Introduction

Reduced mortality, prevention of joint damage and improved quality of life have been important achievements due to the development of plasma-derived and recombinant FVIII. Prolonged protection from bleeding would represent another key advancement in the treatment of hemophilia A patients. The inventors have created a recombinant factor VIII-Fc (rFVIIIFc) chimeric protein and hybrid as an approach to extend the half-life of FVIII.

rFVIIIFc is a heterodimeric hybrid protein comprised of B-domain-deleted FVIII fused recombinantly to the Fc domain of human immunoglobulin G1 (IgG1) (FIG. 1, SEQ ID NO:2; Table 2A) (This protein is also referred to herein as FVIIIFc monomeric Fc fusion protein. FVIIIFc monomer hybrid, monomeric FVIIIFc hybrid, and FVIIIFc monomer-dimer). The Fc enables binding to the neonatal Fc receptor (FcRn), which is responsible for protection of IgG from degradation and confers on IgG the three week half-life observed in humans (Ghetie V, and Ward E S., Annu. Rev. Immunol. 2000:18:739-766; Roopenian D C, and Akilesh S., Nature Rev. Immunol. 2007; 7:715-725, each of which is incorporated herein by reference in its entirety).

The Fc domain of IgG1 has been fused to growth factors, cytokines, enzymes and ligand-binding regions of receptors (Ashkanazi A, et al., Int. Rev. Immunol. 1993:10:219-27; Chamow S M, and Ashkanazi A, Trends Biotechnol. 1996: 14:52-60: Fisher et al., N. Engl. J. Med. 1996:334(26):1697-702, each of which is incorporated herein by reference in its entirety). Several of these have become important therapeutic molecules (e.g. etanercept, alefacept, abatacept). In these fusion proteins, two effector molecules are connected to two Fc molecules. In this example, rFVIIIFc has been constructed as a monomeric Fc fusion protein (one copy of a polypeptide consisting of the sequence in Table 2A(i) (SEQ ID NO:2) with or without the signal sequence and one copy of a polypeptide consisting of the sequence in Table 2A(ii) (SEQ ID NO:4) with or without the signal sequence), i.e., with only one copy of the effector molecule (see FIG. 1), and the studies presented herein compare the pharmacodynamics and pharmacokinetics of this novel protein to rFVIII in mouse and dog models of hemophilia A. The signal sequence is cleavage during secretion. This protein construct is referred to herein as FVIIIFc monomeric Fc fusion protein, FVIIIFc monomer hybrid, monomeric FVIIIFc hybrid, and FVIIIFc monomer-dimer. See Example 1, FIG. 1, Table 2A; and U.S. Pat. Nos. 7,404.956 and 7,348,004, each of which is incorporated herein by reference in its entirety, for the structure and production of this protein.

Methods and Materials

FVIII Preparations

Recombinant FVIIIFc

The coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion was from serine 743 (S743; 2287 bp) to glutamine 1638 (Q1638; 4969 bp) for a total deletion of 2682 bp See Example 1, FIG. 1, Table 2A; and U.S. Pat. Nos. 7,404,956 and 7,348,004, each of which is incorporated herein by reference in its entirety, for the structure and production of this protein.

The coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter. A second identical Fc sequence including the mouse Igk signal sequence was obtained by RT-PCR and cloned downstream of the second promoter, EF1α, in the expression vector pBUDCE4.1.

The rFVIIIFc expression vector was transfected into human embryonic kidney 293 cells (HEK293H; Invitrogen) using Lipofectamine 2000 transfection reagent (Invitrogen). Stable clonal cell lines were generated by selection with Zeocin (Invitrogen). One clonal cell line, 3C4-22 was used to generate FVIIIFc for characterization in vivo. Recombinant FVIIIFc was produced and purified (McCue J T, et al., J. Chromatogr. A 2009; 7824-7830, incorporated by reference herein in its entirety) at Biogen Idec (Cambridge, Mass.). The transfection strategy described above was expected to yield three products, i.e., monomeric rFVIIIFc hybrid, dimeric rFVIIIFc hybrid and dimeric Fc. However, there was essentially no dimeric rFVIIIFc detected in the conditioned medium from these cells. Rather, the conditioned medium contained Fc and monomeric rFVIIIFc. It is possible that the size of dimeric rFVIIIFc was too great and prevented efficient secretion from the cell. This result was beneficial since it rendered the purification of the monomer less complicated than if all three proteins had been present. The material used in these studies had a specific activity of approximately 9000 IU/mg. In addition, these human cells produced higher protein level than other cells that were attempted in this experiment.

Recombinant FVIII

Recombinant B-domain deleted FVIII (REFACTO®) was purchased from Novis Pharmaceuticals and was prepared according to manufacturer's instructions. REFACTO® (recombinant B-domain deleted FVIII) has the same amino acid sequence as amino acids 1 to 1438 of SEQ ID NO:2.

Hemophilia a Animals

The hemophilia A mice are FVIII exon 16 knockouts on a 129×B6 background that were obtained from Dr. Kazazian at the University of Pennsylvania (Bi L, et al., Nat. Genet. 1995:10(1):119-121, incorporated by reference herein in its entirety) and bred at Syntonix. These mice exhibit prolonged whole blood clotting times (>60 min), and are thus a good model of severe hemophilia A.

Hemophilia A dogs were from the in-bred colony maintained at the Francis Owen Blood Research Laboratory at the University of North Carolina, Chapel Hill (Graham, J B, et al., J. Exp. Med. 1949; 90:97-111, incorporated by reference herein in its entirety). These dogs have a severe hemophilic phenotype comparable to the severe form of the human disease (Graham, J B, et al., J. Exp. Med. 1949:90: 97-111; Lozier, J N, et al., Proc. Natl. Acad. Sci. 2002:99: 12991-12996, each of which is incorporated by reference herein in its entirety).

Study Designs

Hemophilia A Mouse Studies

The effect of rFVIIIFc and REFACTO® on whole blood clotting time (WBCT) was studied in FVIII-deficient mice. Each protein was administered intravenously at 50 IU/kg and blood was collected from the tail vein of each mouse pre-dose and various time points post-dosing. The blood samples were incubated in microtubes at 37° C., and visually inspected once per minute for the presence of a clot. Time of clot formation was recorded. If no clot formed by 60 min, the clotting time was recorded as >60 min. Blood from normal mice clots in approximately 4 min (range 2-7 min, n=10 mice) in the WBCT assay.

In a second set of studies, hemophilia A mice were administered a single intravenous dose of 50 IU/kg rFVIIIFc, REFACTO® or ADVATE® (4 mice per time point). Blood was collected by cardiac puncture in one tenth volume 3.2% sodium citrate at 0.25, 8, 24, 48 and 72 hr after dosing. Plasma was prepared and stored at −80° C. until analysis for FVIII activity using a FVIII-specific chromogenic activity assay.

Hemophilia A Dog Studies

In a single dose PK/PD study of rFVIIIFc, two hemophilia A dogs from the Chapel Hill colony were administered a single intravenous dose of 125 IU/kg and blood samples were collected pre-dose and after dosing at selected time points for WBCT, activated partial thromboplastin time (aPTT), FVIIIFc plasma concentration, hematology and serum chemistry. Time points for WBCT included pre-dose. 5 and 30 min and 1, 2, 4, 8, 24, 32, 48, 72, 96, 144, and 168 hr after dosing. Blood collections for clotting activity (aPTT) and FVIIIFc plasma concentration included the time points listed above for WBCT as well as 15 min and 3, 6, 12 hours after dosing.

A second study was conducted in which REFACTO® (114 IU/kg for dog M12 and 120 IU/kg for dog M38) was administered intravenously. WBCT was measured until clotting times were >20 min (consistent with FVIII:C>1%), and then 125 IU/kg rFVIIIFc was administered intravenously to the same dogs and blood samples were collected for WBCT, aPTT, FVIIIFc plasma concentration, hematology and serum chemistry. Time points for WBCT included pre-dose, 5 and 30 min and 1, 2, 4, 8, 24, 32, 48, 72 hr after dosing. Blood was also collected at 96, 120, 144, and 168 hr after dosing with FVIIIFc. Blood collections for clotting activity and FVIIIFc plasma concentration included the time points listed above for WBCT as well as 15 min and 3, 6, 12 hours after dosing.

The WBCT procedure in hemophilia A dogs was slightly different than that in the hemophilia A mice. After dosing with rFVIIIFc or REFACTO®, one mL of blood was collected at various time points and 0.5 mL was distributed into two siliconized glass tubes which were subsequently placed into a 28° C. water bath. Beginning at one minute, one tube was tilted every 30 sec, the second left undisturbed. When a clot formed in the tilted tube, the second tube was then tilted every 30 sec until a clot formed. The time for a fully gelled clot in the second tube was recorded as the WBCT.

FVIII Activity in Plasma

Measurement of FVIII activity in plasma by FVIII-specific chromogenic assay

Plasma samples were tested for FVIII activity by an automated chromogenic method using a Sysmex CA1500 instrument and reagents were from Siemans Healthcare Diagnostics (Dallas, Tex., kit #B4238-40). Activity of rFVIIIFc was determined using a standard curve created using the 7th International Standard Factor FVIII Concentrate (NIBSC code 99/678) spiked into human FVIII-depleted plasma (Stago USA) at concentrations ranging from 1.5-0.016 IU/mL.

Measurement of rFVIIIFc or FVIII by ELISA

FVIIIFc in Dog Plasma by ELISA

A FVIII antibody specific to the A1 domain (Green Mountain Antibodies: GMA-8002) was coated on 96 well plates and incubated for 1 hr at 37° C. The coated plates were blocked with Tris-buffered saline containing Tween 20, $CaCl_2$ and bovine serum albumin for 1 hr at room temperature and then standards, controls and samples that were prepared in normal dog plasma, were diluted 1:10 and then added to the plates and incubated for 1 hour at 37° C. The plates were washed and then donkey $(F(ab)'_2)$ anti-human Fc-HRP (Jackson: 709-036-098) was added and incubated for 1 hr at 37° C. After washing, TMB (BioFx supersensitive substrate: TMBS-0100-01) was added to the plates, the substrate reaction was quenched with acid and absorbance was measured on a SpectraMax Plus plate reader (Molecular Devices) at 450 nm.

REFACTO® in dog plasma by ELISA

An anti-FVIII antibody specific to the A1 domain on the heavy chain (Green Mountain Antibodies: GMA-8002) was coated on 96 well plates and incubated for 2 hr at room temperature. The coated plates were blocked for 1 hr at 37° C. and after washing, the standards, controls and samples were prepared in normal dog plasma then diluted 1:10 were added to the plates and incubated for 2 hr at room temperature. The plates were washed then treated with the detection antibody, a pre-diluted anti-FVIII horse radish peroxidase conjugate (Affinity Biologicals: F8C-E1A-D), and incubated at room temperature for 1 hr. After washing TMB (BioFx supersensitive substrate: TMBS-0100-01) was added to the plates for 10 min. The substrate reaction was quenched with acid and the signal was measured on a SpectraMax Plus plate reader (Molecular Devices) at a wavelength of 450 nm.

Measurement of Fibrinogen

The concentration of fibrinogen in plasma was measured at Esoterix (Research Triangle Park, N.C.) using a kit that contains HemosIL™ PT-Fibrinogen-HS reagent (Instrumentation Laboratory, Lexington, Mass., Catalog #0008468210) and an ACL 7000 Coagulation Analyzer (Beckman Coulter), according to the manufacturer's instructions.

Measurement of Platelets

Platelets were counted in EDTA anti-coagulated whole blood by automated methods using the Vet-ABC-Diff Hematology Analyzer programmed with a species specific smart card (SCIL Animal Care Co., Gurnee, Ill.).

Pharmacokinetic Analysis

The pharmacokinetic parameters were calculated by non-compartmental analysis using WinNonlin software from Pharsight, version 5.2 (Mountain View, Ca). PK parameters included the maximum concentration in plasma ($C_{max}$), area under the plasma concentration versus time curve (AUC), elimination half-life ($t_{1/2}$), volume of distribution (Vss), and clearance (Cl).

Results

Recombinant FVIII-Fc rFVIIIFc is a recombinant fusion of human B-domain deleted FVIII with Fc from human IgG1, with no intervening linker sequence (rFVIIIFc; FIG. 1).

Purified rFVIIIFc had a specific activity of approximately 9000 IU/mg as determined using a chromogenic activity assay. Recombinant B-domain deleted FVIII (REFACTO®) has a reported specific activity of 9110-13700 IU/mg. Conversion of specific activity into IU/nmol to take into account the size difference between FVIIIFc and REFACTO® (216 kDa and 170 kDa respectively), indicates that the two proteins have approximately equivalent specific activities (1970 IU/nmol for rFVIIIFc and 1521-2287 IU/nmol for REFACTO®). Thus the FVIII activity of rFVIIIFc is not affected by fusion of the C-terminus of human FVIII to the N-terminus of human Fc.

Administration to Hemophilia a Mice

A single 50 IU/kg dose of rFVIIIFc or REFACTO® was administered intravenously to FVIII-deficient mice (n=6/group). Blood samples were collected pre-dose and after dosing through 120 hr and WBCT determined as described in Materials and Methods. Baseline WBCT were greater than 60 min. Data from a representative experiment are shown in FIG. 2 and Table 3. Immediately after dosing with either rFVIIIFc or REFACTO®, WBCT was corrected to 2-17 minutes. Blood from mice treated with REFACTO® lost the ability to clot by 42 hr, whereas blood from all mice treated with rFVIIIFc still clotted at 96 hr, the blood from one of six was clotted at 113 hr, but all had lost the ability to clot by 120 hr. These data suggest that the duration of effect for rFVIIIFc is approximately two to three times longer than for REFACTO®.

The chromogenic activity of rFVIIIFc, REFACTO® or ADVATE® (full-length recombinant FVIII) was studied in the FVIII-deficient mice after a single intravenous dose of 50 IU/kg. Blood was collected pre-dose and after dosing at 8, 24, 48, and 72 hr. The activity was measured using a FVIII-specific chromogenic activity assay and is shown in FIG. 3. The pharmacokinetic parameters are reported in Table 4. The circulating half-life for rFVIIIFc was approximately 1.6 to 2 fold longer (11.1 hr) compared to ADVATE® (7 hr) and REFACTO® (5 hr). The Cmax was 1.6±0.36 IU/mL for rFVIIIFc compared to 0.47±0.30 IU/mL for ADVATE® and 0.67±0.44 IU/mL for REFACTO®. The systemic exposure of rFVIIIFc was markedly greater for rFVIIIFc (22.6 hr·IU/mL) compared to REFACTO® (6.94 hr·IU/mL) and ADVATE® (3.90 hr·IU/mL) and clearance for rFIIIFc was notably lower (2.09 mL/hr/kg) compared to both REFACTO® (7.2 mL/hr/kg) and ADVATE® (12.8 hr/mL/kg) in the hemophilia A mice.

Administration to Hemophilia a Dogs

The pharmacodynamics (PD) and pharmacokinetics (PK) of rFVIIIFc were studied in the Chapel Hill colony of hemophilia A dogs. A single intravenous dose of 125 IU/kg rFVIIIFc was administered to each of four hemophilia A dogs and the WBCT was immediately corrected to normal (FIG. 4). The range of WBCT in normal dogs is 8-12 min. The WBCT remained below 20 min, the time consistent with FVIII:C>1%, through approximately 96 hr with the exception of one dog that had WBCT <20 min through 72 hr. In addition, aPTT was also immediately corrected to normal (Table 6). The concentration of rFVIIIFc in plasma was measured using a specific ELISA which was designed to detect both the FVIII and Fc portions of the molecule. The plasma concentration versus time curves are shown in FIG. 5. PK analysis of the data showed that the $t_{1/2}$ was 15.7±1.7 hr (Table 5). Similar results were obtained when rFVIIIFc was measured using a FVIII-specific chromogenic activity assay ($t_{1/2}$=15.4±0.3 hr, Table 5) and the plasma concentration versus time curves were similar using both methods (FIG. 5 and FIG. 6). When the activity data were converted from IU/mL to ng/mL using the specific activity for rFVIIIFc, there was a good correlation with the ELISA data, thereby demonstrating that the protein that was measured by ELISA was fully active.

Two of the dogs treated with rFVIIIFc also received a single dose of REFACTO®, 114 IU/kg for dog M12 and 120 IU/kg for dog M38, 72 hr prior to dosing with rFVIIIFc. WBCT and aPTT were corrected to normal immediately after dosing with REFACTO®. However, the WBCT normalization after the single dose of rFVIIIFc lasted approximately twice as long compared to REFACTO® (FIG. 4). Moreover, the plasma half-life of rFVIIIFc (15.7±1.7 hr) was approximately twice as long for rFVIIIFc compared to REFACTO® (7.0 and 6.7 hr) when the concentration of the proteins in plasma were measured by ELISA (Table 5). Similar results were obtained when the two molecules were measured by FVIII-specific chromogenic activity.

To assess the potential risk of thrombogenicity, platelets and fibrinogen were measured. After dosing with either rFVIIIFc or REFACTO®, platelet numbers and plasma fibrinogen concentration did not change from pre-dose values (data not shown).

Discussion

Recombinant FVIIIFc was produced in human embryonic kidney 293 (HEK 293) cells from a stably transfected cell line and was purified from cell culture medium. Production in a human cell line represents a significant change in manufacturing compared to currently marketed rFVIII products which are produced in either Chinese Hamster Ovary cells or Baby Hamster Kidney cells. The rationale for this change was that it was expected that the human cells were best equipped to perform the necessary post-translational modifications for the FVIII portion of this molecule.

Conversion of the specific activity to IU/nmol to take into account the difference in molecular weights for rFVIIIFc and recombinant B-domain deleted FVIII (REFACTO®) indicated that the specific activities are similar for both proteins (1970 IU/nmol for rFVIIIFc and 1521-2287 IU/nmol for REFACTO®). It is somewhat surprising that the specific activity for rFVIIIFc is not affected by fusion of the C terminus of FVIII with the N-terminus of Fc since the C1 and C2 domain of FVIII are involved in phospholipid binding which is essential for full FVIII activity (Fay, P J, J. Hematology 83:103-8 (2006) and Raut, S, et al., Br. J. Haematol. 107:323 (1999), each of which is incorporated by reference herein in its entirety).

Treatment of hemophilia A is on-demand at the time of a bleeding episode or by prophylaxis for the prevention of bleeding. Although on-demand treatment is still frequently used, there is a trend toward prophylaxis and the prevention of joint damage (Blanchette P, et al., Haemophilia 2004: 10; 679-683, Manco-Johnson, M J, et al., N. Engl. J. Med. 2007:357:535-544, each of which is incorporated by reference herein in its entirety). Current FVIII products are administered every two to three days for prophylaxis due to the relatively short half-life of 10-12 hr in order to maintain a FVIII:C above 1% in patients (Morfini, M, Haemophilia 2003; 9 (suppl 1):94-99; discussion 100, White G C, et al., Thromb. Haemost. 1997:77:660-7, Blanchette, P, et al., J. Thromb. Haemost. 2008 August; 6(8): 1319-26, each of which is incorporated by reference herein in its entirety). Longer-acting FVIII therapies that provide prolonged protection from bleeding would represent a marked improvement in the quality of life for patients with hemophilia A. Strategies to extend the half-life of clotting factors include those that have been successful for other molecules, including pegylation (Rostin J, et al., Bioconj. Chem. 2000; 11:387-96, incorporated by reference herein in its entirety), glycopegylation (Stennicke H R, et al., Thromb. Haemost. 2008; 100:920-8, incorporated by reference herein in its entirety), formulation with pegylated liposomes (Spira J, et al., Blood 2006:108:3668-3673, Pan J, et al., Blood 2009: 114:2802-2811, each of which is incorporated by reference herein in its entirety) and conjugation with albumin (Schulte S., Thromb. Res. 2008; 122 Suppl 4:S14-9, incorporated by reference herein in its entirety). Pegylation represents an approach to reduce clearance, however, the effect of the modification in vivo is currently unknown. The outcome of direct pegylation of FVIII on in vivo is currently unknown, whereas FVIII formulated with pegylated liposomes has been studied clinically and showed a modest to no effect on bleeding periods (Spira J, et al., Blood 2006; 108:3668-3673, Spira J, et al., Thromb. Haemost. 2008 September; 100(3):429-34, each of which is incorporated by reference herein in its entirety).

The present approach to extend the half-life of FVIII was to recombinantly fuse FVIII to the Fc domain of IgG1. Fc binds to the naturally occurring receptor, FcRn, of which the normal function is protection of IgG from degradation. The results described herein represent the initial pharmacokinetic and efficacy characterization of rFVIIIFc compared to a rFVIII product in hemophilia A mice and hemophilia A dogs. In both species, the half-life of rFVIIIFc was approximately twice that of rFVIII when measured by FVIII activity or ELISA (dogs only). These data also correlated well with the WBCT results from both animal models, i.e. the duration of the effect of rFVIIIFc on WBCT was approximately twice as long compared to REFACTO®. In dogs, the Cmax and clearance were similar for rFVIIIFc and REFACTO®, but the AUC and volume of distribution at steady state were approximately 1.5 fold and 2 fold greater for rFVIIIFc compared to REFACTO®, respectively. The PK parameters for REFACTO® in this animal model are consistent with the values reported in the literature (Brinkhous K, et al., Sem. Thromb. Haemost. 2002; 28:269-272, incorporated by reference herein in its entirety).

If these findings translate to the same extension of half-life in humans, this could represent a significant advancement in the treatment of patients with hemophilia A.

ADDITIONAL REFERENCES (EACH OF WHICH IS INCORPORATED HEREIN BY REFERENCE IN ITS ENTIRETY)

Berkner K., Methods Enzymol. 1993:222:450-477.
Bitonti A J, and Dumont J A., Adv. Drug Del. Rev. 2006; 58:1106-1118.
Dumont J A, et al., J. Aerosol Med. 2005; 18:294-303.
Dumont J A, et al., BioDrugs 2006:20:151-160.
Ellis C N, and Krueger G G., N. Engl. J. Med. 2001; 345:248-55.
Low S C, et al., Hum Reprod. 2005:7:1805-1813.
Manco-Johnson, M., Haemophilia 2007; 13 Suppl; 2: 4-9.
Mannucci, P M, and Tuddenham. EGD., N. Engl. J. Med. 2001; 344:1773-1779.
Peyvandi F, et al., Haemophilia 2006; 12(Suppl 3):82-89.
Rodriguez-Merchan, E C., Semin. Thromb. Hemost. 2003; 29:87-96.
Srour M A, et al., Ann. Hematol. 2008; 87:107-12.

Example 2

The objective of the study was to determine the pharmacokinetics and pharmacodynamics of rFVIIIFc and BDD-rFVIII (XYNTHA®) in cynomolgus monkeys after a single intravenous dose.

Materials and Methods rFVIIIFc (Biogen Idec), supplied as a frozen liquid at a concentration of 1.2 mg/mL, and 9882 IU/mL. The specific activity is 8235 IU/mg. Storage was at −70° C. It was diluted prior to injection.

Name: XYNTHA® (Novis Pharmaceuticals), Supplied as a lyophilized powder which was reconstituted according to the manufacturer's instructions to produce a solution with a nominal concentration of 525 IU/mL. Storage was according to the manufacturer's recommendations.

Animals

Cynomolgus monkeys from the New Iberia Research Center (NIRC) colony were used, and the study (NIRC Study #8733-0903) was conducted under an approved NIRC IACUC protocol (APS 2008-8733-058) at NIRC in New Iberia, La.

Six naïve cynomolgus monkeys (three males, three females) that were determined to be in good health were used in the study.

The study was performed in compliance with the protocol and UL Lafayette-NIRC Standard Operating Procedures.

Study Design rFVIIIFc was administered intravenously at 125 IU/kg to each of six monkeys (three males, three females). XYNTHA® (BDD-rFVIII) was administered intravenously to the same animals at 125 IU/kg in a crossover design. Group 1 animals (n=3) received XYNTHA® on Day 0 and rFVIIIFc on Day 3, while Group 2 animals (n=3) received rFVIIIFc on Day 0 followed by XYNTHA® on Day 4. The additional day between doses for group 2 was to ensure that the rFVIIIFc had sufficient time to decrease below projected baseline levels. Blood was collected for plasma in one-tenth volume 3.2% sodium citrate from each animal predose and after dosing at 0.25, 4, 12, 24, 36, 48 and 72 hr for measurement of rFVIIIFc or XYNTHA® by ELISA and a FVIII-specific chromogenic activity assay.

ELISA to Measure rFVIIIFc and FVIII in Plasma

Method to Measure rFVIIIFc in Monkey Plasma

This Enzyme Linked ImmunoSorbent Assay (ELISA) is designed to quantify rFVIIIFc in monkey plasma. In this ELISA method, goat anti-human IgG-(H+L) antibody (monkey absorbed) from Bethyl Laboratories (Cat#A80-319A) is diluted in Coating Buffer and immobilized onto a 96-well microtiter sample plate. The plate is aspirated, and all un-adsorbed sites are blocked with the addition of Blocking Buffer (3% BSA/1×Tris) for approximately 2 hours at 37° C.

Plasma samples are diluted 1:20 with High Calcium Sample Dilution Buffer (3% Non-Fat Dry Milk/TBST with 30 mM $CaCl_2$)) and dispensed onto the sample plate. Plates are incubated for approximately 2 hours at 37° C. The plate is subsequently washed and mouse anti-B domain-deleted (α.BDDA1) Factor VIII (A1 domain) antibody from Green Mountain Antibodies (Cat#GMA-8002) is added to the plate and incubated for approximately 1 hour at 37° C. After washing the plate, HRP-conjugated goat anti-mouse IgG2a antibody from Southern Biotech (Cat#1080-05) is added to the plate and incubated for approximately 30 minutes at room temperature. The plate is washed again and a tetramethylbenzidine (TMB) peroxidase substrate solution is added and incubated for approximately 30 minutes at room temperature. The reaction is stopped by addition of a non-acidic Stop Solution. Color develops in proportion to the amount of rFVIIIFc in the sample. Plates are read on an absorbance plate reader using a single detection wavelength, 650 nm, rFVIIIFc concentrations are determined on a standard curve obtained by plotting optical density (OD) versus concentration using a four-parameter logistic curve-fitting program. The calibration curve range of this method is 0.400 ng/mL-51.2 ng/mL in 5% monkey plasma (8.00 ng/mL-1024 ng/mL in 100% monkey plasma). One calibrator outside the qualified range of the assay at 0.200 ng/mL in 5% monkey plasma may be included to serve as an anchor point to facilitate curve-fitting. The anchor point is removed or retained based on the best fit of the curve (i.e., the highest number of standards read within defined accuracy, % RE).

Method to Measure FVIII in Monkey Plasma

This Enzyme Linked ImmunoSorbent Assay (ELISA) is designed to quantify FVIII in monkey plasma. In this ELISA method, mouse aBDDA1 FVIII antibody from Green Mountain Antibodies (Cat# GMA-8002) is diluted in Coating Buffer and immobilized onto a 96-well microtiter sample plate. The plate is aspirated, and all un-adsorbed sites are blocked with the addition of Blocking Buffer (3% BST/1× Tris) for approximately 1 hour at 37° C. Plasma samples are diluted 1:20 with High Calcium Sample Dilution Buffer (Blocking Buffer with 100 mM $CaCl_2$)) and dispensed onto the sample plate. Plates are incubated for approximately 2 hours at 37° C. After washing the plate, a Detecting Antibody from the Affinity Biologicals Kit, an HRP labeled polyclonal antibody (Cat#F8C-E1A-D), is further diluted in TBS/0.05% Tween 20, and added to the plate and incubated for approximately 1 hour at room temperature. The plate is washed again and a tetramethylbenzidine (TMB) peroxidase substrate solution is added and incubated for approximately 30 minutes at room temperature. The reaction is stopped by addition acidic Stop Solution. Color develops in proportion to the amount of FVIIIFc in the sample. Plates are read on an absorbance plate reader using a single detection wavelength, 450 nm. FVIII concentrations are determined on a standard curve obtained by plotting optical density (OD) versus concentration using a four-parameter logistic curve-fitting program. The calibration curve range of this method is 0.625 ng/mL-20 ng/mL in 5% monkey plasma (12.5 ng/mL-400 ng/mL in 100% monkey plasma). Two calibrators outside the qualified range of the assay at 0.313 and 0.156 ng/mL in 5% monkey plasma may be included to serve as anchor points to facilitate curve-fitting. The anchor points can be removed or retained based on the best fit of the curve (i.e., the highest number of standards read within defined accuracy, % RE).

FVIII-Specific Chromogenic Assay

FVIII activity in cynomolgus monkey plasma samples was estimated based on administered dose, and then diluted to approximately 0.25-1 IU/ml in human FVIII-depleted plasma (Diagnostica Stago). Samples were analyzed in a Sysmex CA1500 (Siemens Diagnostic Healthcare) using a FVIII chromogenic kit (Siemens). In this chromogenic assay, rFVIIIFc in the plasma samples is activated by thrombin. Activated Factor VIII (FVIIIa) then accelerates the conversion of Factor X (FX) to Factor Xa (FXa) in the presence of activated Factor IX (FIXa), phospholipids (PL) and calcium ions. The FXa activity is assessed by hydrolysis of a p-nitroanilide substrate specific to FXa. The initial rate of release of p-nitroaniline (pNA) measured at 405 nm is proportional to the FXa activity, and thus to the FVIII activity in the sample. The limit of quantitation of FVIII activity due to rFVIIIFc in this assay is 0.3 IU/ml. The assay can measure total FVIII activity down to a lower limit of approximately 0.06 IU/ml with an accuracy of +20%. The calculated activity of the pre-dose sample for individual animals was subtracted from the value at each time point to generate the PD curves (FVIII activity vs. time).

A standard curve was generated from the NIBSC 7th International Standard FVIII concentrate diluted to 1 IU/ml in human FVIII-deficient plasma. Standard curves were diluted serially in the Sysmex instrument to yield concentrations of 0.15, 0.1, 0.05, 0.025, 0.0053 and 0.0026 IU/ml. Since the instrument dilutes all samples 1:10 internally, the FVIII standard concentrations correspond to plasma concentrations of 1.5-0.026 IU/ml, which is the range of FVIII activities that can be measured.

PK Analysis

The concentration time profiles were evaluated using the non-compartmental analysis module in the WinNonlin software program (Version 5.2, Pharsight Corporation, Mountain View, Calif.).

Results

The concentration of rFVIIIFc in monkey plasma was measured using a sandwich ELISA format that measured both the FVIII and Fc portions of the molecule and the data are reported in Table 7. All predose samples were below the limit of quantitation. FIG. 7 illustrates the group mean rFVIIIFc and XYNTHA® plasma concentrations over time and individual plasma concentration versus time curves are shown in FIGS. 8A-8B. A summary of the PK parameters for rFVIIIFc and XYNTHA® are shown in Tables 9 and 10, respectively. The mean t1/2 for rFVIIIFc was 11.9±1.7 hr (range 9.3 to 14.1 hr) and for XYNTHA®, the mean elimination t1/2 was 12.7±4.4 hr (range 9.2 to 19.9 hr).

FVIII activity was measured using a FVIII-specific chromogenic activity assay and the data are reported in Table 8. Pre-dose activity due to endogenous FVIII was subtracted from all samples. A graph of the mean group data is shown in FIG. 9 and the individual plasma concentration vs. time curves are shown in FIGS. 10A-10B. A summary of the PK parameters are reported for rFVIIIFc and XYNTHA® in Tables 9 and 10, respectively. The mean elimination t1/2 was 16.1±6.9 hr (range 11.6 to 29.4 hr) for rFVIIIFc and 12.5±1.7 hr (range 10.4 to 14.3 hr) for XYNTHA®.

Discussion and Conclusions

The elimination half-lives were similar for rFVIIIFc and XYNTHA® after a single intravenous dose of 125 IU/kg, whether the test article was measured by ELISA or a chromogenic activity assay.

Example 3

This will be a Phase I/IIa, open-label, crossover, dose-escalation, multi-center, and first-in-human study designed to evaluate the safety, tolerability, and pharmacokinetics of a single dose of rFVIIIFc in subjects with severe (defined as <1 IU/dL [1%] endogenous factor VIII [FVIII]) hemophilia A. A total of approximately 12 previously treated patients will be enrolled and dosed with rFVIIIFc at 25 or 65 IU/kg. After the screening (scheduled within 28 days prior to the first dose of the ADVATE® [rFVIII], the reference comparator agent) and a minimum of 4-days (96 hours) elapsing with no FVIII treatment prior to the first injection, approximately 6 subjects will receive a single 25 IU/kg dose of ADVATE® followed by a 3-day (72 hours) pharmacokinetic (PK) profile then crossover and receive a 25 IU/kg single, open-label dose of rFVIIIFc for a 7-day (168 hours) PK profiling. The first 3 subjects will be dosed sequentially. For the first three (3) subjects dosed with 25 IU/kg of rFVIIIFc, each subject will undergo an inhibitor assessment at 14-days (336 hours) post-injection of rFVIIIFc. Dosing of the next subject (for the first three subjects only) will occur once the inhibitor testing is completed. After the 3rd subject completed the 14 day inhibitor assessment, the remaining three subjects at 25 IU/kg and the six subjects at 65 IU/kg will begin enrollment sequentially at least 1 day apart within each dose group.

One week after the last subject receives the 25 IU/kg dose of the rFVIIIFc, approximately 6 unique subjects will be recruited for the 65 IU/kg cohort. Each subject in the 65 IU/kg cohort will receive a single 65 IU/kg dose of ADVATE® followed by a 4-day (96 hours) PK profiling then crossover and receive a 65 IU/kg single, open-label dose of rFVIIIFc for a 10-day (240 hours) profiling. If a bleeding episode occurs before the first injection of rFVIIIFc in any cohort, subject's pre-study FVIII product should be used for treatment and an interval of at least 4 days must then pass before receiving the first injection of rFVIIIFc for the PK profile.

All subjects will be followed for a 14-day (336 hours) and 28 day safety evaluation period after administration of rFVIIIFc 25 IU/kg or 65 IU/kg for safety. All subjects will undergo pharmacokinetic sampling pre- and post-dosing along with blood samples for analysis of FVIII activity at designated time points.

Example 4

Activity within the Xase Complex

To investigate the binding of the FVIII proteins (rBDD FVIII and rFVIIIFc) with FIXa, and measure the ability of these proteins to activate FX, kinetic studies were performed examining these interactions in the context of the Xase complex. This assay involved the formation of the Xase complex with activated FIX and activated rBDD FVIII or rFVIIIFc protein on a phospholipid surface in the presence of calcium, and monitoring the conversion of FX to FXa as measured by cleavage of a chromogenic or fluorogenic substrate.

Briefly, FVIII is first activated with α-thrombin for 5 min, then mixed with FIXa in the presence of Ca2+, and synthetic phospholipid vesicles (25% phosphatidylserine (PS)/75% phosphatidylcholine (PC)) or platelets. Under conditions described below, FVIIIa and FIXa interact in the presence of a phospholipid surface and calcium ions to form an active Xase complex that mediates the conversion of FX into FXa through proteolytic processing. In turn, FXa cleaves a FXa-specific chromogenic or fluorogenic substrate. The cleaved substrate is chromogenic and therefore the amount of cleaved substrate in a solution is indicative of the amount of FXa generated. This is quantitated by measuring the absorbance of the solution at 405 nm.

A. Activation of Factor X

The ability of rBDD FVIII and rFVIIIFc to activate FX were studied in the context of the Xase complex as described above. Thrombin-activated FVIII proteins were incubated with FIXa and phospholipids in the presence of calcium, then added to different concentrations of FX in the presence of a FX-specific substrate and the rates of FXa generation determined (FIG. 11).

Based on these data, the Km and Vmax for the different FVIII proteins in the context of the Xase complex were calculated (Chang 1997) (Table 11). Data are expressed as the mean of six analyses (3 experiments containing duplicate runs)±the corresponding standard deviation. Based on these data, these proteins (rBDD FVIII and rFVIIIFc) were found to have comparable Km and Vmax values, within the variation of the assay. Therefore, the Xase complex formed with rFVIIIFc behaves similarly to the Xase complex formed with the licensed product rBDD FVIII (REFACTO®) with respect to interactions with phospholipids and ability to activate FX. Note that these comparable data also demonstrate that rFVIIIFc is activated to a comparable degree as rBDD FVIII after a short incubation with thrombin.

B. Interaction with FIXa

The interaction between rBDD FVIII and rFVIIIFc with FIXa were also examined in the context of the Xase complex. The Xase complex was assembled as above, using a fixed amount of FX and varying FIXa levels, and FXa generation rates determined (FIG. 12). From these data, the Kd value for the Xase complex formed with both of the FVIII proteins to FIXa were determined (Chang 1997). Data are expressed as the mean of six analyses (3 experiments containing duplicate runs)±the corresponding standard deviation (Table 12). Both proteins were found to have similar Kd and Vmax values, indicating that rFVIIIFc has comparable interactions with FIXa as the licensed rBDD FVIII product.

Example 5

Interim pharmacokinetic data for the Phase I/IIa clinical trial discussed in Example 3 demonstrated the following results for FVIIIFc. FVIIIFc had about a 50% increase in systemic exposure (AUC$_{INF}$), about 50% reduction in clearance (Cl), and about 50-70% increase in elimination half-life and MRT compared to ADVATE® (full length rFVIII). In addition, FVIIIFc showed increased C168, TBLP1, TBLP3, and TBLP5 values compared to ADVATE®.

AUC$_{INF}$ Area under the concentration-time curve from zero to infinity
Beta HL Elimination phase half-life; also referred to as $t_{1/2}$=
C168 Estimated FVIIIFc activity above baseline at approximately 168 h after dose
Cl Clearance
MRT Mean residence time
TBLP1 Model-predicted time after dose when FVIIIFc activity has declined to approximately 1 IU/dL above baseline
TBLP3 Model-predicted time after dose when FVIIIFc activity has declined to approximately 3 IU/dL above baseline
TBLP5 Model-predicted time after dose when FVIIIFc activity has declined to approximately 5 IU/dL above baseline Example 6

A recombinant B-domain-deleted factor VIII-Fc (rFVIIIFc) fusion protein has been created as an approach to extend the half-life of FVIII. The pharmacokinetics (PK) of rFVIIIFc were compared to rFVIII in hemophilia A mice. We found that the terminal half-life was twice as long for rFVIIIFc compared to rFVIII. In order to confirm that the underlying mechanism for the extension of half-life was due to the protection of rFVIIIFc by FcRn, the PK were evaluated in FcRn knockout and human FcRn transgenic mice. A single intravenous dose (125 IU/kg) was administered and the plasma concentration measured using a chromogenic activity assay. The Cmax was similar between rFVIIIFc and rFVIII (XYNTHA®) in both mouse strains. However, while the half-life for rFVIIIFc was comparable to that of rFVIII in the FcRn knockout mice, the half-life for rFVIIIFc was extended to approximately twice longer than that for rFVIII in the hFcRn transgenic mice. These results confirm that FcRn mediates or is responsible for the prolonged half-life of rFVIIIFc compared to rFVIII. Since hemostasis in whole blood measured by rotation thromboelastometry (ROTEM) has been shown to correlate with the efficacy of coagulation factors in bleeding models of hemophilia mice as well as in clinical applications, we sought to evaluate the ex vivo efficacy of rFVIIIFc in the hemophilia A mice using ROTEM. Hemophilia A mice were administered a single intravenous dose of 50 IU/kg rFVIIIFc, XYNTHA® (FVIII) or ADVATE® (FVIII). At 5 minutes post dose, clot formation was similar with respect to clotting time (CT), clot formation time (CFT) and α-angle. However, rFVIIIFc showed significantly improved CT at 72 and 96 hr post dose, and CFT and α-angle were also improved at 96 hrs compared to both XYNTHA® (FVIII) and ADVATE® (FVIII), consistent with prolonged PK of rFVIIIFc. Therefore construction of an Fc fusion of FVIII produces a molecule with a defined mechanism of action that has an increased half-life and the potential to provide prolonged protection from bleeding.

Example 7

This Example presents final analysis results for FVIII activity from 16 patients treated with 25 and 65 IU/kg FVIII products. See Examples 3 and 5.

In this Example, rFVIIIFc is a recombinant fusion protein comprised of a single molecule of recombinant B-domain deleted human FVIII (BDD-rFVIII) fused to the dimeric Fc domain of the human IgG1, with no intervening linker sequence. This protein construct is also referred to herein as rFVIIIFc heterodimeric hybrid protein, FVIIIFc monomeric Fc fusion protein, FVIIIFc monomer hybrid, monomeric FVIIIFc hybrid, and FVIIIFc monomer-dimer. See Example 1, FIG. 1, and Table 2A.

Preclinical studies with rFVIIIFc have shown an approximately 2-fold prolongation of the half-life of rFVIII activity compared to commercially available rFVIII products. The rationale for this study was to evaluate the safety and tolerability of a single dose of rFVIIIFc in frozen liquid formulation and provide data on the PK in severe hemophilia A subjects. For this study, 16 evaluable subjects were available for PK evaluation. Single administration of two doses of both rFVIIIFc and ADVATE® at a nominal dose of 25 (n=6) and 65 IU/kg of body weight (n=10) were infused intravenously over approximately 10 minutes. Blood samples for plasma PK assessments were obtained before infusion, as well as up to 10 days after dosing. The PK of FVIII activity for both ADVATE® and rFVIIIFc were characterized in this study using a model-dependent method.

Objectives

The primary objective of this study was to assess the safety and tolerability of single administration of two doses of rFVIIIFc (25 and 65 IU/kg) in previously treated patients (PTPs) aged 12 and above with severe hemophilia A.

The secondary objectives were to determine the pharmacokinetics (PK) parameters determined by pharmacodynamic (PD) activity of FVIII over time after a single administration of 25 or 65 IU/kg of rFVIIIFc compared to ADVATE® in one-stage clotting and chromogenic assays.

Study Design (See Example 3)

Blood samples were collected for FVIII activity PK evaluations at the screening visit (within 28 days prior to dosing ADVATE®); on Day 0 (injection of ADVATE®) pre-injection and at 10 and 30 minutes and 1, 3, 6, and 9 hours post-injection; on Day 1 at 24 hours post-injection of ADVATE®; on Day 2 at 48 hours post-injection of ADVATE®; on Day 3 at 72 hours post-injection of ADVATE®; and on Day 4 at 96 hours post-injection of high dose of ADVATE® (Cohort B only).

Blood samples were collected for FVIII activity PK evaluations on the day of rFVIIIFc injection just prior to the administration of rFVIIIFc, at 10 and 30 minutes and 1, 3, 6, and 9 hours post-injection of rFVIIIFc; on Day 1 at 24 hours post-injection of rFVIIIFc; on Days 2 through 5 at 48, 72, 96, and 120 hours post-injection of rFVIIIFc; on Day 7 at 168 hours post-injection of rFVIIIFc; on Days 8, 9, and 10 at 192, 216, and 240 hours post-injection of high dose of rFVIIIFc (Cohort B only). FVIII activity was also measured at the final study visit (28 days post-injection of rFVIIIFc) at 672 hours post-injection of rFVIIIFc.

Pharmacokinetic Modeling and Calculations

Abbreviations

TBLP1=Model-predicted time after dose when FVIII activity has declined to approximately 1 IU/dL above baseline.
TBLP3=Model-predicted time after dose when FVIII activity has declined to approximately 3 IU/dL above baseline
KV_M=Cmax_M/Actual Dose (IU/kg)
KV_OB=Cmax_OB/Actual Dose (IU/kg)
IVR_M=100×Cmax_M×Plasma Volume (dL)/Total Dose in IU; where plasma volume in mL=(23.7×Ht in cm)+(9.0× Wt in kg)−1709.
IVR_OB=100: Cmax_OB×Plasma Volume (dL)/Total Dose in IU; where plasma volume in mL=(23.7×Ht in cm)+ (9.0×Wt in kg)−1709.

Results

FIG. 13. Observed group mean (+SE) FVIII activity versus time profiles, sorted by dose level, grouped by compound (one-stage assay, 25 IU/kg (A) and 65 IU/kg (B)) and (chromogenic assay, 25 IU/kg (C) and 65 IU/kg (D)).

FIG. 14. Observed group mean (+SE) FVIII activity versus time profiles, grouped by dose level and compound (one-stage assay; A) (chromogenic assay; B).

Single-Dose Pharmacokinetics (One-Stage Assay)

Observed FVIII activity increased sharply after the short IV infusion of either ADVATE® or rFVIIIFc, with mean (+SD) model-predicted Cmax values of 56.6±4.74 and 121±28.2 IU/dL for ADVATE® and 55.6±8.18 and 108±16.9 IU/dL for rFVIIIFc for the 25 and 65 IU/kg dose groups, respectively. All ADVATE®- and rFVIIIFc-treated patients had dose-related increases in FVIII activity. The observed increase in both Cmax and AUCINF was slightly less than proportional to dose over the dose range evaluated.

After the end of the infusion, the decline of the observed FVIII activity exhibited monoexponential decay characteristics until the baseline level was reached. The rate of decline in FVIII activity was slower for rFVIIIFc than for ADVATE® with mean (+SD) model-predicted elimination half-life values of 11.9±2.98 and 10.4±3.03 hr for ADVATE® and 18.0±3.88 and 18.4±6.99 hr for rFVIIIFc for the 25 and 65 IU/kg dose groups, respectively. Elimination half-life values appeared to be dose-independent over the dose range evaluated for both FVIII products.

Total systemic FVIII exposure (assessed by AUCINF) was ~48% and 61% greater following rFVIIIFc administration than ADVATE® at 25 and 65 IU/kg dose levels, respectively. Mean (+SD) model-predicted AUCINF values were 974±259 and 1810±606 hr*IU/dL for ADVATE® and 1440±316 and 2910±1320 hr*IU/dL for rFVIIIFc for the 25 and 65 IU/kg dose groups, respectively.

Similar to elimination half-life, the MRT was prolonged for rFVIIIFc relative to ADVATE®. Mean (±SD) model-predicted MRT values were 17.1±4.29 and 14.9±4.38 hr for ADVATE® and 25.9±5.60 and 26.5±10.1 hr for rFVIIIFc for the 25 and 65 IU/kg dose groups, respectively. MRT values appeared to be dose-independent over the dose range evaluated for both FVIII products.

In addition, primary PK parameter values for CL and V were determined. CL values for rFVIIIFc only accounted for ~66% of those observed for ADVATE® at equivalent doses. Mean (+SD) model-predicted CL values were 2.70±0.729 and 4.08±1.69 mL/hr/kg for ADVATE® and 1.80±0.409 and 2.69±1.25 mL/hr; g for rFVIIIFc for the 25 and 65 IU/kg dose groups, respectively. V values were comparable between ADVATE® and rFVIIIFc with mean (+SD) model-predicted V values of 43.9±4.27 and 56.1±13.4 mL/kg for ADVATE® and 45.3±7.23 and 61.6±10.6 mL/kg for rFVIIIFc for the 25 and 65 IU/kg dose groups, respectively. Slight increases in mean CL and V values were noted with increasing dose of ADVATE® and rFVIIIFc: however, the increase in standard deviations at the 65 IU/kg dose coupled with limited dose levels confounded an assessment of the dose-dependency of these parameters. For example, the CV % geometric mean CL value for the rFVIIIFc treatment group increased from 23.0% (25 IU/kg) to 48.6% (65 IU/kg).

In addition to the primary PK parameters, secondary PK parameters (e.g. K-values, IVR, etc.) were determined to evaluate FVIII duration of effect. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable. A slight increase in TBLP1 and TBLP3 values were observed with increasing dose of ADVATE® and rFVIIIFc. In contrast, slight decreases in mean IVR and K-values were noted with increasing dose of ADVATE® and rFVIIIFc. As previously indicated, an assessment of the dose dependency of these parameters is confounded by limited dose levels.

Mean (±SD) observed TBLP1 were 2.88±0.733 and 2.93±0.848 IU/dL per IU/kg for ADVATE® and 4.28±0.873 and 5.16±2.02 IU/dL per IU/kg for rFVIIIFc for the 25 and 65 IU/kg dose groups, respectively. Mean (+SD) observed TBLP3 were 2.06±0.527 and 2.26±0.666 IU/dL per IU/kg for ADVATE® and 3.09±0.623 and 3.93±1.59 IU/dL per IU/kg for rFVIIIFc for the 25 and 65 IU/kg dose groups, respectively.

Mean IVR and K-values calculated using observed Cmax values (subtracted with baseline and residual drug within the model) were generally greater than values determined using model-predicted Cmax values; consistent with slight underestimation of the observed peak activity using the one-compartment model. Mean (±SD) observed K-values were 2.57±0.198 and 2.13±0.598 IU/dL per IU/kg for ADVATE® and 2.46±0.330 and 1.85±0.332 IU/dL per IU/kg for rFVIIIFc for the 25 and 65 IU/kg dose groups, respectively. Mean (+SD) observed IVR values were 94.1±15.6 and 85.8±16.5% for ADVATE® and 89.5±11.9 and 74.8±6.72% for rFVIIIFc for the 25 and 65 IU/kg dose groups, respectively.

Single-Dose Pharmacokinetics (Chromogenic Assay)

Observed FVIII activity increased sharply after the short IV infusion of either ADVATE® or rFVIIIFc, with mean (±SD) model-predicted Cmax values of 70.2±9.60 and 157±38.6 IU/dL for ADVATE® and 70.3±10.0 and 158±34.7 IU/dL for rFVIIIFc for the 25 and 65 IU/kg dose groups, respectively.

All ADVATE®- and rFVIIIFc-treated patients had dose-related increases in FVIII activity. The observed increase in both Cmax and AUCINF was slightly less than proportional to dose over the dose range evaluated.

After the end of the infusion, the decline of the observed FVIII activity exhibited monoexponential decay characteristics until the baseline level was reached. The rate of decline in FVIII activity was slower for rFVIIIFc than for ADVATE® with mean (±SD) model-predicted elimination half-life values of 10.7±1.98 and 10.3±3.27 hr for ADVATE® and 16.2±2.92 and 19.0±7.94 hr for rFVIIIFc for the 25 and 65 IU/kg dose groups, respectively. Elimination half-life values appeared to be dose-independent over the dose range evaluated for both FVIII products.

Total systemic FVIII exposure (assessed by AUCINF) was ~53% and 84% greater following rFVIIIFc administration than ADVATE® at 25 and 65 IU/kg dose levels, respectively. Mean (±SD) model-predicted AUCINF values were 1080±236 and 2320±784 hr*IU/dL for ADVATE® and 1650±408 and 4280±1860 hr*IU/dL for rFVIIIFc for the 25 and 65 IU/kg dose groups, respectively.

Similar to elimination half-life, the MRT was prolonged for rFVIIIFc relative to ADVATE®. Mean (±SD) model-predicted MRT values were 15.3±2.86 and 14.8±4.72 hr for ADVATE® and 23.4±4.22 and 27.3±11.4 hr for rFVIIIFc for the 25 and 65 IU/kg dose groups, respectively. MRT values appeared to be dose-independent over the dose range evaluated for both FVIII products.

In addition, primary PK parameter values for CL and V were determined. CL values for rFVIIIFc only accounted for ~58-66% of those observed for ADVATE® at equivalent doses. Mean (±SD) model-predicted CL values were 2.39±0.527 and 3.21 f 1.40 mL/hr/kg for ADVATE® and 1.57±0.349 and 1.86±0.970 mL/hr/kg for rFVIIIFc for the 25 and 65 IU/kg dose groups, respectively. V values were comparable between ADVATE® and rFVIIIFc with mean (±SD) model-predicted V values of 35.8±5.52 and 43.6±11.2 mL/kg for ADVATE® and 35.9±6.65 and 42.7±8.91 mL/kg for rFVIIIFc for the 25 and 65 IU/kg dose groups, respectively. Increases in mean CL and V values were noted with increasing dose of ADVATE® and rFVIIIFc; however, the increase in standard deviations at 65 IU/kg coupled with limited dose levels confounded an assessment of the dose-dependency of these parameters.

In addition to the primary PK parameters, secondary PK parameters (e.g. K-values, IVR, etc.) were determined to evaluate FVIII duration of effect. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable.

A slight increase in TBLP1 and TBLP3 values were observed with increasing dose of ADVATE® and rFVIIIFc.

In contrast, slight decreases in mean IVR and K-values were noted with increasing dose of ADVATE® and rFVIIIFc. As previously indicated, an assessment of the dose dependency of these parameters is confounded by limited dose levels.

Mean (+SD) observed TBLP1 were 2.70±0.511 and 3.09±0.978 IU/dL per IU/kg for ADVATE® and 4.06±0.798 and 5.66±2.38 IU/dL per IU/kg for rFVIIIFc for the 25 and 65 IU/kg dose groups, respectively. Mean (+SD) observed TBLP3 were 1.98±0.377 and 2.39±0.718 IU/dL per IU/kg for ADVATE® and 3.04±0.598 and 4.44±1.84 IU/dL per IU/kg for rFVIIIFc for the 25 and 65 IU/kg dose groups, respectively.

Mean IVR and K-values calculated using observed Cmax values (subtracted with baseline and residual drug within the model) were generally greater than values determined using model-predicted Cmax values: consistent with slight underestimation of the observed peak activity using the one-compartment model. Mean (±SD) observed K-values were 3.08±0.429 and 2.85±0.721 IU/dL per IU/kg for ADVATE® and 3.12±0.451 and 2.92±0.985 IU/dL per IU/kg for rFVIIIFc for the 25 and 65 IU/kg dose groups, respectively. Mean (±SD) observed IVR values were 112±14.5 and 116±26.9% for ADVATE® and 113±16.3 and 117±33.6% for rFVIIIFc for the 25 and 65 IU/kg dose groups, respectively.

Conclusions

All ADVATE®- and rFVIIIFc-treated patients had comparable dose-related increases in Cmax and AUCINF over the dose range evaluated. Peak plasma levels of ADVATE® and rFVIIIFc activity were generally observed within the first hour after the end of the infusion and remained detectable for several days after dosing. After the end of infusion, the decline in baseline corrected FVIII activity exhibited monoexponential decay until the baseline was reached for both products. Parameter values for elimination half-life and MRT appeared to be dose-independent over the dose range evaluated for both FVIII products. Slight increases in mean CL and V values were noted with increasing dose of ADVATE® and rFVIIIFc; however, increased intersubject variability at the 65 IU/kg coupled with limited dose levels confounded an assessment of the dose-dependency of these parameters.

Comparison of rFVIIIFc and ADVATE® activity PK revealed an approximate 48-61% (One-Stage Assay) or 53-84% (Chromogenic Assay) increase in systemic exposure, approximate 30-40% reduction in clearance, and an approximate 50-80% increase in both elimination half-life and MRT for rFVIIIFc relative to ADVATE® at comparable doses. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable.

The PK parameters obtained from Chromogenic Assay results generally agreed with those from the One-Stage Assay, except that the Chomogenic Assay yielded a higher estimation of exposure parameters (e.g. Cmax, AUCINF, etc.).

With the observed improvements in PK, rFVIIIFc may provide a prolonged protection from bleeding, allowing less frequent injections for individuals with Hemophilia A.

Example 8

On the basis of the interim PK analysis from the first-inhuman study of rFVIII:Fc (Example 3), the A-LONG study was designed. A-LONG is an open label, multi-center evaluation of the safety, pharmacokinetics, and efficacy of recombinant Factor VIII Fc fusion (FVIII:Fc) in the prevention and treatment of bleeding in previously treated subjects with severe hemophilia A (defined as <1 IU/dL [<1%] endogenous FVIII).

Approximately 106 subjects will be enrolled into one of three regimens: a tailored prophylaxis regimen (arm 1), a weekly dosing regimen (arm 2), and an on-demand regimen (arm 3).

Arm 1: Tailored Prophylaxis Regimen

Arm 1 will include an overall group and a PK subgroup. Approximately 66 subjects will be enrolled. The initial regimen will be twice weekly at 25 IU/kg on the first day, followed by 50 IU/kg on the fourth day of the week. Subjects will administer rFVIIIFc on this weekly prophylaxis regimen until PK results for rFVIIIFc are available. Base don these results, a tailored prophylaxis regimen will be established for each individual, in which the dose and interval will be determined to maintain a trough level of 1-3% FVIII activity. Each subject will then administer his individually tailored prophylaxis regimen throughout the study.

Subjects will be monitored throughout the study and ongoing dose and interval adjustments will be made. Adjustments will only be made when a subject experiences unacceptable bleeding episodes defined as >2 spontaneous bleeding episodes over a rolling two-month period. In this case, adjustment will target trough levels of 3-5%.

Arm 2: Weekly Dosing Regimen

Approximately 20 subjects will be enrolled/randomized and undergo abbreviated rFVIIIFc PK profiling as follows: Washout of at least 96 hours, a single dose of rFVIIIFc 65 IU/kg; Abbreviated sampling beginning on rFVIIIFc Day 0, including pre-injection and 10 (±2) minutes, 3 hours (±15 minutes), 72 (±2) hours [Day 3], and 96 (±2) hours [Day 4] from the start of injection. Following the abbreviated PK profiling, subjects will then administer a fixed dose of 65 IU/kg rFVIIIFc every 7 days.

Arm 3: On-Demand Regimen

A minimum of 10 major surgeries in at least 5 subjects will be evaluated in the study. Major surgery is defined as any surgical procedure (elective or emergent) that involves general anesthesia and/or respiratory assistance in which a major body cavity is penetrated and exposed, or for which a substantial impairment of physical or physiological functions is produced (e.g., laparotomy, thoracotomy, craniotomy, joint replacement, and limb amputation).

For prophylaxis during surgery, subjects will be treated with 35 to 50 IU/kg rFVIIIFc every 12 to 24 hours. Prior to surgery, the physician will review the subject's rFVIIIFc PK profile and assess the dose regimen of Factor VIII replacement generally required for the type of planned surgery and the clinical status of the subject. Recommendation for the appropriate dosing of rFVIIIFc in the surgical treatment period, including any rehabilitation time, will take these factors into consideration.

The primary objectives of this study are (a) to evaluate the safety and tolerability of rFVIIIFc administered as prophylaxis, on-demand, and surgical treatment regimens; and (b) to evaluate the efficacy of rFVIIIFc administered as prophylaxis, on-demand, and surgical treatment regimens. The secondary objectives of this study are (a) to characterize the PK profile of rFVIIIFc and compare the PK of FVIIIFc with the currently marketed product, ADVATE®; (b) to evaluate individual responses with FVIIIFc; and (c) to evaluate FVIIIFc consumption.

Primary Objectives
  To evaluate safety and tolerability of rFVIIIFc administered as prophylaxis, weekly, on-demand, and surgical treatment regimens
  To evaluate the efficacy of rFVIIIFc administered as tailored prophylaxis, on-demand, and surgical treatment regimens Secondary Objectives
  To characterize the PK profile of rFVIIIFc and compare the PK of rFVIIIFc with the currently marketed product, ADVATE®
  To evaluate individual responses with rFVIIIFc
  To characterize the range of dose and schedules required to adequately prevent bleeding in a prophylaxis regimen: maintain homeostasis in a surgical setting; or to treat bleeding episodes in an on-demand, weekly treatment, or prophylaxis setting
  To evaluate rFVIIIFc consumption (e.g., total annualized rFVIIIFc consumption per subject)

Example 9

Clinical ROTEM Assessment

In the study in Example 8, in addition to the measurement of plasma FVIII activity by one-stage activated partial thromboplastin time (aPTT) assay, whole blood rotational thromboelastometry (ROTEM) has also been explored to assess the improvement in global hemostasis by rFVIIIFc and ADVATE® in 2 subjects, specifically, 1 in the low dose cohort and 1 in the high dose cohort.

rFVIIIFc and ADVATE® appear to be comparably active in clot formation when spiked into subjects' blood prior to rFVIIIFc treatment. The clotting time (CT) was linear with respect to the dose of rFVIIIFc and ADVATE® in the range of approximately 1% of 100% of normal, and the dose response was comparable between rFVIIIFc and ADVATE® in the same subject.

Following dosing with ADVATE® and subsequently rFVIIIFc, citrated whole blood was sampled at various time points and the clot formation following recalcification was monitored by ROTEM. Despite the variable baseline CT due to residue FVIII levels prior to ADVATE® or rFVIIIFc dosing, both products effectively corrected the CT to comparable levels 30 minutes post-injection. In addition, the improvement in CT was better sustained at and after 3 hours post-injection of 25 IU/kg of rFVIIIFc relative to ADVATE® in the subject dosed at this low dose. However, the differential improvement of rFVIIIFc versus ADVATE® was much less appreciable at the 65 IU/kg dose.

TABLES

TABLE 1

Polynucleotide Sequences

A. B-Domain Deleted FVIIIFc
(i) B-Domain Deleted FVIIIFc Chain DNA Sequence (FVIII signal peptide underlined,
Fc region in bold) (SEQ ID NO: 1, which encodes SEQ ID NO: 2)

```
 661                      A TGCAAATAGA GCTCTCCACC TGCTTCTTTC

721    TGTGCCTTTT GCGATTCTGC TTTAGTGCCA CCAGAAGATA CTACCTGGGT GCAGTGGAAC

781    TGTCATGGGA CTATATGCAA AGTGATCTCG GTGAGCTGCC TGTGGACGCA AGATTTCCTC

841    CTAGAGTGCC AAAATCTTTT CCATTCAACA CCTCAGTCGT GTACAAAAAG ACTCTGTTTG

901    TAGAATTCAC GGATCACCTT TTCAACATCG CTAAGCCAAG GCCACCCTGG ATGGGTCTGC

961    TAGGTCCTAC CATCCAGGCT GAGGTTTATG ATACAGTGGT CATTACACTT AAGAACATGG

1021    CTTCCCATCC TGTCAGTCTT CATGCTGTTG GTGTATCCTA CTGGAAAGCT TCTGAGGGAG

1081    CTGAATATGA TGATCAGACC AGTCAAAGGG AGAAAGAAGA TGATAAAGTC TTCCCTGGTG

1141    GAAGCCATAC ATATGTCTGG CAGGTCCTGA AAGAGAATGG TCCAATGGCC TCTGACCCAC

1201    TGTGCCTTAC CTACTCATAT CTTTCTCATG TGGACCTGGT AAAAGACTTG AATTCAGGCC

1261    TCATTGGAGC CCTACTAGTA TGTAGAGAAG GGAGTCTGGC CAAGGAAAAG ACACAGACCT

1321    TGCACAAATT TATACTACTT TTTGCTGTAT TTGATGAAGG GAAAAGTTGG CACTCAGAAA

1381    CAAAGAACTC CTTGATGCAG GATAGGGATG CTGCATCTGC TCGGGCCTGG CCTAAAATGC

1441    ACACAGTCAA TGGTTATGTA AACAGGTCTC TGCCAGGTCT GATTGGATGC CACAGGAAAT

1501    CAGTCTATTG GCATGTGATT GGAATGGGCA CCACTCCTGA AGTGCACTCA ATATTCCTCG

1561    AAGGTCACAC ATTTCTTGTG AGGAACCATC GCCAGGCGTC CTTGGAAATC TCGCCAATAA

1621    CTTTCCTTAC TGCTCAAACA CTCTTGATGG ACCTTGGACA GTTTCTACTG TTTTGTCATA

1681    TCTCTTCCCA CCAACATGAT GGCATGGAAG CTTATGTCAA AGTAGACAGC TGTCCAGAGG

1741    AACCCCAACT ACGAATGAAA AATAATGAAG AAGCGGAAGA CTATGATGAT GATCTTACTG

1801    ATTCTGAAAT GGATGTGGTC AGGTTTGATG ATGACAACTC TCCTTCCTTT ATCCAAATTC

1861    GCTCAGTTGC CAAGAAGCAT CCTAAAACTT GGGTACATTA CATTGCTGCT GAAGAGGAGG
```

TABLE 1-continued

Polynucleotide Sequences

| | |
|---|---|
| 1921 | ACTGGGACTA TGCTCCCTTA GTCCTCGCCC CCGATGACAG AAGTTATAAA AGTCAATATT |
| 1981 | TGAACAATGG CCCTCAGCGG ATTGGTAGGA AGTACAAAAA AGTCCGATTT ATGGCATACA |
| 2041 | CAGATGAAAC CTTTAAGACT CGTGAAGCTA TTCAGCATGA ATCAGGAATC TTGGGACCTT |
| 2101 | TACTTTATGG GGAAGTTGGA GACACACTGT TGATTATATT TAAGAATCAA GCAAGCAGAC |
| 2161 | CATATAACAT CTACCCTCAC GGAATCACTG ATGTCCGTCC TTTGTATTCA AGGAGATTAC |
| 2221 | CAAAAGGTGT AAAACATTTG AAGGATTTTC CAATTCTGCC AGGAGAAATA TTCAAATATA |
| 2281 | AATGGACAGT GACTGTAGAA GATGGGCCAA CTAAATCAGA TCCTCGGTGC CTGACCCGCT |
| 2341 | ATTACTCTAG TTTCGTTAAT ATGGAGAGAG ATCTAGCTTC AGGACTCATT GGCCCTCTCC |
| 2401 | TCATCTGCTA CAAAGAATCT GTAGATCAAA GAGGAAACCA GATAATGTCA GACAAGAGGA |
| 2461 | ATGTCATCCT GTTTTCTGTA TTTGATGAGA ACCGAAGCTG GTACCTCACA GAGAATATAC |
| 2521 | AACGCTTTCT CCCCAATCCA GCTGGAGTGC AGCTTGAGGA TCCAGAGTTC CAAGCCTCCA |
| 2581 | ACATCATGCA CAGCATCAAT GGCTATGTTT TTGATAGTTT GCAGTTGTCA GTTTGTTTGC |
| 2641 | ATGAGGTGGC ATACTGGTAC ATTCTAAGCA TTGGAGCACA GACTGACTTC CTTTCTGTCT |
| 2701 | TCTTCTCTGG ATATACCTTC AAACACAAAA TGGTCTATGA AGACACACTC ACCCTATTCC |
| 2761 | CATTCTCAGG AGAAACTGTC TTCATGTCGA TGGAAAACCC AGGTCTATGG ATTCTGGGGT |
| 2821 | GCCACAACTC AGACTTTCGG AACAGAGGCA TGACCGCCTT ACTGAAGGTT TCTAGTTGTG |
| 2881 | ACAAGAACAC TGGTGATTAT TACGAGGACA GTTATGAAGA TATTTCAGCA TACTTGCTGA |
| 2941 | GTAAAAACAA TGCCATTGAA CCAAGAAGCT TCTCTCAAAA CCCACCAGTC TTGAAACGCC |
| 3001 | ATCAACGGGA AATAACTCGT ACTACTCTTC AGTCAGATCA AGAGGAAATT GACTATGATG |
| 3061 | ATACCATATC AGTTGAAATG AAGAAGGAAG ATTTTGACAT TTATGATGAG GATGAAAATC |
| 3121 | AGAGCCCCCG CAGCTTTCAA AAGAAAACAC GACACTATTT TATTGCTGCA GTGGAGAGGC |
| 3181 | TCTGGGATTA TGGGATGAGT AGCTCCCCAC ATGTTCTAAG AAACAGGGCT CAGAGTGGCA |
| 3241 | GTGTCCCTCA GTTCAAGAAA GTTGTTTTCC AGGAATTTAC TGATGGCTCC TTTACTCAGC |
| 3301 | CCTTATACCG TGGAGAACTA AATGAACATT TGGGACTCCT GGGGCCATAT ATAAGAGCAG |
| 3361 | AAGTTGAAGA TAATATCATG GTAACTTTCA GAAATCAGGC CTCTCGTCCC TATTCCTTCT |
| 3421 | ATTCTAGCCT TATTTCTTAT GAGGAAGATC AGAGGCAAGG AGCAGAACCT AGAAAAAACT |
| 3481 | TTGTCAAGCC TAATGAAACC AAAACTTACT TTTGGAAAGT GCAACATCAT ATGGCACCCA |
| 3541 | CTAAAGATGA GTTTGACTGC AAAGCCTGGG CTTATTTCTC TGATGTTGAC CTGGAAAAAG |
| 3601 | ATGTGCACTC AGGCCTGATT GGACCCCTTC TGGTCTGCCA CACTAACACA CTGAACCCTG |
| 3661 | CTCATGGGAG ACAAGTGACA GTACAGGAAT TTGCTCTGTT TTTCACCATC TTTGATGAGA |
| 3721 | CCAAAAGCTG GTACTTCACT GAAAATATGG AAAGAAACTG CAGGGCTCCC TGCAATATCC |
| 3781 | AGATGGAAGA TCCCACTTTT AAAGAGAATT ATCGCTTCCA TGCAATCAAT GGCTACATAA |
| 3841 | TGGATACACT ACCTGGCTTA GTAATGGCTC AGGATCAAAG GATTCGATGG TATCTGCTCA |
| 3901 | GCATGGGCAG CAATGAAAAC ATCCATTCTA TTCATTTCAG TGGACATGTG TTCACTGTAC |
| 3961 | GAAAAAAAGA GGAGTATAAA ATGGCACTGT ACAATCTCTA TCCAGGTGTT TTTGAGACAG |
| 4021 | TGGAAATGTT ACCATCCAAA GCTGGAATTT GGCGGGTGGA ATGCCTTATT GGCGAGCATC |
| 4081 | TACATGCTGG GATGAGCACA CTTTTTCTGG TGTACAGCAA TAAGTGTCAG ACTCCCCTGG |
| 4141 | GAATGGCTTC TGGACACATT AGAGATTTTC AGATTACAGC TTCAGGACAA TATGGACAGT |
| 4201 | GGGCCCCAAA GCTGGCCAGA CTTCATTATT CCGGATCAAT CAATGCCTGG AGCACCAAGG |

TABLE 1-continued

Polynucleotide Sequences

| | |
|---|---|
| 4261 | AGCCCTTTTC TTGGATCAAG GTGGATCTGT TGGCACCAAT GATTATTCAG GGCATGAAGA |
| 4321 | CCCAGGGTGC CCGTGAGAAG TTCTCCAGCC TCTACATCTC TCAGTTTATC ATCATGTATA |
| 4381 | GTCTTGATGG GAAGAAGTGG CAGACTTATC GAGGAAATTC CACTGGAACC TTAATGGTCT |
| 4441 | TCTTTGGCAA TGTGGATTCA TCTGGGATAA ACACAATAT TTTTAACCCT CCAATTATTG |
| 4501 | CTCGATACAT CCGTTTGCAC CCAACTCATT ATAGCATTCG CAGCACTCTT CGCATGGAGT |
| 4561 | TGATGGGCTG TGATTTAAAT AGTTGCAGCA TGCCATTGGG AATGGAGAGT AAAGCAATAT |
| 4621 | CAGATGCACA GATTACTGCT TCATCCTACT TTACCAATAT GTTTGCCACC TGGTCTCCTT |
| 4681 | CAAAAGCTCG ACTTCACCTC CAAGGGAGGA GTAATGCCTG GAGACCTCAG GTGAATAATC |
| 4741 | CAAAAGAGTG GCTGCAAGTG GACTTCCAGA AGACAATGAA AGTCACAGGA GTAACTACTC |
| 4801 | AGGGAGTAAA ATCTCTGCTT ACCAGCATGT ATGTGAAGGA GTTCCTCATC TCCAGCAGTC |
| 4861 | AAGATGGCCA TCAGTGGACT CTCTTTTTTC AGAATGGCAA AGTAAAGGTT TTTCAGGGAA |
| 4921 | ATCAAGACTC CTTCACACCT GTGGTGAACT CTCTAGACCC ACCGTTACTG ACTCGCTACC |
| 4981 | TTCGAATTCA CCCCCAGAGT TGGGTGCACC AGATTGCCCT GAGGATGGAG GTTCTGGGCT |
| 5041 | GCGAGGCACA GGACGTCTAC GACAAAACTC ACACATGCCC ACCGTGCCCA GCTCCAGAAC |
| 5101 | TCCTGGGCGG ACCGTCAGTC TTCCTCTTCC CCCCAAAACC CAAGGACACC CTCATGATCT |
| 5161 | CCCGGACCCC TGAGGTCACA TGCGTGGTGG TGGACGTGAG CCACGAAGAC CCTGAGGTCA |
| 5221 | AGTTCAACTG GTACGTGGAC GGCGTGGAGG TGCATAATGC CAAGACAAAG CCGCGGGAGG |
| 5281 | AGCAGTACAA CAGCACGTAC CGTGTGGTCA GCGTCCTCAC CGTCCTGCAC CAGGACTGGC |
| 5341 | TGAATGGCAA GGAGTACAAG TGCAAGGTCT CCAACAAAGC CCTCCCAGCC CCCATCGAGA |
| 5401 | AAACCATCTC CAAAGCCAAA GGGCAGCCCC GAGAACCACA GGTGTACACC CTGCCCCCAT |
| 5461 | CCCGGGATGA GCTGACCAAG AACCAGGTCA GCCTGACCTG CCTGGTCAAA GGCTTCTATC |
| 5521 | CCAGCGACAT CGCCGTGGAG TGGGAGAGCA ATGGGCAGCC GGAGAACAAC TACAAGACCA |
| 5581 | CGCCTCCCGT GTTGGACTCC GACGGCTCCT TCTTCCTCTA CAGCAAGCTC ACCGTGGACA |
| 5641 | AGAGCAGGTG GCAGCAGGGG AACGTCTTCT CATGCTCCGT GATGCATGAG GCTCTGCACA |
| 5701 | ACCACTACAC GCAGAAGAGC CTCTCCCTGT CTCCGGGTAA A |

(ii) Fc DNA sequence (mouse igk signal peptide underlined) SEQ ID NO: 3, which encodes SEQ ID NO: 4)

| | |
|---|---|
| 7981 | <u>ATGGA GACAGACACA</u> |
| 8041 | <u>CTCCTGCTAT GGGTACTGCT GCTCTGGGTT CCAGGTTCCA CTGGTGACAA</u> AACTCACACA |
| 8101 | TGCCCACCGT GCCCAGCACC TGAACTCCTG GAGGACCGT CAGTCTTCCT CTTCCCCCCA |
| 8161 | AAACCCAAGG ACACCCTCAT GATCTCCCGG ACCCCTGAGG TCACATGCGT GGTGGTGGAC |
| 9221 | GTGAGCCACG AAGACCCTGA GGTCAAGTTC AACTGGTACG TGGACGGCGT GGAGGTGCAT |
| 8281 | AATGCCAAGA CAAAGCCGCG GGAGGAGCAG TACAACAGCA CGTACCGTGT GGTCAGCGTC |
| 8341 | CTCACCGTCC TGCACCAGGA CTGGCTGAAT GGCAAGGAGT ACAAGTGCAA GGTCTCCAAC |
| 6401 | AAAGCCCTCC CAGCCCCCAT CGAGAAAACC ATCTCCAAAG CCAAAGGGCA GCCCCGAGAA |
| 8461 | CCACAGGTGT ACACCCTGCC CCCATCCCGC GATGAGCTGA CCAAGAACCA GGTCAGCCTG |
| 8521 | ACCTGCCTGG TCAAAGGCTT CTATCCCAGC GACATCGCCG TGGAGTGGGA GAGCAATGGG |
| 8581 | CAGCCGGAGA ACAACTACAA GACCACGCCT CCCGTGTTGG ACTCCGACGG CTCCTTCTTC |
| 8641 | CTCTACAGCA AGCTCACCGT GGACAAGAGC AGGTGGCAGC AGGGGAACGT CTTCTCATGC |

TABLE 1-continued

Polynucleotide Sequences

8701    TCCGTGATGC ATGAGGCTCT GCACAACCAC TACACGCAGA AGAGCCTCTC CCTGTCTCCG

8761    GGTAAA

B. Full Length FVIIIFc
(i) Full Length FVIIIFc DNA Sequence (FVIII signal peptide underlined, Fc region in bold) (SEQ ID NO: 5, which encodes SEQ ID NO: 6)

661                                         <u>ATG CAAATAGAGC TCTCCACCTG</u>

721     <u>CTTCTTTCTG TGCCTTTTGC GATTCTGCTT TAGT</u>GCCACC AGAAGATACT ACCTGGGTGC

781     AGTGGAACTG TCATGGGACT ATATGCAAAG TGATCTCGGT GAGCTGCCTG TGGACGCAAG

841     ATTTCCTCCT AGAGTGCCAA ATCTTTTCC ATTCAACACC TCAGTCGTGT ACAAAAAGAC

901     TCTGTTTGTA GAATTCACGG ATCACCTTTT CAACATCGCT AAGCCAAGGC CACCCTGGAT

961     GGGTCTGCTA GGTCCTACCA TCCAGGCTGA GGTTTATGAT ACAGTGGTCA TTACACTTAA

1021    GAACATGGCT TCCCATCCTG TCAGTCTTCA TGCTGTTGGT GTATCCTACT GGAAAGCTTC

1081    TGAGGGAGCT GAATATGATG ATCAGACCAG TCAAAGGGAG AAGGAAGATG ATAAAGTCTT

1141    CCCTGGTGGA AGCCATACAT ATGTCTGGCA GGTCCTGAAA GAGAATGGTC CAATGGCCTC

1201    TGACCCACTG TGCCTTACCT ACTCATATCT TTCTCATGTG GACCTGGTAA AAGACTTGAA

1261    TTCAGGCCTC ATTGGAGCCC TACTAGTATG TAGAGAAGGG AGTCTGGCCA AGGAAAAGAC

1321    ACAGACCTTG CACAAATTTA TACTACTTTT TGCTGTATTT GATGAAGGGA AAAGTTGGCA

1381    CTCAGAAACA AAGAACTCCT TGATGCAGGA TAGGGATGCT GCATCTGCTC GGGCCTGGCC

1441    TAAAATGCAC ACAGTCAATG GTTATGTAAA CAGGTCTCTG CCAGGTCTGA TTGGATGCCA

1501    CAGGAAATCA GTCTATTGGC ATGTGATTGG AATGGGCACC ACTCCTGAAG TGCACTCAAT

1561    ATTCCTCGAA GGTCACACAT TTCTTGTGAG GAACCATCGC CAGGCGTCCT TGGAAATCTC

1621    GCCAATAACT TTCCTTACTG CTCAAACACT CTTGATGGAC CTTGGACAGT TTCTACTGTT

1681    TTGTCATATC TCTTCCCACC AACATGATGG CATGGAAGCT TATGTCAAAG TAGACAGCTG

1741    TCCAGAGGAA CCCCAACTAC GAATGAAAAA TAATGAAGAA GCGGAAGACT ATGATGATGA

1801    TCTTACTGAT TCTGAAATGG ATGTGGTCAG GTTTGATGAT GACAACTCTC CTTCCTTTAT

1861    CCAAATTCGC TCAGTTGCCA AGAAGCATCC TAAAACTTGG GTACATTACA TTGCTGCTGA

1921    AGAGGAGGAC TGGGACTATG CTCCCTTAGT CCTCGCCCCC GATGACAGAA GTTATAAAAG

1981    TCAATATTTG AACAATGGCC CTCAGCGGAT TGGTAGGAAG TACAAAAAAG TCCGATTTAT

2041    GGCATACACA GATGAAACCT TTAAGACTCG TGAAGCTATT CAGCATGAAT CAGGAATCTT

2101    GGGACCTTTA CTTTATGGGG AAGTTGGAGA CACACTGTTG ATTATATTTA AGAATCAAGC

2161    AAGCAGACCA TATAACATCT ACCCTCACGG AATCACTGAT GTCCGTCCTT TGTATTCAAG

2221    GAGATTACCA AAAGGTGTAA AACATTTGAA GGATTTTCCA ATTCTGCCAG GAGAAATATT

2281    CAAATATAAA TGGACAGTGA CTGTAGAAGA TGGGCCAACT AAATCAGATC CTCGGTGCCT

2341    GACCCGCTAT TACTCTAGTT TCGTTAATAT GGAGAGAGAT CTAGCTTCAG GACTCATTGG

2401    CCCTCTCCTC ATCTGCTACA AGAATCTGT AGATCAAAGA GGAAACCAGA TAATGTCAGA

2461    CAAGAGGAAT GTCATCCTGT TTTCTGTATT TGATGAGAAC CGAAGCTGGT ACCTCACAGA

2521    GAATATACAA CGCTTTCTCC CCAATCCAGC TGGAGTGCAG CTTGAGGATC CAGAGTTCCA

2531    AGCCTCCAAC ATCATGCACA GCATCAATGG CTATGTTTTT GATAGTTTGC AGTTGTCAGT

2641    TTGTTTGCAT GAGGTGGCAT ACTGGTACAT TCTAAGCATT GGAGCACAGA CTGACTTCCT

2701    TTCTGTCTTC TTCTCTGGAT ATACCTTCAA ACACAAAATG GTCTATGAAG ACACACTCAC

TABLE 1-continued

Polynucleotide Sequences

| | |
|---|---|
| 2761 | CCTATTCCCA TTCTCAGGAG AAACTGTCTT CATGTCGATG GAAAACCCAG GTCTATGGAT |
| 2821 | TCTGGGGTGC CACAACTCAG ACTTTCGGAA CAGAGGCATG ACCGCCTTAC TGAAGGTTTC |
| 2881 | TAGTTGTGAC AAGAACACTG GTGATTATTA CGAGGACAGT TATGAAGATA TTTCAGCATA |
| 2841 | CTTGCTGAGT AAAAACAATG CCATTGAACC AAGAAGCTTC TCCCAGAATT CAAGACACCC |
| 3001 | TAGCACTAGG CAAAAGCAAT TTAATGCCAC CACAATTCCA GAAAATGACA TAGAGAAGAC |
| 3061 | TGACCCTTGG TTTGCACACA GAACACCTAT GCCTAAAATA CAAAATGTCT CCTCTAGTGA |
| 3121 | TTTGTTGATG CTCTTGCGAC AGAGTCCTAC TCCACATGGG CTATCCTTAT CTGATCTCCA |
| 3181 | AGAAGCCAAA TATGAGACTT TTTCTGATGA TCCATCACCT GGAGCAATAG ACAGTAATAA |
| 3241 | CAGCCTGTCT GAAATGACAC ACTTCAGGCC ACAGCTCCAT CACAGTGGGG ACATGGTATT |
| 3301 | TACCCCTGAG TCAGGCCTCC AATTAAGATT AAATGAGAAA CTGGGGACAA CTGCAGCAAC |
| 3361 | AGAGTTGAAG AAACTTGATT TCAAAGTTTC TAGTCATCA AATAATCTGA TTTCAACAAT |
| 3421 | TCCATCAGAC AATTTGGCAG CAGGTACTGA TAATACAAGT TCCTTAGGAC CCCCAAGTAT |
| 3481 | GCCAGTTCAT TATGATAGTC AATTAGATAC CACTCTATTT GGCAAAAAGT CATCTCCCCT |
| 3541 | TACTGAGTCT GGTGGACCTC TGAGCTTGAG TGAAGAAAAT AATGATTCAA AGTTGTTAGA |
| 3601 | ATCAGGTTTA ATGAATAGCC AAGAAAGTTC ATGGGGAAAA AATGTATCGT CAACAGAGAG |
| 3661 | TGGTAGGTTA TTTAAAGGGA AAAGAGCTCA TGGACCTGCT TGTTGACTA AAGATAATGC |
| 3721 | CTTATTCAAA GTTAGCATCT CTTTGTTAAA GACAAACAAA ACTTCCAATA ATTCAGCAAC |
| 3781 | TAATAGAAAG ACTCACATTG ATGGCCCATC ATTATTAATT GAGAATAGTC CATCAGTCTG |
| 3841 | GCAAAATATA TTAGAAAGTG ACACTGAGTT TAAAAAAGTG ACACCTTTGA TTCATGACAG |
| 3901 | AATGCTTATG GACAAAAATG CTACAGCTTT GAGGCTAAAT CATATGTCAA ATAAAACTAC |
| 3961 | TTCATCAAAA AACATGGAAA TGGTCCAACA GAAAAAGAG GGCCCCATTC CACCAGATGC |
| 4021 | ACAAAATCCA GATATGTCGT TCTTTAAGAT GCTATTCTTG CCAGAATCAG CAAGGTGGAT |
| 4081 | ACAAAGGACT CATGGAAAGA ACTCTCTGAA CTCTGGGCAA GGCCCCAGTC CAAAGCAATT |
| 4141 | AGTATCCTTA GGACCAGAAA AATCTGTGGA AGGTCAGAAT TTCTTGTCTG AGAAAAACAA |
| 4201 | AGTGGTAGTA GGAAAGGGTG AATTTACAAA GGACGTAGGA CTCAAAGAGA TGGTTTTTCC |
| 4261 | AAGCAGCAGA AACCTATTTC TTACTAACTT GGATAATTTA CATGAAAATA ATACACACAA |
| 4321 | TCAAGAAAAA AAATTCAGG AAGAAATAGA AAAGAAGGAA ACATTAATCC AAGAGAATGT |
| 4381 | AGTTTTGCCT CAGATACATA CAGTGACTGG CACTAAGAAT TTCATGAAGA ACCTTTTCTT |
| 4441 | ACTGAGCACT AGGCAAAATG TAGAAGGTTC ATATGACGGG CATATGCTC CAGTACTTCA |
| 4501 | AGATTTTAGG TCATTAAATG ATTCAACAAA TAGAACAAAG AAACACACAG CTCATTTCTC |
| 4561 | AAAAAAGGG GAGGAAGAAA ACTTGGAAGG CTTGGGAAAT CAAACCAAGC AAATTGTAGA |
| 4621 | GAAATATGCA TGCACCACAA GGATATCTCC TAATACAAGC CAGCAGAATT TTGTCACGCA |
| 4681 | ACGTAGTAAG AGAGCTTTGA ACAATTCAG ACTCCCACTA GAAGAAACAG AACTTGAAAA |
| 4741 | AAGGATAATT GTGGATGACA CCTCAACCCA GTGGTCCAAA AACATGAAAC ATTTGACCCC |
| 4801 | GAGCACCCTC ACACAGATAG ACTACAATGA GAAGGAGAAA GGGGCCATTA CTCAGTCTCC |
| 4861 | CTTATCAGAT TGCCTTACGA GGAGTCATAG CATCCCTCAA GCAAATAGAT CTCCATTACC |
| 4921 | CATTGCAAAG GTATCATCAT TTCCATCTAT TAGACCTATA TATCTGACCA GGGTCCTATT |
| 4981 | CCAAGACAAC TCTTCTCATC TTCCAGCAGC ATCTTATAGA AAGAAAGATT CTGGGGTCCA |
| 5041 | AGAAAGCAGT CATTTCTTAC AAGGAGCCAA AAAAAATAAC CTTTCTTTAG CCATTCTAAC |

TABLE 1-continued

Polynucleotide Sequences

```
5101  CTTGGAGATG ACTGGTGATC AAAGAGAGGT TGGCTCCCTG GGACAAGTG CCACAAATTC
5161  AGTCACATAC AAGAAAGTTG AGAACACTGT TCTCCCGAAA CCAGACTTGC CCAAAACATC
5221  TGGCAAAGTT GAATTGCTTC CAAAAGTTCA CATTTATCAG AAGGACCTAT TCCCTACGGA
5281  AACTAGCAAT GGGTCTCCTG GCCATCTGGA TCTCGTGGAA GGGAGCCTTC TTCAGGGAAC
5341  AGAGGGAGCG ATTAAGTGGA ATGAAGCAAA CAGACCTGGA AAAGTTCCCT TTCTGAGAGT
5401  AGCAACAGAA AGCTCTGCAA AGACTCCCTC CAAGCTATTG GATCCTCTTG CTTGGGATAA
5461  CCACTATGGT ACTCAGATAC AAAAGAAGA GTGGAAATCC AAGAGAAGT CACCAGAAAA
5521  AACAGCTTTT AAGAAAAAGG ATACCATTTT GTCCCTGAAC GCTTGTGAAA GCAATCATGC
5581  AATAGCAGCA ATAAATGAGG ACAAAATAA GCCCGAAATA GAAGTCACCT GGGCAAAGCA
5641  AGGTAGGACT GAAAGGCTGT GCTCTCAAAA CCCACCAGTC TTGAAACGCC ATCAACGGGA
5701  AATAACTCGT ACTACTCTTC AGTCAGATCA AGAGGAAATT GACTATGATG ATACCATATC
5761  AGTTGAAATG AAGAAGGAAG ATTTTGACAT TTATGATGAG GATGAAAATC AGAGCCCCCG
5821  CAGCTTTCAA AAGAAAACAC GACACTATTT TATTGCTGCA GTGGAGAGGC TCTGGGATTA
5881  TGGGATGAGT AGCTCCCCAC ATGTTCTAAG AAACAGGGCT CAGAGTGGCA GTGTCCCTCA
5941  GTTCAAGAAA GTTGTTTTCC AGGAATTTAC TGATGGCTCC TTTACTCAGC CCTTATACCG
6001  TGGAGAACTA AATGAACATT TGGGACTCCT GGGGCCATAT ATAAGAGCAG AAGTTGAAGA
6061  TAATATCATG GTAACTTTCA GAAATCAGGC CTCTCGTCCC TATTCCTTCT ATTCTAGCCT
6121  TATTTCTTAT GAGGAAGATC AGAGGCAAGG AGCAGAACCT AGAAAAAACT TTGTCAAGCC
6181  TAATGAAACC AAAACTTACT TTTGGAAAGT GCAACATCAT ATGGCACCCA CTAAAGATGA
6241  GTTTGACTGC AAAGCCTGGG CTTATTTCTC TGATGTTGAC CTGGAAAAAG ATGTGCACTC
6301  AGGCCTGATT GGACCCCTTC TGGTCTGCCA CACTAACACA CTGAACCCTG CTCATGGGAG
6361  ACAAGTGACA GTACAGGAAT TTGCTCTGTT TTTCACCATC TTTGATGAGA CCAAAAGCTG
6421  GTACTTCACT GAAAATATGG AAAGAAACTG CAGGGCTCCC TGCAATATCC AGATGGAAGA
6481  TCCCACTTTT AAAGAGAATT ATCGCTTCCA TGCAATCAAT GGCTACATAA TGGATACACT
6541  ACCTGGCTTA GTAATGGCTC AGGATCAAAG GATTCGATGG TATCTGCTCA GCATGGGCAG
6601  CAATGAAAAC ATCCATTCTA TTCATTTCAG TGGACATGTG TTCACTGTAC GAAAAAAGA
6661  GGAGTATAAA ATGGCACTGT ACAATCTCTA TCCAGGTGTT TTTGAGACAG TGGAAATGTT
6721  ACCATCCAAA GCTGGAATTT GGCGGGTGGA ATGCCTTATT GGCGAGCATC TACATGCTGG
6781  GATGAGCACA CTTTTTCTGG TGTACAGCAA TAAGTGTCAG ACTCCCCTGG GAATGGCTTC
6841  TGGACACATT AGAGATTTTC AGATTACAGC TTCAGGACAA TATGGACAGT GGGCCCCAAA
6901  GCTGGCCAGA CTTCATTATT CCGGATCAAT CAATGCCTGG AGCACCAAGG AGCCCTTTTC
6961  TTGGATCAAG GTGGATCTGT TGGCACCAAT GATTATTCAC GGCATCAAGA CCCAGGGTGC
7021  CCGTCAGAAG TTCTCCAGCC TCTACATCTC TCAGTTTATC ATCATGTATA GTCTTGATGG
7081  GAAGAAGTGG CAGACTTATC GAGGAAATTC CACTGGAACC TTAATGGTCT TCTTTGGCAA
7141  TGTGGATTCA TCTGGGATAA AACACAATAT TTTTAACCCT CCAATTATTG CTCGATACAT
7201  CCGTTTGCAC CCAACTCATT ATAGCATTCG CAGCACTCTT CGCATGGAGT TGATGGGCTG
7261  TGATTTAAAT AGTTGCAGCA TGCCATTGGG AATGGAGAGT AAAGCAATAT CAGATGCACA
7321  GATTACTGCT TCATCCTACT TTACCAATAT GTTTGCCACC TGGTCTCCTT CAAAAGCTCG
7381  ACTTCACCTC CAAGGGAGGA GTAATGCCTG GAGACCTCAG GTGAATAATC CAAAAGAGTG
```

TABLE 1-continued

Polynucleotide Sequences

```
7441    GCTGCAAGTG GACTTCCAGA AGACAATGAA AGTCACAGGA GTAACTACTC AGGGAGTAAA
7501    ATCTCTGCTT ACCAGCATGT ATGTGAAGGA GTTCCTCATC TCCAGCAGTC AAGATGGCCA
7561    TCAGTGGACT CTCTTTTTTC AGAATGGCAA AGTAAAGGTT TTTCAGGGAA ATCAAGACTC
7621    CTTCACACCT GTGGTGAACT CTCTAGACCC ACCGTTACTG ACTCGCTACC TTCGAATTCA
7681    CCCCCAGAGT TGGGTGCACC AGATTGCCCT GAGGATGGAG GTTCTGGGCT GCGAGGCACA
7741    GGACCTCTAC GACAAAACTC ACACATGCCC ACCGTGCCCA GCTCCAGAAC TCCTGGGCGG
7801    ACCGTCAGTC TTCCTCTTCC CCCCAAAACC CAAGGACACC CTCATGATCT CCCGGACCCC
7861    TGAGGTCACA TGCGTGGTGG TGGACGTGAG CCACGAAGAC CCTGAGGTCA AGTTCAACTG
7921    GTACGTGGAC GGCGTGGAGG TGCATAATGC CAAGACAAAG CCGCGGGAGG AGCAGTACAA
7981    CAGCACGTAC CGTGTGGTCA GCGTCCTCAC CGTCCTGCAC CAGGACTGGC TGAATGGCAA
8041    GGAGTACAAG TGCAAGGTCT CCAACAAAGC CCTCCCAGCC CCCATCGAGA AAACCATCTC
8101    CAAAGCCAAA GGGCAGCCCC GAGAACCACA GGTGTACACC CTGCCCCCAT CCCGGGATGA
8161    GCTGACCAAG AACCAGGTCA GCCTGACCTG CCTGGTCAAA GGCTTCTATC CAGCGACAT
8221    CGCCGTGGAG TGGGAGAGCA ATGGGCAGCC GGAGAACAAC TACAAGACCA CGCCTCCCGT
8281    GTTGGACTCC GACGGCTCCT TCTTCCTCTA CAGCAAGCTC ACCGTGGACA AGAGCAGGTG
8341    GCAGCAGGGG AACGTCTTCT CATGCTCCGT GATGCATGAG GCTCTGCACA ACCACTACAC
8401    GCAGAAGAGC CTCTCCCTGT CTCCGGGTAA A
```

(ii) Fc (same sequence as A (ii) (SEQ ID NO: 3))]
C.
(i) Heavy Chain (HC)-Fc DNA sequence (no linker between HC and Fc) (signal peptide underlined, Fc region in bold) (SEQ ID NO: 7, which encodes SEQ ID NO: 8)

```
   1    ATGCAAATAG AGCTCTCCAC CTGCTTCTTT CTGTGCCTTT TGCGATTCTG CTTTAGTGCC
  61    ACCAGAAGAT ACTACCTGGG TGCAGTGGAA CTGTCATGGG ACTATATGCA AAGTGATCTC
 121    GGTGAGCTGC CTGTGGACGC AAGATTTCCT CCTAGAGTGC AAAATCTTT TCCATTCAAC
 181    ACCTCAGTCG TGTACAAAAA GACTCTGTTT GTAGAATTCA CGGATCACCT TTTCAACATC
 241    GCTAAGCCAA GGCCACCCTG GATGGGTCTG CTAGGTCCTA CCATCCAGGC TGAGGTTTAT
 301    GATACAGTGG TCATTACACT TAAGAACATG GCTTCCCATC CTGTCAGTCT TCATGCTGTT
 361    GGTGTATCCT ACTGGAAAGC TTCTGAGGGA GCTGAATATG ATGATCAGAC CAGTCAAAGG
 421    GAGAAAGAAG ATGATAAAGT CTTCCCTGGT GGAAGCCATA CATATGTCTG GCAGGTCCTG
 481    AAAGAGAATG GTCCAATGGC CTCTGACCCA CTGTGCCTTA CCTACTCATA TCTTTCTCAT
 541    GTGGACCTGG TAAAAGACTT GAATTCAGGC CTCATTGGAG CCCTACTAGT ATGTAGAGAA
 601    GGGAGTCTGG CCAAGGAAAA GACACAGACC TTGCACAAAT TTATACTACT TTTTGCTGTA
 661    TTTGATGAAG GGAAAAGTTG GCACTCAGAA ACAAAGAACT CCTTGATGCA GGATAGGGAT
 721    GCTGCATCTG CTCGGGCCTG GCCTAAAATG CACACAGTCA ATGGTTATGT AAACAGGTCT
 781    CTGCCAGGTC TGATTGGATG CCACAGGAAA TCAGTCTATT GGCATGTGAT TGGAATGGGC
 841    ACCACTCCTG AAGTGCACTC AATATTCCTC GAAGGTCACA CATTTCTTGT GAGGAACCAT
 901    CGCCAGGCGT CCTTGGAAAT CTCGCCAATA ACTTTCCTTA CTGCTCAAAC ACTCTTGATG
 961    GACCTTGGAC AGTTTCTACT GTTTTGTCAT ATCTCTTCCC ACCAACATGA TGGCATGGAA
1021    GCTTATGTCA AAGTAGACAG CTGTCCAGAG GAACCCCAAC TACGAATGAA AAATAATGAA
1081    GAAGCGGAAG ACTATGATGA TGATCTTACT GATTCTGAAA TGGATGTGGT CAGGTTTGAT
1141    GATGACAACT CTCCTTCCTT TATCCAAATT CGCTCAGTTG CCAAGAAGCA TCCTAAAACT
```

TABLE 1-continued

Polynucleotide Sequences

```
1201    TGGGTACATT ACATTGCTGC TGAAGAGGAG GACTGGGACT ATGCTCCCTT AGTCCTCGCC

1261    CCCGATGACA GAAGTTATAA AAGTCAATAT TTGAACAATG GCCCTCAGCG GATTGGTAGG

1321    AAGTACAAAA AAGTCCGATT TATGGCATAC ACAGATGAAA CCTTTAAGAC TCGTGAAGCT

1381    ATTCAGCATG AATCAGGAAT CTTGGGACCT TTACTTTATG GGGAAGTTGG AGACACACTG

1441    TTGATTATAT TTAAGAATCA AGCAAGCAGA CCATATAACA TCTACCCTCA CGGAATCACT

1501    GATGTCCGTC CTTTGTATTC AAGGAGATTA CCAAAAGGTG TAAACATTT GAAGGATTTT

1561    CCAATTCTGC CAGGAGAAAT ATTCAAATAT AAATGGACAG TGACTGTAGA AGATGGGCCA

1621    ACTAAATCAG ATCCTCGGTG CCTGACCCGC TATTACTCTA GTTTCGTTAA TATGGAGAGA

1681    GATCTAGCTT CAGGACTCAT TGGCCCTCTC CTCATCTGCT ACAAAGAATC TGTAGATCAA

1741    AGAGGAAACC AGATAATGTC AGACAAGAGG AATGTCATCC TGTTTTCTGT ATTTGATGAG

1801    AACCGAAGCT GGTACCTCAC AGAGAATATA CAACGCTTTC TCCCCAATCC AGCTGGAGTG

1861    CAGCTTGAGG ATCCAGAGTT CCAAGCCTCC AACATCATGC ACAGCATCAA TGGCTATGTT

1921    TTTGATAGTT TGCAGTTGTC AGTTTGTTTG CATGAGGTGG CATACTGGTA CATTCTAAGC

1981    ATTGGAGCAC AGACTGACTT CCTTTCTGTC TTCTTCTCTG GATATACCTT CAAACACAAA

2041    ATGGTCTATG AAGACACACT CACCCTATTC CCATTCTCAG GAGAAACTGT CTTCATGTCG

2101    ATGGAAAACC CAGGTCTATG GATTCTGGGG TGCCACAACT CAGACTTTCG GAACAGAGGC

2161    ATGACCGCCT TACTGAAGGT TTCTAGTTGT GACAAGAACA CTGGTGATTA TTACGAGGAC

2221    AGTTATGAAG ATATTTCAGC ATACTTGCTG AGTAAAAACA ATGCCATTGA ACCAAGAGAC

2281    AAAACTCACA CATGCCCACC GTGCCCAGCT CCAGAACTCC TGGGCGGACC GTCAGTCTTC

2341    CTCTTCCCCC CAAAACCCAA GGACACCCTC ATGATCTCCC GGACCCCTGA GGTCACATGC

2401    GTGGTGGTGG ACGTGAGCCA CGAAGACCCT GAGGTCAAGT TCAACTGGTA CGTGGACGGC

2461    GTGGAGGTGC ATAATGCCAA GACAAAGCCG CGGGAGGAGC AGTACAACAG CACGTACCGT

2521    GTGGTCAGCG TCCTCACCGT CCTGCACCAG GACTGGCTGA ATGGCAAGGA GTACAAGTGC

2581    AAGGTCTCCA ACAAAGCCCT CCCAGCCCCC ATCGAGAAAA CCATCTCCAA AGCCAAAGGG

2641    CAGCCCCGAG AACCACAGGT GTACACCCTG CCCCCATCCC GGGATGAGCT GACCAAGAAC

2701    CAGGTCAGCC TGACCTGCCT GGTCAAAGGC TTCTATCCCA GCGACATCGC CGTGGAGTGG

2761    GAGAGCAATG GGCAGCCGGA GAACAACTAC AAGACCACGC CTCCCGTGTT GGACTCCGAC

2821    GGCTCCTTCT TCCTCTACAG CAAGCTCACC GTGGACAAGA GCAGGTGGCA GCAGGGGAAC

2881    GTCTTCTCAT GCTCCGTGAT GCATGAGGCT CTGCACAACC ACTACACGCA GAAGAGCCTC

2941    TCCCTGTCTC CGGGTAAA
```

C.
(ii) Heavy Chain (HC)-Fc DNA sequence (5 amino acid linker between HC and Fc)
(signal peptide underlined, Fc region in bold 5 amino acid linker is double-
underlined)(SEQ ID NO: 9, which encodes SEQ ID NO: 10)

```
  1    ATGCAAATAG AGCTCTCCAC CTGCTTCTTT CTGTGCCTTT TGCGATTCTG CTTTAGTGCC

61    ACCAGAAGAT ACTACCTGGG TGCAGTGGAA CTGTCATGGG ACTATATGCA AAGTGATCTC

121    GGTGAGCTGC CTGTGGACGC AAGATTTCCT CCTAGAGTGC CAAAATCTTT TCCATTCAAC

181    ACCTCAGTCG TGTACAAAAA GACTCTGTTT GTAGAATTCA CGGATCACCT TTTCAACATC

241    GCTAAGCCAA GGCCACCCTG GATGGGTCTG CTAGGTCCTA CCATCCAGGC TGAGGTTTAT

301    GATACAGTGG TCATTACACT TAAGAACATG GCTTCCCATC CTGTCAGTCT TCATGCTGTT

361    GGTGTATCCT ACTGGAAAGC TTCTGAGGGA GCTGAATATG ATGATCAGAC CAGTCAAAGG
```

TABLE 1-continued

Polynucleotide Sequences

```
 421   GAGAAAGAAG ATGATAAAGT CTTCCCTGGT GGAAGCCATA CATATGTCTG GCAGGTCCTG
 481   AAAGAGAATG GTCCAATGGC CTCTGACCCA CTGTGCCTTA CCTACTCATA TCTTTCTCAT
 541   GTGGACCTGG TAAAAGACTT GAATTCAGGC CTCATTGGAG CCCTACTAGT ATGTAGAGAA
 601   GGGAGTCTGG CCAAGGAAAA GACACAGACC TTGCACAAAT TATACTACT  TTTTGCTGTA
 661   TTTGATGAAG GGAAAAGTTG GCACTCAGAA ACAAAGAACT CCTTGATGCA GGATAGGGAT
 721   GCTGCATCTG CTCGGGCCTG GCCTAAAATG CACACAGTCA ATGGTTATGT AAACAGGTCT
 781   CTGCCAGGTC TGATTGGATG CCACAGGAAA TCAGTCTATT GGCATGTGAT TGGAATGGGC
 841   ACCACTCCTG AAGTGCACTC AATATTCCTC GAAGGTCACA CATTTCTTGT GAGGAACCAT
 901   CGCCAGGCGT CCTTGGAAAT CTCGCCAATA ACTTTCCTTA CTGCTCAAAC ACTCTTGATG
 961   GACCTTGGAC AGTTTCTACT GTTTTGTCAT ATCTCTTCCC ACCAACATGA TGGCATGGAA
1021   GCTTATGTCA AAGTAGACAG CTGTCCAGAG GAACCCCAAC TACGAATGAA AAATAATGAA
1081   GAAGCGGAAG ACTATGATGA TGATCTTACT GATTCTGAAA TGGATGTGGT CAGGTTTGAT
1141   GATGACAACT CTCCTTCCTT TATCCAAATT CGCTCAGTTG CCAAGAAGCA TCCTAAAACT
1201   TGGGTACATT ACATTGCTGC TGAAGAGGAG GACTGGGACT ATGCTCCCTT AGTCCTCGCC
1261   CCCGATGACA GAAGTTATAA AAGTCAATAT TTGAACAATG CCCTCAGCG  GATTGGTAGG
1321   AAGTACAAAA AAGTCCGATT TATGGCATAC ACAGATGAAA CCTTTAAGAC TCGTGAAGCT
1381   ATTCAGCATG AATCAGGAAT CTTGGGACCT TTACTTTATG GGAAGTTGG  AGACACACTG
1441   TTGATTATAT TTAAGAATCA AGCAAGCAGA CCATATAACA TCTACCCTCA CGGAATCACT
1501   GATGTCCGTC CTTTGTATTC AAGGAGATTA CCAAAAGGTG TAAAACATTT GAAGGATTTT
1561   CCAATTCTGC CAGGAGAAAT ATTCAAATAT AAATGGACAG TGACTGTAGA AGATGGGCCA
1621   ACTAAATCAG ATCCTCGGTG CCTGACCCGC TATTACTCTA GTTTCGTTAA TATGGAGAGA
1681   GATCTAGCTT CAGGACTCAT TGGCCCTCTC CTCATCTGCT ACAAAGAATC TGTAGATCAA
1741   AGAGGAAACC AGATAATGTC AGACAAGAGG AATGTCATCC TGTTTTCTGT ATTTGATGAG
1801   AACCGAAGCT GGTACCTCAC AGAGAATATA CAACGCTTTC TCCCCAATCC AGCTGGAGTG
1861   CAGCTTGAGG ATCCAGAGTT CCAAGCCTCC AACATCATGC ACAGCATCAA TGGCTATGTT
1921   TTTGATAGTT TGCAGTTGTC AGTTTGTTTG CATGAGGTGG CATACTGGTA CATTCTAAGC
1981   ATTGGAGCAC AGACTGACTT CCTTTCTGTC TTCTTCTCTG GATATACCTT CAAACACAAA
2041   ATGGTCTATG AAGACACACT CACCCTATTC CCATTCTCAG GAGAAACTGT CTTCATGTCG
2101   ATGGAAAACC CAGGTCTATG GATTCTGGGG TGCCACAACT CAGACTTTCG GAACAGAGGC
2161   ATGACCGCCT TACTGAAGGT TTCTAGTTGT GACAAGAACA CTGGTGATTA TTACGAGGAC
2221   AGTTATGAAG ATATTTCAGC ATACTTGCTG AGTAAAAACA ATGCCATTGA ACCAAGA<u>AGC</u>
2281   <u>TTCTCCCAGA AT</u>GACAAAAC TCACACATGC CCACCGTGCC CAGCTCCAGA ACTCCTGGGC
2341   GGACCGTCAG TCTTCCTCTT CCCCCCAAAA CCCAAGGACA CCCTCATGAT CTCCCGGACC
2401   CCTGAGGTCA CATGCGTGGT GGTGGACGTG AGCCACGAAG ACCCTGAGGT CAAGTTCAAC
2461   TGGTACGTGG ACGGCGTGGA GGTGCATAAT GCCAAGACAA AGCCGCGGGA GGAGCAGTAC
2521   AACAGCACGT ACCGTGTGGT CAGCGTCCTC ACCGTCCTGC ACCAGGACTG GCTGAATGGC
2581   AAGGAGTACA AGTGCAAGGT CTCCAACAAA GCCCTCCCAG CCCCCATCGA GAAAACCATC
2641   TCCAAAGCCA AAGGGCAGCC CCGAGAACCA CAGGTGTACA CCCTGCCCCC ATCCCGGGAT
2701   GAGCTGACCA AGAACCAGGT CAGCCTGACC TGCCTGGTCA AAGGCTTCTA TCCCAGCGAC
```

| | |
|---|---|
| 2761 | ATCGCCGTGG AGTGGGAGAG CAATGGGCAG CCGGAGAACA ACTACAAGAC CACGCCTCCC |
| 2821 | GTGTTGGACT CCGACGGCTC CTTCTTCCTC TACAGCAAGC TCACCGTGGA CAAGAGCAGG |
| 2881 | TGGCAGCAGG GGAACGTCTT CTCATGCTCC GTGATGCATG AGGCTCTGCA CAACCACTAC |
| 2941 | ACGCAGAAGA GCCTCTCCCT GTCTCCGGGT AAA |

C.
(iii) Light Chain (LC)-Fc DNA sequence (signal peptide underlined. Fc region in bold)(SEQ ID NO: 11, which encodes SEQ ID NO: 12)

| | |
|---|---|
| 1 | <u>ATGGAGACAG ACACACTCCT GCTATGGGTA CTGCTGCTCT GGGTTCCAGG TTCCACTGGT</u> |
| 61 | GAAATAACTC GTACTACTCT TCAGTCAGAT CAAGAGGAAA TTGACTATGA TGATACCATA |
| 121 | TCAGTTGAAA TGAAGAAGGA AGATTTTGAC ATTTATGATG AGGATGAAAA TCAGAGCCCC |
| 181 | CGCAGCTTTC AAAAGAAAAC ACGACACTAT TTTATTGCTG CAGTGGAGAG GCTCTGGGAT |
| 241 | TATGGGATGA GTAGCTCCCC ACATGTTCTA AGAAACAGGG CTCAGAGTGG CAGTGTCCCT |
| 301 | CAGTTCAAGA AAGTTGTTTT CCAGGAATTT ACTGATGGCT CCTTTACTCA GCCCTTATAC |
| 361 | CGTGGAGAAC TAAATGAACA TTTGGGACTC CTGGGGCCAT ATATAAGAGC AGAAGTTGAA |
| 421 | GATAATATCA TGGTAACTTT CAGAAATCAG GCCTCTCGTC CTATTCCTT CTATTCTAGC |
| 481 | CTTATTTCTT ATGAGGAAGA TCAGAGGCAA GGAGCAGAAC CTAGAAAAAA CTTTGTCAAG |
| 541 | CCTAATGAAA CCAAAACTTA CTTTTGGAAA GTGCAACATC ATATGGCACC CACTAAAGAT |
| 601 | GAGTTTGACT GCAAAGCCTG GGCTTATTTC TCTGATGTTG ACCTGGAAAA AGATGTGCAC |
| 661 | TCAGGCCTGA TTGGACCCCT TCTGGTCTGC CACACTAACA CACTGAACCC TGCTCATGGG |
| 721 | AGACAAGTGA CAGTACAGGA ATTTGCTCTG TTTTTCACCA TCTTTGATGA GACCAAAAGC |
| 781 | TGGTACTTCA CTGAAAAATAT GGAAAGAAAC TGCAGGGCTC CCTGCAATAT CCAGATGGAA |
| 841 | GATCCCACTT TTAAAGAGAA TTATCGCTTC CATGCAATCA ATGGCTACAT AATGGATACA |
| 901 | CTACCTGGCT TAGTAATGGC TCAGGATCAA AGGATTCGAT GGTATCTGCT CAGCATGGGC |
| 961 | AGCAATGAAA ACATCCATTC TATTCATTTC AGTGGACATG TGTTCACTGT ACGAAAAAAA |
| 1021 | GAGGAGTATA AAATGGCACT GTACAATCTC TATCCAGGTG TTTTTGAGAC AGTGGAAATG |
| 1081 | TTACCATCCA AAGCTGGAAT TTGGCGGGTG GAATGCCTTA TTGGCGAGCA TCTACATGCT |
| 1141 | GGGATGAGCA CACTTTTTCT GGTGTACAGC AATAAGTGTC AGACTCCCCT GGGAATGGCT |
| 1201 | TCTGGACACA TTAGAGATTT TCAGATTACA GCTTCAGGAC AATATGGACA GTGGGCCCCA |
| 1261 | AAGCTGGCCA GACTTCATTA TTCCGGATCA ATCAATGCCT GGAGCACCAA GGAGCCCTTT |
| 1321 | TCTTGGATCA AGGTGGATCT GTTGGCACCA ATGATTATTC ACGGCATCAA GACCCAGGGT |
| 1381 | GCCCGTCAGA AGTTCTCCAG CCTCTACATC TCTCAGTTTA TCATCATGTA TAGTCTTGAT |
| 1441 | GGGAAGAAGT GGCAGACTTA TCGAGGAAAT TCCACTGGAA CCTTAATGGT CTTCTTTGGC |
| 1501 | AATGTGGATT CATCTGGGAT AAAACACAAT ATTTTTAACC CTCCAATTAT TGCTCGATAC |
| 1561 | ATCCGTTTGC ACCCAACTCA TTATAGCATT CGCAGCACTC TTCGCATGGA GTTGATGGGC |
| 1621 | TGTGATTTAA ATAGTTGCAG CATGCCATTG GGAATGGAGA GTAAAGCAAT ATCAGATGCA |
| 1681 | CAGATTACTG CTTCATCCTA CTTTACCAAT ATGTTTGCCA CCTGGTCTCC TTCAAAAGCT |
| 1741 | CGACTTCACC TCCAAGGGAG GAGTAATGCC TGGAGACCTC AGGTGAATAA TCCAAAAGAG |
| 1801 | TGGCTGCAAG TGGACTTCCA GAAGACAATG AAAGTCACAG GAGTAACTAC TCAGGGAGTA |
| 1861 | AAATCTCTGC TTACCAGCAT GTATGTGAAG GAGTTCCTCA TCTCCAGCAG TCAAGATGGC |
| 1921 | CATCAGTGGA CTCTCTTTTT TCAGAATGGC AAAGTAAAGG TTTTTCAGGG AAATCAAGAC |
| 1981 | TCCTTCACAC CTGTGGTGAA CTCTCTAGAC CCACCGTTAC TGACTCGCTA CCTTCGAATT |

TABLE 1-continued

Polynucleotide Sequences

```
2041    CACCCCCAGA GTTGGGTGCA CCAGATTGCC CTGAGGATGG AGGTTCTGGG CTGCGAGGCA

2101    CAGGACCTCT ACGACAAAAC TCACACATGC CCACCGTGCC CAGCTCCAGA ACTCCTGGGC

2161    GGACCGTCAG TCTTCCTCTT CCCCCCAAAA CCCAAGGACA CCCTCATGAT CTCCCGGACC

2221    CCTGAGGTCA CATGCGTGGT GGTGGACGTG AGCCACGAAG ACCCTGAGGT CAAGTTCAAC

2281    TGGTACGTGG ACGGCGTGGA GGTGCATAAT GCCAAGACAA AGCCGCGGGA GGAGCAGTAC

2341    AACAGCACGT ACCGTGTGGT CAGCGTCCTC ACCGTCCTGC ACCAGGACTG GCTGAATGGC

2401    AAGGAGTACA AGTGCAAGGT CTCCAACAAA GCCCTCCCAG CCCCCATCGA GAAAACCATC

2461    TCCAAAGCCA AAGGGCAGCC CCGAGAACCA CAGGTGTACA CCCTGCCCCC ATCCCGGGAT

2521    GAGCTGACCA AGAACCAGGT CAGCCTGACC TGCCTGGTCA AAGGCTTCTA TCCCAGCGAC

2581    ATCGCCGTGG AGTGGGAGAG CAATGGGCAG CCGGAGAACA ACTACAAGAC CACGCCTCCC

2641    GTGTTGGACT CCGACGGCTC CTTCTTCCTC TACAGCAAGC TCACCGTGGA CAAGAGCAGG

2701    TGGCAGCAGG GGAACGTCTT CTCATGCTCC GTGATGCATG AGGCTCTGCA CAACCACTAC

2761    ACGCAGAAGA GCCTCTCCCT GTCTCCGGGT AAA
```

TABLE 2

Polypeptide Sequences

A. B-Domain Deleted FVIII-Fc Monomer Hybrid (BDD FVIIIFc monomer dimer):
created by coexpressing BDD FVIIIFc and Fc chains.

Construct = HC-LC-Fc fusion. An Fc expression cassette is cotransfected with
BDDFVIII-Fc to generate the BDD FVIIIFc monomer-. For the BDD FVIIIFc chain,
the Fc sequence is shown in bold; HC sequence is shown in double underline;
remaining B domain sequence is shown in italics. Signal peptides are underlined.

i) B domain deleted FVIII-Fc chain (19 amino acid signal sequence underlined) (SEQ ID
NO: 2)
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNKEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESSGILGPLLYG
EVGDTLLIIFKNQASRPYNIYPHGITDVRPLYSRRLPKGVKHLKDFPILPGEIFKYKWTVTVEDG
PTKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYSDISAYLLSKNNAIEPR*SFSQNPPVLKRHQR*EITRTTLQSDQEEIDYDDTISVEMKK
EDFDIYDEDENQSPRSFQKKTRHYFIAAVERLWDYGMSSSPHVLRNRAQSGSVPQFKKVVFQEFT
DGSFTQPLYRGELNEHLGLLGPYIRAEVEDNIMVTFRNQASRPYSFYSSLISYEEDQRGAEPRK
NFVKPNETKTYFWKVQHHMAPTKDEFDCKAWAYFSDVDLEKDVHSGLIGPLLVCHTNTLNPAHGR
QVTVQEFALFFTIFDETKSWYFTENMERNCRAPCNIQMEDPTFKENYRFHAINGYIMDTLPGLVM
AQDQRIRWYLLSMGSNENIHSIHFSGHVFTVRKKEEYKMALYNLYPGVFETVEMLPSKAGIWRVE
CLIGEHLHAGMSTLFLVYSNKCQTPLGMASGHIRDFQITASGQYGQWAPKLARLHYSGSINAWST
KEPFSWIKVDLLAPMIIHGIKTQGARQKFSSLYISQFIIMYSLDGKKWQTYRGNSTGTLMVFFGN
VDSSGIKHNIFNPPIIARYIRLKPTHYSIRSTLRMELMGCDLNSCSMPLGMESKAISDAQITASS
YFTNMFATWSPSKARLHLQGRSNAWRPQVNNPKEWLQVDFQKTMKVTGVTTQGVKSLLTSMYVKE
FLISSSQDGHQWTLFFQNGKVKVFQGNQDSFTPVVNSLDPPLLTRYLRIHPQSWVHQIALRMEVL
GCEAQDLYD**KTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK**

TABLE 2-continued

Polypeptide Sequences ii) Fc chain (20 amino acid heterologous signal peptide from mouse IgK
chain underlined)(SEQ ID NO: 4)
METDTLLLWVLLLWVPGSTG
DKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK B. Full length FVIIIFc monomer hybrid (Full length FVIIIFc monomer dimer):
created by coexpressing FVIIIFc and Fc chains.

Construct = HC-B-LC-Fc fusion. An Fc expression cassette is cotransfected with full
length FVIII-Fc to generate the full length FVIIIFc monomer. For the FVIIIFc chain,
the Fc sequence is shown in bold; HC sequence is shown in double underline; B domain
sequence is shown in italics. Signal peptides are underlined.

i) Full length FVIIIFc chain (FVIII signal peptide underlined (SEQ ID NO: 6)
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILGPLLYG
EVGDTLLIIFKNQASRPYNIYPHGITDVRPLYSRRLPKGVKHLKDFPILPGEIFKYKWTVTVEDG
PTKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPRSFSQNSRHPSTRQKQFNATTIPENDIEKTDPWFAHRTPMP
KIQNVSSSDLLMLLRQSPTPHGLSLSDLQEAKYETFSDDPSPGAIDSNNSLSEMTHFRPQLHHSG
DMVFTPESGLQLRLNEKLGTTAATELKKLDFKVSSTSNNLISTIPSDNLAAGTDNTSSLGPPSMP
VHYDSQLDTTLFGKKSSPLTESGGPLSLSEENNDSKLLESGLMNSQESSWGKNVSSTESGRLFKG
KRAHGPALLTKDNALFKVSISLLKTNKTSNNSATNRKTHIDGPSLLIENSPSVWQNILESDTEFK
KVTPLIHDRMLMDKNATALRLNHMSNKTTSSKNMEMVQQKKEGPIPPDAQNPDMSFFKMLFLPES
ARWIQRTHGKNSLNSGQGPSPKQLVSLGPEKSVEGQNFLSEKNKVVVGKGEFTKDVGLKEMVFPS
SRNLFLTNLDNLHENNTHNQEKKIQEEIEKKETLIQENVVLPQIHTVTGTKNFMKNLFLLSTRQN
VEGSYQGAYAPVLQDFRSLNDSTNRTKKHTAHFSKKGEEENLEGLGNQTKQIVEKYACTTRISPN
TSQQNFVTQRSKRALKQFRLPLEETELEKRIIVDDTSTQWSKNMKHLTPSTLTQIDYNEKEKGAI
TQSPLSDCLTRSHSIPQANRSPLPIAKVSSFPSIRPIYLTRVLFQDNSSHLPAASYRKKDSGVQE
SSHFLQGAKKNNLSLAILTLEMTGDQREVGSLGTSATNSVTYKKVENTVLPKPDLPFTSGKVELL
PKVHIYQKDLFPTETSNGSPGHLDLVEGSLLQGTEGAIKWNEANRPGKVPFLRVATESSAKTPSK
LLDPLAWDNHYGTQIPKEEWKSQEKSPEKTAFKKKDTILSLNACESNHAIAAINEGQNKPEIEVT
WAKQGRTERLCSQNPPVLKRHQREITRTTLQSDQEEIDYDDTISVEMKKEDFDIYDEDENQSPRS
FQKKTRHYFIAAVERLWDYGMSSSPHVLRNRAQSGSVPQFKKVVFQEFTDGSFTQPLYRGELNEH
LGLLGPYIRAEVEDNIMVTFRNQASRPYSFYSSLISYEEDQRGAEPRKNFVKPNETKTYFWKVQ
HHMAPTKDEFDCKAWAYFSDVDLEKDVHSGLIGPLLVCHTNTLNPAHGRQVTVQEFALFFTIFDE
TKSWYFTENMERNCRAPCNIQMEDPTFKENYRFHAINGYIMDTLPGLVMAQDQRIRWYLLSMGSN
ENIHSIHFSGHVFTVRKKEEYKMALYNLYPGVFETVEMLPSKAGIWRVECLIGEHLHAGMSTLFL
VYSNKCQTPLGMASGHIRDFQITASGQYGQWAPKLARLHYSGSINAWSTKEPFSWIKVDLLAPMI
IHGIKTQGARQKFSSLYISQFIIMYSLDGKKWQTYRGNSTGTLMVFFGNVDSSGIKHNIFNPPII
ARYIRLHPTHYSIRSTLRMELMGCDLNSCSMPLGMESKAISDAQITASSYFTNMFATWSPSKARL
HLQGRSNAWRPQVNNPKEWLQVDFQKTMKVTGVTTQGVKSLLTSMYVKEFLISSSQDGHQWTLFF
QNGKVKVFQGNQDSFTPVVNSLDPPLLTRYLRIHPQSWVHQIALRMEVLGCEAQDLY**DKTHTCPP
CPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVF
SCSVMHEALHNHYTQKSLSLSPGK** ii) Fc chain (20 amino acid heterologous signal peptide from mouse IgK
chain underlined)(SEQ ID NO: 4)
METDTLLLWVLLLWVPGSTG
DKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK C. FVIII-Fc Heterodimer Hybrid
This is made by cotransfecting HC-Fc and LC-Fc constructs. Two HC-Fc constructs have
been made. One has no linker between HC and Fc (HC-Fc) while the other has a 5 amino
acid linker between HC and Fc (HC+5-Fc). The FVIII signal peptide was used for the
HC-Fc constructs, while the mouse IgK signal sequence was used for the LC-Fc construct.

(i) HC-Fc (Fc sequence is shown in bold, signal peptide underlined) (SEQ ID NO: 8)
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP TABLE 2-continued Polypeptide Sequences

```
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILPGLLYG
EVGDTLLIIFKNQASRPYNIYPHGITDVRPLYSRRLPKGVKHLKDFPILPGEIFKYKWTVTVEDG
PTKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPRDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSN
KALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK
```

(ii) HC+5-Fc (Fc sequence is shown in bold. 5 amino acid linker sequence (from the B domain of FVIII) is shown in italics, signal peptide underlined.)(SEQ ID NO: 10)

```
MQIELSTCFFLCLLRFCFS
ATRRYYLGAVELSWDYMQSDLGELPVDARFPPRVPKSFPFNTSVVYKKTLFVEFTDHLFNIAKPR
PPWMGLLGPTIQAEVYDTVVITLKNMASHPVSLHAVGVSYWKASEGAEYDDQTSQREKEDDKVFP
GGSHTYVWQVLKENGPMASDPLCLTYSYLSHVDLVKDLNSGLIGALLVCREGSLAKEKTQTLHKF
ILLFAVFDEGKSWHSETKNSLMQDRDAASARAWPKMHTVNGYVNRSLPGLIGCHRKSVYWHVIGM
GTTPEVHSIFLEGHTFLVRNHRQASLEISPITFLTAQTLLMDLGQFLLFCHISSHQHDGMEAYVK
VDSCPEEPQLRMKNNEEAEDYDDDLTDSEMDVVRFDDDNSPSFIQIRSVAKKHPKTWVHYIAAEE
EDWDYAPLVLAPDDRSYKSQYLNNGPQRIGRKYKKVRFMAYTDETFKTREAIQHESGILPGLLYG
EVGDTLLIIFKNQASRPYNIYPHGITDVRPLYSRRLPKGVKHLKDFPILPGEIFKYKWTVTVEDG
PTKSDPRCLTRYYSSFVNMERDLASGLIGPLLICYKESVDQRGNQIMSDKRNVILFSVFDENRSW
YLTENIQRFLPNPAGVQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNRGMTALLKVSSCDKNT
GDYYEDSYEDISAYLLSKNNAIEPRSFSQNDKTHTCPPCPAPELLGGPSVFLFPPKPKDTLMISR
TPEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHNHYTQKSLSLSPGK
```

(iii) LC-Fc6His (Fc sequence is shown in bold, signal peptide underlined.)(SEQ ID NO: 12)

```
METDTLLLWVLLLWVPGSTG
EITRTTLQSDQEEIDYDDTISVEMKKEDFDIYDEDENQSPRSFQKKTRHYFIAAVERLWDYGMSS
SPHVLRNRAQSGSVPQFKKVVFQEFTDGSFTQPLYRGELNEHLGLLGPYIRAEVEDNIMVTFRNQ
ASRPYSFYSSLISYEEDQRQGAEPRKNFVKPNETKTYFWKVQHHMAPTKDEFDCKAWAYFSDVDL
EKDVHSGLIGPLLVCHTNTLNPAHGRQVTVQEFALFFTIFDETKSWYFTENMERNCRAPCNIQME
DPTFKENYRFHAINGYIMDTLPGLVMAQDQRIRWYLLSMGSNENIHSIHFSGHVFTVRKKEEYKM
ALYNLYPGVFETVEMLPSKAGIWRVECLIGEHLHAGMSTLFLVYSNKCQTPLGMASGHIRDFQIT
ASGQYGQWAPKLARLHYSGSINAWSTKEPFSWIKVDLLAPMIIHGIKTQGARQKFSSLYISQFII
MYSLDGKKWQTYRGNSTGTLMVFFGNVDSSGIKHNIFNPPIIARYIRLHPTHYSIRSTLRMELMG
CDLNSCSMPLGMESKAISDAQITASSYFTNMFATWSPSKARLHLQGRSNAWRPQVNNPKEWLQVD
FQKTMKVTGVTTQGVKSLLTSMYVKEFLISSSQDGHQWTLFFQNGKVKVFQGNQDSFTPVVNSLD
PFLLTRYLRIHPQSWVHQIALRMEVLGCEAQDLYDKTHTCPPCPAPELLGGPSVFLFPPKPKDTL
MISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPG
K
```

TABLE 3

Whole blood clotting time (WBCT) determination in hemophilia A mice after a single intravenous dose of 50 IU/kg rFVIIIFc or REFACTO ®.

A.

| Treatment | Animal Number | Pre-dose | 0.25 | 24 | 36 | 42 | 96 | 113 | 120 |
|---|---|---|---|---|---|---|---|---|---|
|  |  |  |  | WBCT, min |  |  |  |  |  |
| 50 IU/kg REFACTO ® | 1 | >60 | 18 | >60 | ND | ND |  |  |  |
|  | 2 | >60 | 5 | 16 | >60 | ND |  |  |  |
|  | 3 | >60 | 4 | 7 | >60 | ND |  |  |  |
|  | 4 | >60 | 7 | 8 | 10 | >60 |  |  |  |
|  | 5 | >60 | 6 | 9 | 16 | >60 |  |  |  |
|  | 6 | >60 | 5 | 15 | >60 | ND |  |  |  |
| 50 IU/kg rFVIIIFc | 7 | >60 | 7 |  |  |  | 8 | >60 | ND |
|  | 8 | >60 | 5 |  |  |  | 8 | >60 | ND |
|  | 9 | >60 | 4 |  |  |  | 16 | >60 | ND |

TABLE 3-continued

Whole blood clotting time (WBCT) determination in hemophilia A mice after a single intravenous dose of 50 IU/kg rFVIIIFc or REFACTO ®.

|  |  |  |  |  |  |
|---|---|---|---|---|---|
| 10 | >60 | 3 | 11 | 4 | >60 |
| 11 | >60 | 3 | 9 | >60 | ND |
| 12 | >60 | 4 | 6 | >60 | ND |

B.

| | | Time of Blood Collection, hr | | | | |
|---|---|---|---|---|---|---|
| Treatment | Animal Number | Pre-dose | 0.25 | 24 | 48 | 96 | 120 |
| | | WBCT, min | | | | | |
| 50 IU/kg REFACTO ® | 1 | >60 | 11 | 15 | >60 | >60 | ND |
| | 2 | >60 | 3 | 3 | >60 | >60 | >60 |
| | 3 | >60 | 4 | 6 | >60 | >60 | >60 |
| 50 IU,kg rFVIIIFc | 4 | >60 | 3 | 5 | 5 | >60 | >60 |
| | 5 | >60 | 3 | 6 | 7 | 13 | >60 |
| | 6 | >60 | 5 | 8 | 9 | 9 | >60 |

ND = Not determined since previous time point was >60 min

TABLE 4

PK Parameters after a single intravenous dose in hemophilia A mice (50 IU/kg)

| Treatment | $C_{max}$ (IU/mL) | AUC (hr · IU/mL) | $T_{1/2}$ (hr) | CL (mL/hr/kg) | Vss (mL/kg) |
|---|---|---|---|---|---|
| rFVIIIFc | 1.56 | 22.6 | 11.1 | 2.09 | 28.4 |
| REFACTO ® | 0.67 | 6.94 | 5.0 | 7.2 | 43.8 |
| ADVATE ® | 0.47 | 3.90 | 7.1 | 12.8 | 103 |

TABLE 5

PK Parameters after a single intravenous dose in hemophilia A dogs (125 IU/kg rFVIIIFc, 114 and 120 IU/kg REFACTO ®)

A. PK determined from chromogenic activity data

| Treatment | $C_{max}$ (IU/mL) | AUC (hr · IU/mL) | $T_{1/2}$ (hr) | CL (mL/hr/kg) | Vz (mL/kg) |
|---|---|---|---|---|---|
| rFVIIIFc | 2.0 ± 0.54 | 25.9 ± 6.47 | 15.4 ± 0.3 | 5.1 ± 1.4 | 113 ± 29 |
| REFACTO ®* | 2.0 | 18.2 | 7.4 | 6.5 | 68.7 |

B. PK determined from ELISA data

| Treatment | $C_{max}$ (ng/mL) | AUC (hr · ng/mL) | $T_{1/2}$ (hr) | CL (mL/hr/kg) | Vz (mL/kg) |
|---|---|---|---|---|---|
| rFVIIIFc | 210 ± 33 | 2481 ± 970 | 15.7 ± 1.7 | 6.2 ± 3.0 | 144 ± 83 |
| REFACTO ®* | 211 | 1545 | 6.9 | 8.7 | 85 |

Mean ± sd, n = 4 for rFVIIIFc, n = 2 for REFACTO ®
*sd not reported for REFACTO ® since there were just two dogs

TABLE 6

Clotting activity measured by aPTT in hemophilia A dogs after a single intravenous dose with rFVIIIFc or REFACTO ®.

| Dog ID | Treatment | aPTT, sec PreDose | 5 min post dose |
|---|---|---|---|
| M10 | rFVIIIFc | 86.5 | 53.6 |
| M11 | rFVIIIFc | 99.8 | 56.4 |
| M12 | rFVIIIFc | 119 | 68.7 |
|  | REFACTO ® | 108 | 60.7 |
| M38 | rFVIIIFc | 115 | 76.6 |
|  | REFACTO ® | 118 | 68.0 |

TABLE 7

Plasma Concentration of rFVIIIFc or XYNTHA ® in monkeys administered as a single intravenous dose of 125 IU/kg measured by ELISA.

| Time, hr | Group 1 | | | Group 2 | | | Mean | SD |
|---|---|---|---|---|---|---|---|---|
|  | 604376 | 606595 | C36195 | C36066 | C36174 | 604362 |  |  |
| A. rFVIIIFc concentration in plasma (μg/mL) | | | | | | | | |
| Pre | BLQ | BLQ | BLQ | BLQ | BLQ | BLQ |  |  |
| 0.25 | 0.400 | 0.334 | 0.374 | 0.348 | 0.383 | 0.323 | 0.360 | 0.030 |
| 4 | 0.266 | 0.259 | 0.236 | 0.233 | 0.259 | 0.217 | 0.245 | 0.019 |
| 12 | 0.165 | 0.152 | 0.12 | 0.15 | 0.161 | 0.149 | 0.150 | 0.016 |
| 24 | 0.079 | 0.074 | 0.047 | 0.08 | 0.088 | 0.076 | 0.074 | 0.014 |
| 36 | 0.035 | 0.04 | 0.022 | 0.04 | 0.041 | 0.046 | 0.037 | 0.008 |
| 48 | 0.019 | 0.021 | BLQ | 0.021 | 0.024 | 0.025 | 0.022 | 0.002 |
| B. XYNTHA ® concentration in plasma (μg/mL) | | | | | | | | |
| Pre | BLQ | BLQ | BLQ | BLQ | BLQ | BLQ |  |  |
| 0.25 | 0.252 | 0.074 | 0.155 | 0.317 | 0.217 | 0.167 | 0.197 | 0.084 |
| 4 | 0.197 | 0.159 | 0.152 | 0.229 | 0.19 | 0.082 | 0.168 | 0.051 |
| 12 | 0.137 | 0.099 | 0.104 | 0.166 | 0.158 | 0.081 | 0.124 | 0.035 |
| 24 | 0.09 | 0.068 | 0.051 | 0.082 | 0.08 | 0.084 | 0.076 | 0.014 |
| 36 | 0.037 | 0.043 | 0.015 | 0.041 | 0.035 | BLQ | 0.034 | 0.011 |
| 48 | 0.022 | BLQ | BLQ | 0.017 | 0.013 | BLQ | 0.017 | 0.005 |

TABLE 8

Plasma Concentration of rFVIIIFc or XYNTHA ® in monkeys administered a single intravenous dose of 125 IU/kg measured by the FVIII-specific chromogenic activity assay (reported in IU/mL).

| Time (hr) | Group 1 | | | Group 2 | | |
|---|---|---|---|---|---|---|
| Predose | 604376 | 606595 | C36195 | C36066 | C36174 | 604362 |
| A. XYNTHA ® | | | | | | |
| 0.25 | 5.62 | 4.55 | 5.01 | 4.5 | 5.15 | 3.77 |
| 4 | 3.9 | 4.05 | 3.2 | 3.19 | 3.46 | 2.36 |
| 12 | 2.51 | 2.82 | 1.69 | 2.17 | 2.5 | 2.01 |
| 24 | 1.67 | 1.66 | 1.18 | 0.95 | 1.57 | 1.5 |
| 36 | 0.7 | 0.85 | 0.48 | 0.44 | 0.85 | 0.82 |
| 48 | BLQ | BLQ | BLQ | BLQ | 0.38 | 0.48 |
| B. rFVIIIFc | | | | | | |
| 0.25 | 4.31 | 3.82 | 3.54 | 4.13 | 4.12 | 3.68 |
| 4 | 3 | 3.36 | 2.53 | 2.7 | 2.74 | 2.81 |
| 12 | 2 | 2.15 | 1.42 | 2.28 | 2.75 | 2.22 |
| 24 | 1.01 | 1.17 | 0.5 | 1.5 | 1.61 | 1.01 |
| 36 | BLQ | 0.52 | 0.48 | 0.88 | 0.72 | 0.64 |
| 48 | 0.31 | BLQ | BLQ | BLQ | BLQ | BLQ |
| 72 | BLQ | BLQ | BLQ | BLQ | 0.31 | BLQ |

BLQ = below the limit of quantitation

TABLE 9

PK Parameters of rFVIIIFc after a single 125 IU/kg dose

| PK Parameter | units | Group 1 | | | Group 2 | | | Average | SD |
|---|---|---|---|---|---|---|---|---|---|
| | | 604376 | 606595 | C36195 | C36066 | C36174 | 604362 | | |
| rFVIIIFc ELISA Data | | | | | | | | | |
| Tmax | hr | 0.25 | 0.25 | 0.25 | 0.25 | 0.25 | 0.25 | 0.25 | 0.00 |
| Cmax | μg/mL | 0.4 | 0.334 | 0.374 | 0.348 | 0.383 | 0.323 | 0.368 | 0.030 |
| $T_{1/2}$ | hr | 11.4 | 13.3 | 9.3 | 12.7 | 12.7 | 14.1 | 11.9 | 1.7 |
| AUC | μg*hr/mL | 5.86 | 5.65 | 4.37 | 5.56 | 4.37 | 5.58 | 5.16 | 0.68 |
| CL | mL/hr/kg | 2.15 | 2.23 | 2.88 | 2.27 | 2.07 | 2.26 | 2.32 | 0.29 |
| Vz | mL/kg | 35.3 | 42.5 | 38.8 | 37.9 | 37.9 | 46.1 | 38.5 | 3.9 |
| MRT | hr | 15.3 | 17 | 12.1 | 17.1 | 17.3 | 19.2 | 15.8 | 2.4 |
| rFVIIIFc Chromogenic Activity Data | | | | | | | | | |
| Tmax | hr | 0.25 | 0.25 | 0.25 | 0.25 | 0.25 | 0.25 | 0.25 | 0.00 |
| Cmax | IU/mL | 4.31 | 3.82 | 3.54 | 4.13 | 4.12 | 3.68 | 3.93 | 0.30 |
| $T_{1/2}$ | hr | 13.4 | 12.0 | 11.6 | 17.5 | 12.4 | 29.4 | 16.1 | 6.9 |
| AUC | IU*hr/mL | 74.7 | 75.5 | 53.5 | 92.9 | 88.9 | 92.7 | 79.7 | 15.2 |
| CL | mL/hr/kg | 1.67 | 1.65 | 2.34 | 1.35 | 1.41 | 1.35 | 1.63 | 0.38 |
| Vz | mL/kg | 32.3 | 28.7 | 39.2 | 33.9 | 25.2 | 57.2 | 36.1 | 11.4 |
| MRT | hr | 17.8 | 16.8 | 16.9 | 25 | 19.2 | 33.3 | 21.5 | 6.5 |

TABLE 10

PK Parameters of XYNTHA ® after a single IV dose (125 IU/kg)

| PK Parameter | units | Group 1 | | | Group 2 | | | Average | SD |
|---|---|---|---|---|---|---|---|---|---|
| | | 604376 | 606595 | C36195 | C36066 | C36174 | 604362 | | |
| XYNTHA ® ELISA Data | | | | | | | | | |
| Tmax | hr | 0.25 | 4 | 0.25 | 0.25 | 0.25 | 0.25 | 0.88 | 1.53 |
| Cmax | IU/mL | 0.252 | 0.159 | 0.155 | 0.317 | 0.217 | 0.167 | 0.21 | 0.06 |
| $T_{1/2}$ | hr | 13.6 | 19.9 | 9.7 | 11 | 9.2 | nd | 12.7 | 4.4 |
| AUC | IU*hr/mL | 5.15 | 4.39 | 3.17 | 5.53 | 4.79 | 6.32 | 5.24 | 0.74 |
| CL | mL/hr/kg | 2.21 | 2.6 | 3.59 | 2.06 | 2.38 | nd | 2.57 | 0.61 |
| Vz | mL/kg | 43.4 | 74.7 | 50.1 | 32.9 | 31.5 | nd | 46.5 | 17.5 |
| MRT | hr | 19 | 28.4 | 14 | 16.1 | 15.9 | nd | 18.7 | 5.7 |
| XYNTHA ® Chromogenic Activity Data | | | | | | | | | |
| Tmax | hr | 0.25 | 0.25 | 0.25 | 0.25 | 0.25 | 0.25 | 0.25 | 0 |
| Cmax | IU/mL | 5.62 | 4.55 | 5.01 | 4.5 | 5.15 | 3.77 | 4.77 | 0.64 |
| $T_{1/2}$ | hr | 12.8 | 14.3 | 11.4 | 10.4 | 11.7 | 14.6 | 12.5 | 1.7 |
| AUC | IU*hr/mL | 97.1 | 104.2 | 71.3 | 70.7 | 94.0 | 82.8 | 86.7 | 14.0 |
| CL | mL/hr/kg | 1.29 | 1.20 | 1.75 | 1.77 | 1.33 | 1.51 | 1.48 | 0.24 |
| Vz | mL/kg | 23.7 | 24.8 | 28.9 | 26.6 | 22.5 | 31.8 | 26.4 | 3.5 |
| MRT | hr | 17.8 | 20.1 | 16.0 | 14.8 | 18.4 | 23.2 | 18.4 | 3.0 |

TABLE 11

Activation of Factor X

| | Km (nM) | Vmax (nM/min) |
|---|---|---|
| rFVIIIFc | 55.0 ± 5.9 | 65.6 ± 8.6 |
| BDD FVIII | 51.0 ± 8.7 | 73.5 ± 10.1 |

TABLE 12

Interaction with Factor IXa

| | Kd (nM) | Vmax (nM/min) |
|---|---|---|
| rFVIIIFc | 2.8 ± 0.4 | 4.5 ± 0.3 |
| BDD FVIII | 2.5 ± 0.3 | 4.0 ± 1.0 |

What is claimed is:

1. A method of reducing the incidence of a bleeding episode in a human subject with hemophilia A, comprising administering to the human subject multiple doses of a chimeric polypeptide comprising a Factor VIII portion and an Fc portion at a dosing interval of about three to about five days, wherein each of the multiple doses is about 25-100 IU/kg, wherein the chimeric polypeptide is administered intravenously.

2. The method of claim 1, wherein said dosing interval of said chimeric polypeptide is about every five days.

3. The method of claim 1, wherein said dosing interval of said chimeric polypeptide is about once every 4 days.

4. The method of claim 1, wherein the Factor VIII portion of said chimeric polypeptide is at least 90% or 95% identical to a Factor VIII amino acid sequence with a signal sequence selected from the group consisting of amino acids 1 to 1457 of SEQ ID NO:2; amino acids 1 to 2351 of SEQ ID NO:6; amino acids 1 to 759 of SEQ ID NO:8; amino acids 1 to 764 of SEQ ID NO:10; and amino acids 1 to 704 of SEQ ID NO:12 or at least 90% or 95% identical to a Factor VIII amino acid sequence without a signal sequence selected from the group consisting of amino acids 20 to 1457 of SEQ ID NO:2; amino acids 20 to 2351 of SEQ ID NO:6; amino acids 20 to 759 of SEQ ID NO:8; amino acids 20 to 764 of SEQ ID NO:10; and amino acids 21 to 704 of SEQ ID NO:12, and
wherein said chimeric polypeptide is in the form of a hybrid comprising a second polypeptide in association with said chimeric polypeptide, wherein said second polypeptide consists essentially of an Fc.

5. The method of claim 4, wherein said chimeric polypeptide comprises a sequence at least 90% or 95% identical to the Factor VIII and Fc amino acid sequence without a signal sequence set forth as amino acids 20 to 1684 of SEQ ID NO:2 or at least 90% or 95% identical to the Factor VIII and Fc amino acid sequence with a signal sequence set forth as amino acids 1 to 1684 of SEQ ID NO:2.

6. A method for prophylactic treatment of a spontaneous bleeding episode in a human subject with hemophilia A, comprising
administering to the subject multiple doses of a chimeric polypeptide comprising a Factor VIII portion and an Fc portion at a dosing interval of about three to about five days, wherein each of the multiple doses is about 25-65 IU/kg, wherein the chimeric polypeptide is administered intravenously.

7. The method of claim 6, wherein said Factor VIII portion is at least 90% or 95% identical to a Factor VIII amino acid sequence without a signal sequence selected from the group consisting of amino acids 20 to 1457 of SEQ ID NO:2; amino acids 20 to 2351 of SEQ ID NO:6; amino acids 20 to 759 of SEQ ID NO:8; amino acids 20 to 764 of SEQ ID NO:10; and amino acids 21 to 704 of SEQ ID NO:12.

8. The method of claim 6, wherein said Factor VIII portion is at least 90% or 95% identical to a Factor VIII amino acid sequence with a signal sequence selected from the group consisting of amino acids 1 to 1457 of SEQ ID NO:2; amino acids 1 to 2351 of SEQ ID NO:6; amino acids 1 to 759 of SEQ ID NO:8; amino acids 1 to 764 of SEQ ID NO:10; and amino acids 1 to 704 of SEQ ID NO:12, and
wherein said Fc portion is at least 90%, at least 95%, or 100% identical to an Fc amino acid sequence selected from the group consisting of amino acids 1458 to 1684 of SEQ ID NO:2;
amino acids 2352 to 2578 of SEQ ID NO:6; amino acids 760 to 986 of SEQ ID NO:8; amino acids 765 to 991 of SEQ ID NO:10; and amino acids 705 to 931 of SEQ ID NO:12.

9. The method of claim 6, wherein said chimeric polypeptide is a Factor VIII-Fc chimeric polypeptide in the form of a hybrid comprising a second polypeptide in association with said chimeric polypeptide, wherein said second polypeptide consists essentially of an Fc, wherein said chimeric polypeptide comprises a sequence at least 95% identical to the Factor VIII and Fc amino acid sequence without a signal sequence set forth as amino acids 20 to 1684 of SEQ ID NO:2 or at least 90% or 95% identical to the Factor VIII and Fc amino acid sequence with a signal sequence set forth as amino acids 1 to 1684 of SEQ ID NO:2.

10. The method of claim 1, wherein the chimeric polypeptide comprises a FVIII portion and two Fcs, wherein one of the Fcs is fused to the C-terminus of the light chain of the FVIII portion.

11. The method of claim 1, wherein the chimeric polypeptide is a rFVIIIFc monomer dimer hybrid recombinant fusion protein comprising a single molecule of recombinant B-domain deleted human FVIII fused to the dimeric Fc domain of human IgG1, with no intervening linker sequence.

12. The method of claim 1, wherein the hemophilia A is severe hemophilia A.

13. The method of claim 1, wherein each of the multiple doses is about 70-80 IU/kg.

14. The method of claim 1, wherein each of the multiple doses is about 80-90 IU/kg.

15. The method of claim 1, wherein each of the multiple doses is about 90-100 IU/kg.

16. The method of claim 6, wherein the chimeric polypeptide comprises a FVIII portion and two Fcs, wherein one of the Fcs is fused to the C-terminus of the light chain of the FVIII portion.

17. The method of claim 6, wherein the chimeric polypeptide is a rFVIIIFc monomer dimer hybrid recombinant fusion protein comprising a single molecule of recombinant B-domain deleted human FVIII fused to the dimeric Fc domain of human IgG1, with no intervening linker sequence.

18. The method of claim 6, wherein the hemophilia A is severe hemophilia A.

19. The method of claim 6, wherein each of the multiple doses is about 70-80 IU/kg.

20. The method of claim 6, wherein each of the multiple doses is about 80-90 IU/kg.

21. The method of claim 6, wherein each of the multiple doses is about 90-100 IU/kg.

22. A method for treating a bleeding episode in a human subject with hemophilia A, comprising
administering to the subject multiple doses of a chimeric polypeptide comprising a Factor VIII portion and an Fc portion at a dosing interval of about three to about five days, wherein each of the multiple doses is about 25-80 IU/kg, wherein the chimeric polypeptide is administered intravenously.

23. The method of claim 22, wherein said Factor VIII portion is at least 90% or 95% identical to a Factor VIII amino acid sequence without a signal sequence selected from the group consisting of amino acids 20 to 1457 of SEQ ID NO:2; amino acids 20 to 2351 of SEQ ID NO:6; amino acids 20 to 759 of SEQ ID NO:8; amino acids 20 to 764 of SEQ ID NO:10; and amino acids 21 to 704 of SEQ ID NO:12.

24. The method of claim 22, wherein said Factor VIII portion is at least 90% or 95% identical to a Factor VIII amino acid sequence with a signal sequence selected from the group consisting of amino acids 1 to 1457 of SEQ ID NO:2; amino acids 1 to 2351 of SEQ ID NO:6; amino acids 1 to 759 of SEQ ID NO:8; amino acids 1 to 764 of SEQ ID NO:10; and amino acids 1 to 704 of SEQ ID NO:12, and
wherein said Fc portion is at least 90%, at least 95%, or 100% identical to an Fc amino acid sequence selected from the group consisting of amino acids 1458 to 1684 of SEQ ID NO:2; amino acids 2352 to 2578 of SEQ ID NO:6; amino acids 760 to 986 of SEQ ID NO:8; amino acids 765 to 991 of SEQ ID NO:10; and amino acids 705 to 931 of SEQ ID NO:12.

25. The method of claim 22, wherein said chimeric polypeptide is a Factor VIII-Fc chimeric polypeptide in the form of a hybrid comprising a second polypeptide in association with said chimeric polypeptide, wherein said second polypeptide consists essentially of an Fc, wherein said chimeric polypeptide comprises a sequence at least 95% identical to the Factor VIII and Fc amino acid sequence without a signal sequence set forth as amino acids 20 to 1684 of SEQ ID NO:2 or at least 90% or 95% identical to the Factor VIII and Fc amino acid sequence with a signal sequence set forth as amino acids 1 to 1684 of SEQ ID NO:2.

26. The method of claim 22, wherein the chimeric polypeptide comprises a FVIII portion and two Fcs, wherein one of the Fcs is fused to the C-terminus of the light chain of the FVIII portion.

27. The method of claim 22, wherein the chimeric polypeptide is a rFVIIIFc monomer dimer hybrid recombinant fusion protein comprising a single molecule of recombinant B-domain deleted human FVIII fused to the dimeric Fc domain of human IgG1, with no intervening linker sequence.

28. The method of claim 22, wherein the hemophilia A is severe hemophilia A.

29. The method of claim 1, wherein the Factor VIII portion is pegylated Factor VIII.

30. The method of claim 1, wherein each of the multiple doses is 25-65 IU/kg.

31. The method of claim 1, wherein each of the multiple doses is 30-50 IU/kg.

32. The method of claim 1, wherein each of the multiple doses is 30-65 IU/kg.

33. The method of claim 1, wherein each of the multiple doses is 50 IU/kg.

34. The method of claim 1, wherein the dosing interval is every three days.

35. The method of claim 6, wherein the Factor VIII portion is pegylated Factor VIII.

36. The method of claim 6, wherein each of the multiple doses is 25-65 IU/kg.

37. The method of claim 6, wherein each of the multiple doses is 30-50 IU/kg.

38. The method of claim 6, wherein each of the multiple doses is 30-65 IU/kg.

39. The method of claim 6, wherein each of the multiple doses is 50 IU/kg.

40. The method of claim 6, wherein the dosing interval is every three days.

41. The method of claim 22, wherein the Factor VIII portion is pegylated Factor VIII.

42. The method of claim 22, wherein each of the multiple doses is 25-65 IU/kg.

43. The method of claim 22, wherein each of the multiple doses is 30-50 IU/kg.

44. The method of claim 22, wherein each of the multiple doses is 30-65 IU/kg.

45. The method of claim 22, wherein each of the multiple doses is 50 IU/kg.

46. The method of claim 22, wherein the dosing interval is every three days.

47. The method of claim 6, wherein each of the multiple doses is 50 IU/kg, and wherein the dosing interval is about every 4 days.

48. The method of claim 47, wherein the human subject with hemophilia A is at least 12 years old.

49. The method of claim 22, wherein each of the multiple doses is 80 IU/kg.

50. The method of claim 1, wherein the chimeric protein further comprises an intervening linker sequence between the Factor VIII portion and the Fc portion.

51. The method of claim 50, wherein the Fc portion comprises a Pro331Ser substitution.

52. The method of claim 50, wherein the Fc portion is a human immunoglobulin G1 (IgG1) Fc portion comprising three amino acid substitutions that do not cause a significant loss of Fc binding affinity to FcRn.

53. The method of claim 50, wherein the long-acting Factor VIII is pegylated.

54. The method of claim 50, wherein the Fc portion is a human immunoglobulin G2 (IgG2) Fc portion comprising three amino acid substitutions that do not cause a significant loss of Fc binding affinity to FcRn.

55. The method of claim 6, wherein the chimeric protein further comprises an intervening linker sequence between Factor VIII portion and the Fc portion.

56. The method of claim 55, wherein the Fc portion comprises a Pro331Ser substitution.

57. The method of claim 55, wherein the Fc portion is a human immunoglobulin G1 (IgG1) Fc portion comprising three amino acid substitutions that do not cause a significant loss of Fc binding affinity to FcRn.

58. The method of claim 55, wherein the long-acting Factor VIII is pegylated.

59. The method of claim 55, wherein the Fc portion is a human immunoglobulin G2 (IgG2) Fc portion comprising three amino acid substitutions that do not cause a significant loss of Fc binding affinity to FcRn.

60. The method of claim 22, wherein the chimeric protein further comprises an intervening linker sequence between the Factor VIII portion and the Fc portion.

61. The method of claim 60, wherein the Fc portion comprises a Pro331Ser substitution.

62. The method of claim 60, wherein the Fc portion is a human immunoglobulin G1 (IgG1) Fc portion comprising three amino acid substitutions that do not cause a significant loss of Fc binding affinity to FcRn.

63. The method of claim 60, wherein the long-acting Factor VIII is pegylated.

64. The method of claim 60, wherein the Fc portion is a human immunoglobulin G2 (IgG2) Fc portion comprising three amino acid substitutions that do not cause a significant loss of Fc binding affinity to FcRn.

* * * * *